United States Patent
Petsko et al.

(10) Patent No.: US 12,275,764 B2
(45) Date of Patent: *Apr. 15, 2025

(54) METHODS OF REDUCING FUS/TLS- OR TDP-43-MEDIATED NEURONAL CYTOTOXICITY IN AMYOTROPHIC LATERAL SCLEROSIS (ALS) BY UPF2

(71) Applicant: Brandeis University, Waltham, MA (US)

(72) Inventors: Greg Petsko, New York, NY (US); Dagmar Ringe, Cambridge, MA (US); Shulin Ju, Beavercreek, OH (US)

(73) Assignee: Brandeis University, Waltham, MA (US)

( * ) Notice: Subject to any disclaimer, the term of this patent is extended or adjusted under 35 U.S.C. 154(b) by 357 days.

This patent is subject to a terminal disclaimer.

(21) Appl. No.: 17/721,715

(22) Filed: Apr. 15, 2022

(65) Prior Publication Data

US 2023/0054101 A1 Feb. 23, 2023

Related U.S. Application Data

(63) Continuation of application No. 16/739,561, filed on Jan. 10, 2020, now Pat. No. 11,332,504, which is a continuation of application No. 14/434,737, filed as application No. PCT/US2013/063858 on Oct. 8, 2013, now Pat. No. 10,533,038.

(Continued)

(51) Int. Cl.
| | |
|---|---|
| *A61K 38/00* | (2006.01) |
| *A61K 9/00* | (2006.01) |
| *A61K 38/17* | (2006.01) |
| *A61K 48/00* | (2006.01) |
| *C07K 14/00* | (2006.01) |
| *C07K 14/47* | (2006.01) |
| *C12N 15/00* | (2006.01) |
| *C12N 15/09* | (2006.01) |
| *C12N 15/10* | (2006.01) |
| *C12N 15/11* | (2006.01) |
| *C12N 15/13* | (2006.01) |
| *C12Q 1/02* | (2006.01) |
| *G01N 33/50* | (2006.01) |
| *A01K 67/0275* | (2024.01) |
| *A61K 31/7088* | (2006.01) |
| *A61K 31/7105* | (2006.01) |
| *A61K 31/711* | (2006.01) |
| *A61K 31/7115* | (2006.01) |
| *A61K 31/7125* | (2006.01) |
| *A61K 35/12* | (2015.01) |
| *A61P 3/00* | (2006.01) |
| *C12N 15/85* | (2006.01) |
| *C12Q 1/6883* | (2018.01) |

(52) U.S. Cl.
CPC ........... *C07K 14/47* (2013.01); *A61K 9/0019* (2013.01); *A61K 38/17* (2013.01); *C12Q 1/025* (2013.01); *G01N 33/5058* (2013.01); *A01K 67/0275* (2013.01); *A01K 2207/05* (2013.01); *A01K 2207/10* (2013.01); *A01K 2207/20* (2013.01); *A01K 2217/206* (2013.01); *A01K 2267/03* (2013.01); *A01K 2267/0306* (2013.01); *A01K 2267/0318* (2013.01); *A01K 2267/0393* (2013.01); *A61K 31/7088* (2013.01); *A61K 31/7105* (2013.01); *A61K 31/711* (2013.01); *A61K 31/7115* (2013.01); *A61K 31/7125* (2013.01); *A61K 35/12* (2013.01); *A61K 38/00* (2013.01); *A61K 38/1709* (2013.01); *A61K 48/00* (2013.01); *A61K 48/005* (2013.01); *A61K 48/0066* (2013.01); *A61K 2300/00* (2013.01); *A61P 3/00* (2018.01); *C12N 15/85* (2013.01); *C12Q 1/6883* (2013.01); *C12Q 2600/106* (2013.01); *G01N 33/5023* (2013.01); *G01N 2333/47* (2013.01); *G01N 2500/10* (2013.01); *G01N 2800/56* (2013.01)

(58) Field of Classification Search
CPC ........ A61P 25/00; A61P 25/28; C12N 15/907; C12N 15/85; C12N 5/0618; A61K 38/17; A61K 17/09; A61K 48/00; A61K 35/00; C07K 14/47; C07K 14/00; C07K 14/4702; G01N 33/5058; G01N 2800/28; G01N 33/6896

See application file for complete search history.

(56) References Cited

U.S. PATENT DOCUMENTS

| | | |
|---|---|---|
| 8,486,635 B2 | 7/2013 | Hutton et al. |
| 8,603,814 B2 | 12/2013 | Pe'ery et al. |

(Continued)

FOREIGN PATENT DOCUMENTS

| | | | |
|---|---|---|---|
| WO | WO-98/45322 A2 | 10/1998 | |
| WO | WO-2005012875 A2 * | 2/2005 | ............. C12Q 1/485 |
| WO | WO-2014/058866 A2 | 4/2014 | |

OTHER PUBLICATIONS

Chamieh et al., Nat. Struct. Mol. Biol. 2008; 15:85-93. published online on Dec. 9, 2007. Doi: 10.1038/nsmb1330.*

(Continued)

*Primary Examiner* — Chang-Yu Wang
(74) *Attorney, Agent, or Firm* — Karen A. LeCuyer; DeWitt LLP

(57) ABSTRACT

Nonsense-mediated mRNA decay (NMD) polypeptides, nucleic acids encoding NMD polypeptides, and methods of using such polypeptides and nucleic acids in the treatment of ALS and in screening for agents for the treatment of ALS are described.

16 Claims, 1 Drawing Sheet
Specification includes a Sequence Listing.

Related U.S. Application Data

(60) Provisional application No. 61/712,322, filed on Oct. 11, 2012.

(56) References Cited

U.S. PATENT DOCUMENTS

| | | |
|---|---|---|
| 9,271,998 B2 | 3/2016 | Pe'ery et al. |
| 10,533,038 B2 | 1/2020 | Petsko et al. |
| 11,332,504 B2 | 5/2022 | Petsko et al. |
| 2003/0032158 A1 | 2/2003 | Peltz et al. |
| 2004/0127577 A1 | 7/2004 | Blaugrund et al. |
| 2010/0105034 A1 | 4/2010 | Hutton et al. |
| 2011/0039911 A1 | 2/2011 | Pe'ery et al. |
| 2013/0345142 A1 | 12/2013 | Hutton et al. |
| 2014/0073685 A1 | 3/2014 | Pe'ery et al. |
| 2014/0206637 A1 | 7/2014 | Pe'ery et al. |
| 2015/0259391 A1 | 9/2015 | Petsko et al. |
| 2020/0131236 A1 | 4/2020 | Petsko et al. |

OTHER PUBLICATIONS

Alaoui-Ismaili, M.H. and Falb, D., Design of second generation therapeutic recombinant bone morphogenetic proteins, Cytokine Growth Factor Rev., 20(5-6): 501-7 (2009).
Author Not Known, ALZFORUM: Networking for a Cure, DC: ALS Treatment Possibilities Presented at SfN, Satellite, 9 pages (Nov. 30, 2011).
Barmada, S. J. et al, Amelioration of toxicity in neuronal models of amyotrophic lateral sclerosis by hUPF1, PNAS, 112(25): 7821-7826 (2015).
Bruijn, L.I. et al., Unraveling the Mechanisms Involved in Motor Neuron Degeneration in ALS, Annu. Rev. Neurosci., 27: 723-749 (2004).
Budini, M. and Buratti, E., TDP-43 Autoregulation: Implications for Disease, J. Mol. Neurosci., 45:473-479 (2011).
Burgess, W. H. et al., Possible dissociation of the heparin-binding and mitogenic activities of heparin-binding (acidic fibroblast) growth factor-1 from its receptor-binding activities by site-directed mutagenesis of a single lysine residue, J. Cell Biol., 111(5 Pt 1): 2129-38 (1990).
Chen, Y. et al., DNA/RNA helicase gene mutations in a form of juvenile amyotrophic lateral sclerosis (ALS4), American Journal of Human Genetics, 74(6):1128-1135 (2004).
Guo, H.H. et al, Protein tolerance to random amino acid change, PNAS, 101(25): 9205-10 (2004).
Hergesheimer, R. C. et al., The debated toxic role of aggregated TDP-43 in amyotrophic lateral sclerosis: a resolution in sight?, Brain, 142:1176-1194 (2019).
Ilieva, H. et al., Non-cell autonomous toxicity in neurodegenerative disorders: ALS and beyond, The Journal of Cell Biology, 187(6):761-772 (2009).
International Search Report for PCT/US2013/063858, 4 pages (Aug. 19, 2014).
Jackson, K.L. et al, Preservation of forelimb function by UPF1 gene therapy in a rat model of TDP-43-induced motored paralysis, Gene Ther., 22(!): 20-28 (2015).
Ju, et al., A Yeast Model of FUS/TLS-Dependent Cytotoxicity, PLoS Biol, 9(4): e1001052, pp. 1-17 (2011).
Kervestin, S. and Jacobson, A., NMD: a multifaceted response to premature translation termination, Nature, 13:700-712 (2012).
Kryndushkin, D. and Shewmaker, F., Modeling ALS and FTLD proteinopathies in yeast, An efficient approach for studying protein aggregation and toxicity, Prion, 5(4): 250-257 (2011).
Kwiatkowski, T.J. et al., Mutations in the FUS/TLS gene on chromosome 16 cause familial amyotrophic lateral sclerosis, Science, 323(5918):1205-1208 (2009).
Lagier-Tourenne, C. et al., TDP-43 and FUS/TLS: emerging roles in RNA processing and neurodegeneration, Hum. Mol. Genet., 19: R46-R64 (2010).
Lagier-Tourenne, C., and Cleveland, D.W., Rethinking ALS: the FUS about TDP-43, Cell, 136(6): 1001-1004, 8 pages (2009).
Lazar, E. et al., Transforming growth factor alpha: mutation of aspartic acid 47 and leucine 48 results in different biological activities, Molecular Cellular Biology, 8(3): 1247-1252 (1988).
Lin, M. C., et al., Structure-function relationships in glucagon: properties of highly purified des-His-1-, monoiodo-, and (des-Asn-28, Thr-29)(homoserine lactone-27)-glucagon, Biochemistry USA, 14(8):1559-1563 (1975).
Ma, X. et al., A new mutation in BFSP2 (G1091A) causes autosomal dominant congenital lamellar cataracts, Mol. Vis., 14:1906-1911 (2008).
Maquat, L.E. and Carmichael, G.G., Quality control of mRNA function, Cell, 104(2):173-176 (2001).
Maquat, L.E., Nonsense-mediated mRNA decay in mammals, Journal of Cell Science, 118(9):1773-1776 (2005).
Maruyama, H. et al., Mutations of optineurin in amyotrophic lateral sclerosis, Nature, 465(7295):223-226 (2010).
Neumann, M., Molecular Neuropathology of TDP-43 Proteinopathies, International Journal of Molecular Sciences, 10:232-246 (2009).
Nicholson, P. and Mühlemann, O., Cutting the nonsense: the degradation of PTC-containing mRNAs, Biochemical Society Transactions, 38(6):1615-1620 (2010).
Nishimura, A.L. et al., A mutation in the vesicle-trafficking protein VAPB causes late-onset spinal muscular atrophy and amyotrophic lateral sclerosis, American Journal of Human Genetics, 75(5):822-831 (2004).
Ortega, J. A. et al., Nucleocytoplasmic Proteomic Analysis Uncovers eRF1 and Nonsense-Mediated Decay as Modifiers of ALS/FTD C9orf72 Toxicity, Neuron, 106:90-107 (2020).
Park, Y. et al., Nonsense-mediated mRNA decay factor UPF1 promotes aggresome formation, Nat. Commun., 11:3106 (2020).
Pawson, T. and Nash, P., Assembly of cell regulatory systems through protein interaction domains, Science, 300(5618): 445-52 (2003).
Polymenidou, M. et al., Long pre-mRNA depletion and RNA missplicing contribute to neuronal vulnerability from loss of TDP-43, Nature Neuroscience, 14(4):459-471 (2011).
Rehwinkel, J. et al., Nonsense-mediated mRNA decay factors act in concert to regulate common mRNA targets, RNA, 11(10):1530-1544 (2005).
Rehwinkel, J. et al., Nonsense-mediated mRNA decay: Target genes and functional diversification of effectors, Trends Biochemical Science, 31(11):639-646 (2006).
Rosen, D.R. et al., Mutations in Cu/Zn superoxide dismutase gene are associated with familial amyotrophic lateral sclerosis, Nature, 362(6415):59-62 (1993).
Rothstein, J.D. et al., Current hypotheses for the underlying biology of amyotrophic lateral sclerosis, Annals of Neurology, 65(1):S3-S9 (2009).
Rothstein, J.D., Therapeutic horizons for amyotrophic lateral sclerosis, Curr. Opin. In Neurobiol., 6: 679-687 (1996).
Sama, R. R. K. et al., Functions of FUS/TLS From DNA Repair to Stress Response: Implications for ALS, ASN Neuro., 1-18 (2014).
Schwartz, G. P. et al., A superactive insulin: [B10-aspartic acid]insulin(human), Proc. Natl. Acad. Sci USA, 84:6408-6411(1987).
Scotter, E. L. et al., TDP-43 Proteinopathy and ALS: Insights into Disease Mechanisms and Therapeutic Targets, Neurotherapeutics, 12:352-363 (2015).
Sreedharan, J. et al., TDP-43 mutations in familial and sporadic amyotrophic lateral sclerosis, Science, 319(5870):1668-1672 (2008).
Takahashi, K. and Yamanaka, K., Induction of pluripotent stem cells from mouse embryonic and adult fibroblast cultures by defined factors, Cell, 126(4):663-676 (2006).
Vaccaro, A. et al., Mutant TDP-43 and FUS Cause Age-Dependent Paralysis and Neurodegeneration in C. elegans, PLoS ONE, 7(2): e31321 1-10 (2012).
Vance, C. et al., Mutations in FUS, an RNA processing protein, cause familial amyotrophic lateral sclerosis type 6, Science, 323(5918):1208-1211 (2009).
Ward C.L. et al., A Loss of FUS/TLS function leads to impaired cellular proliferation, Cell Death and Disease, 5:e1572 (2014).

(56) References Cited

OTHER PUBLICATIONS

Wittkopp, N. et al., Nonsense-mediated mRNA decay effectors are essential for zebrafish embryonic development and survival, Molecular and Cellular Biology, 29(13):3517-3528 (2009).
Written Opinion for PCT/US2013/063858, 7 pages (Aug. 19, 2014).

* cited by examiner

METHODS OF REDUCING FUS/TLS- OR TDP-43-MEDIATED NEURONAL CYTOTOXICITY IN AMYOTROPHIC LATERAL SCLEROSIS (ALS) BY UPF2

CROSS REFERENCE TO RELATED APPLICATIONS

The present application is a continuation of U.S. application Ser. No. 16/739,561 (now U.S. Pat. No. 11,332,504), filed Jan. 10, 2020, which is a continuation of U.S. application Ser. No. 14/434,737 (now U.S. Pat. No. 10,533,038), filed Apr. 9, 2015, which is a national phase application under 35 U.S.C. § 371 of PCT International Application No. PCT/US2013/063858, filed Oct. 8, 2013, which claims the benefit of U.S. provisional application Ser. No. 61/712,322, filed Oct. 11, 2012, the contents of each of which are herein incorporated by reference in their entirety.

BACKGROUND

Amyotrophic lateral sclerosis (ALS, also called Lou Gehrig's disease) is a relentlessly progressive, fatal neurodegenerative disease with a prevalence of about 5 people out of 100,000 each year and an average age of onset of about 60 years. Patients with ALS suffer from degeneration of motor neurons in the brain and spinal cord, which leads to progressive muscular weakness. ALS accounts for about 1/300 to 1/400 of all deaths, which means that about 1,000,000 people now alive in the United States will develop ALS. Death typically occurs 3-5 years after disease onset, due to respiratory paralysis. There is no effective treatment for the disease; the only approved ALS drug (riluzole) extends the lifespan of some ALS patients by only about 3 months. Thus, there remains a need for new therapeutic approaches for treatment of ALS.

SUMMARY

The present disclosure encompasses the surprising discovery that agents involved in nonsense-mediated mRNA decay (NMD) can protect neuronal cells from damage associated with TDP-43 or FUS/TLS. The present invention therefore provides NMD agents for use in medicine, and specifically in treatment or prevention (e.g., delay of onset) of certain neurological disorders including specifically amyotrophic lateral sclerosis (ALS). For example, in various aspects, the present disclosure provides methods of reducing FUS/TLS or TDP-43 toxicity in a neuronal cell or glial cell suffering from or susceptible to such toxicity, comprising providing to the cell (e.g., in vitro or in vivo) a therapeutically effective amount of an NMD polypeptide, thereby reducing the FUS/TLS or TDP-43 toxicity in the cell. In some embodiments, the step of providing comprises administering a composition comprising the NMD polypeptide, a nucleic acid encoding the NMD polypeptide, and/or an activator of the NMD polypeptide. In some embodiments, the NMD polypeptide is a UPF1, UPF2, UPF3, SMG1, SMG5, SMG6, or SMG7 polypeptide. In some embodiments, the cell is a human neuronal cell or a human glial cell.

In various aspects, the present disclosure provides methods of treating a disease, disorder or condition associated with FUS/TLS or TDP-43 toxicity, comprising administering to a subject suffering from or susceptible to the disease, disorder or condition a therapeutically effective amount of an NMD polypeptide, a nucleic acid encoding an NMD polypeptide, and/or an activator or an NMD polypeptide, thereby treating the disease, disorder or condition. In some embodiments, the therapeutically effective amount is correlated with a statistically significant probability of reducing FUS/TLS or TDP-43 toxicity in a neuronal cell or a glial cell. In some embodiments, the therapeutically effective amount is correlated with a statistically significant probability of enhancing mRNA processing in a neuronal cell or a glial cell. In some embodiments, the disease, disorder or condition is not associated with SOD1 toxicity. In some embodiments, the NMD polypeptide, nucleic acid encoding the NMD polypeptide, and/or the activator of the NMD polypeptide is administered into the CNS of the subject, such as by intrathecal injection.

In various aspects, the present disclosure provides methods of treating ALS in a human subject, comprising: administering to a subject suffering from or susceptible to ALS a therapeutically effective amount of art NMD polypeptide, thereby treating the ALS in the subject. In some embodiments, the therapeutically effective amount is correlated with a statistically significant probability of reducing toxicity in a human neuronal cell or a human glial cell. In some embodiments, the toxicity is FUS/TLS or TDP-43 toxicity. In some embodiments, the toxicity is not SOD1toxicity. In some embodiments, the therapeutically effective amount is correlated with a statistically significant probability of enhancing mRNA processing in a human neuronal cell or a human glial cell.

In various aspects, the present disclosure provides methods of identifying an agent useful in the treatment of ALS, comprising: contacting a population of neuronal cells or glial cells that are suffering from or susceptible to FUS/TLS or TDP-43 toxicity with a test agent; determining a number of viable cells in the population after the contacting step; and comparing the number of viable cells to a control; wherein a test agent that increases the number of viable cells relative to the control is identified as an agent useful in the treatment of ALS. In some embodiments, the neuronal cells or the glial cells are transfected with a nucleic acid encoding FUS/TLS or TDP-43.

In various aspects, the present disclosure provides methods of identifying an agent useful in the treatment of ALS, comprising: contacting a population of neuronal cells or glial cells that are suffering from or susceptible to FUS/TLS or TDP-43 toxicity with a test agent; determining a level of mRNA processing in the population of neuronal cells or glial cells after the contacting step; and comparing the level of mRNA processing to a control; wherein a test agent that increases the level of mRNA processing relative to the control is identified as an agent useful in the treatment of ALS.

In various aspects, the present disclosure provides methods of identifying an agent useful in the treatment of ALS, comprising: contacting a first population of neuronal cells or glial cells that are suffering from or susceptible to FUS/TLS or TDP-43 toxicity with a test agent; determining a first number of viable cells in the first population after the contacting step; administering an NMD polypeptide to a second population of neuronal cells or glial cells that are suffering from or susceptible to FUS/TLS or TDP-43 toxicity; and determining a second number of viable cells in the second population after the administration step; wherein a first number of viable cells that is comparable to the second number of viable cells indicates the test agent is an agent useful in the treatment of ALS.

In various aspect, the present disclosure provides pharmaceutical compositions for treating ALS comprising an NMD polypeptide, a nucleic acid encoding an NMD polypeptide, or an activator of an NMD polypeptide, and a pharmaceutically acceptable excipient. In some embodiments, the pharmaceutical composition further comprising a targeting agent. In some embodiments, upon administration to a subject, the targeting agent selectively targets the composition to the brain.

In various aspect, the present disclosure provides methods of treating ALS in a human subject suffering from or susceptible to ALS, comprising: administering to the human subject a therapeutically effective amount of a UPF1 polypeptide, wherein the therapeutically effective amount is correlated with a statistically significant probability of reducing toxicity in a human neuronal cell or a human glial cell, thereby treating the ALS. In some embodiments, the subject has a mutation in an ALS2 gene, a VAPB gene, a SETX gene, a TDP-43 gene, a FUS/TLS gene, or an OPTN gene. In some embodiments, the subject does not have a mutation in a SOD1 gene.

BRIEF DESCRIPTION OF THE DRAWINGS

The following figures are presented for the purpose of illustration only, and are not intended to be limiting.

Figure 1A:
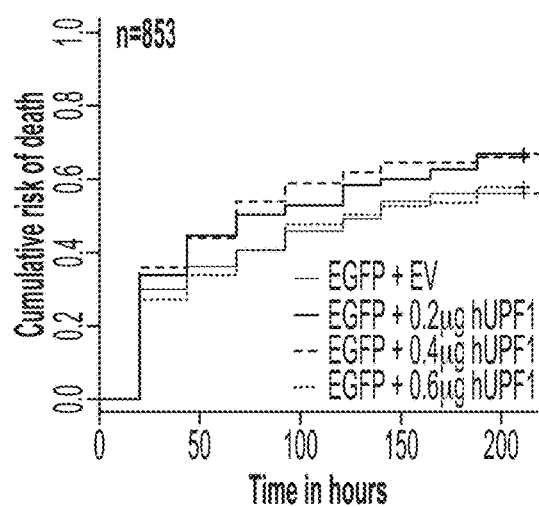
FIG. 1A is a graphical representation of cell death of neurons following expression of UDF1.

All publications, patent applications, patents, and other references mentioned herein, including GenBank database sequences, are incorporated by reference in their entirety. In case of conflict, the present specification, including definitions, will control. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Other features and advantages of the invention be apparent from the following detailed description, and from the claims.

DEFINITIONS

In order for the present invention to be more readily understood, certain terms are first defined below. Additional definitions for the following terms and other terms are set forth throughout the specification.

Approximately or about: As used herein, the term "approximately" or "about," as applied to one or more values of interest, refers to a value that is similar to a stated reference value. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Amelioration: As used herein, the term "amelioration" means the prevention, reduction or palliation of a state, or improvement of the state of a subject. Amelioration includes, but does not require, complete recovery or complete prevention of a disease condition.

Characteristic portion: As used herein, the term a "characteristic portion" of a substance, in the broadest sense, is one that shares some degree of sequence or structural identity with respect to the whole substance. In certain embodiments, a characteristic portion shares at least one functional characteristic with the intact substance. For example, in some embodiments, a "characteristic portion" of a polypeptide or protein is one that contains a continuous stretch of amino acids, or a collection of continuous stretches of amino acids, that together are characteristic of a polypeptide or protein. In some embodiments, each such continuous stretch generally contains at least 2, 5, 10, 15, 20, 50, or more amino acids. In some embodiments, such a continuous stretch includes certain residues whose position and identity are fixed; certain residues whose identity tolerates some variability (i.e., one of a few specified residues is accepted); and optionally certain residues whose identity is variable (i.e., any residue is accepted). In general, a characteristic portion of a substance (e.g., of a polypeptide or protein) is one that, in addition to the sequence and/or structural identity specified above, shares at least one functional characteristic with the relevant intact substance. In some embodiments, a characteristic portion may be biologically active.

Characteristic sequence: A "characteristic sequence" is a sequence that is found in all members of a family of polypeptides or nucleic acids, and therefore can be used by those of ordinary skill in the art to define members of the family.

Combination therapy: The term "combination therapy", as used herein, refers to those situations in which two or more different pharmaceutical agents are administered in overlapping regimens so that the subject is simultaneously exposed to both agents. When used in combination therapy, two or more different agents may be administered simultaneously or separately. This administration in combination can include simultaneous administration of the two or more agents in the same dosage form, simultaneous administration in separate dosage forms, and separate administration. That is, two or more agents can be formulated together in the same dosage form and administered simultaneously. Alternatively, two or more agents can be simultaneously administered, wherein the agents are present in separate formulations. In another alternative, a first agent can be administered just followed by one or more additional agents. In the separate administration protocol, two or more agents may be administered a few minutes apart, or a few hours apart, or a few days apart.

Comparable: The term "comparable", as used herein, refers to a system, set of conditions, effects, or results that is/are sufficiently similar to a test system, set of conditions, effects, or results, to permit scientifically legitimate comparison. Those of ordinary skill in the art will appreciate and understand which systems, sets of conditions, effects, or results are sufficiently similar to be "comparable" to any particular test system, set of conditions, effects, or results as described herein.

Correlates: The term "correlates", as use herein, has its ordinary meaning of "showing a correlation with". Those of ordinary skill in the art will appreciate that two features, items or values show a correlation with one another if they show a tendency to appear and/or to vary, together. In some embodiments, a correlation is statistically significant when its p-value is less than 0.05; in some embodiments, a correlation is statistically significant when its p-value is less than 0.01. In some embodiments, correlation is assessed by regression analysis. In some embodiments, a correlation is a correlation coefficient.

Homology: As used herein, the term "homology" refers to the overall relatedness between polymeric molecules, e.g., between nucleic acid molecules (e.g., DNA molecules and/or RNA molecules) and/or between polypeptide molecules. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% identical. In some embodiments, polymeric molecules are considered to be "homologous" to one another if their sequences are at least 25%, 30%, 35%, 40%, 45%, 50%, 55%, 60%, 65%, 70%, 75%, 80%, 85%, 90%, 95%, or 99% similar.

Identity: As used herein, the term "identity" refers to the overall relatedness between polymeric molecules, e.g., between nucleic acid molecules (e.g., DNA molecules and/or RNA molecules) and/or between polypeptide molecules. Calculation of the percent identity of two nucleic acid sequences, for example, can be performed by aligning the two sequences for optimal comparison purposes (e.g., gaps can be introduced in one or both of a first and a second nucleic acid sequences for optimal alignment and non-identical sequences can be disregarded for comparison purposes). In certain embodiments, the length of a sequence aligned for comparison purposes is at least 30%, at least 40%, at least 50%, at least 60%, at least 70%, at least 80%, at least 90%, at least 95%, or substantially 100% of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which needs to be introduced for optimal alignment of the two sequences. The comparison of sequences and determination of percent identity between two sequences can be accomplished using a mathematical algorithm. For example, the percent identity between two nucleotide sequences can be determined using the algorithm of Meyers and Miller (CABIOS, 1989, 4:11-17), which has been incorporated into the ALIGN program (version 2.0) using a PAM120 weight residue table, a gap length penalty of 12 and a gap penalty of 4. The percent identity between two nucleotide sequences can, alternatively, be determined using the GAP program in the GCG software package using an NWSgapdna.CMP matrix.

Improve, increase, or reduce: As used herein, the terms "improve," "increase" or "reduce," or grammatical equivalents, indicate values that are relative to a reference (e.g., baseline) measurement, such as a measurement taken under comparable conditions (e.g., in the same individual prior to initiation of treatment described herein, or a measurement in a control individual (or multiple control individuals) in the absence of treatment) described herein.

NMD agent: As used herein, the term "NMD agent" refers to an NMD polypeptide, a nucleic acid that encodes an NMD polypeptide, or an agent that increases NMD polypeptide level and/or activity. In some embodiments, an NMD agent is a therapeutic agent.

NMD polypeptide: As used herein, the term "NMD polypeptide" refers to a polypeptide whose amino acid sequence includes at least one characteristic sequence of and/or shows at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71% or 70% identity with a protein involved in nonsense-mediated mRNA decay (e.g., UPF1, UPF2, UPF3, SMG1, SMG5, SMG6, or SMG7). A wide variety of NMD sequences from flies, vertebrates, and mammals are known in the art, such as those described herein; in some embodiments, an NMD polypeptide shares at least one characteristic sequence of and/or shows the specified degree of overall sequence identity with one of the UPF1, UPF2, UPF3, SMG1, SMG5, SMG6, or SMG7 set forth herein (each of which may be considered a "reference" NMD polypeptide). In some embodiments, an NMD polypeptide as described herein shares at least one biological activity with a reference NMD polypeptide as set forth herein. In some such embodiment, the shared biological activity relates to nonsense-mediated mRNA decay.

Polypeptide: As used herein, a "polypeptide", generally speaking, is a string of at least two amino acids attached to one another by a peptide bond. In some embodiments, a polypeptide may include at least 3-5 amino acids, each of which is attached to others by way of at least one peptide bond. Those of ordinary skill in the art will appreciate that polypeptides sometimes include "non-natural" amino acids or other entities that nonetheless are capable of integrating into a polypeptide chain, optionally.

Protein: As used herein, the term "protein" refers to a polypeptide (i.e., a string of at least two amino acids linked to one another by peptide bonds). Proteins may include moieties other than amino acids (e.g., may be glycoproteins, proteoglycans, etc.) and/or may be otherwise processed or modified. Those of ordinary skill in the art will appreciate that a "protein" can be a complete polypeptide chain as produced by a cell (with or without a signal sequence), or can be a characteristic portion thereof. Those of ordinary skill will appreciate that a protein can sometimes include more than one polypeptide chain, for example linked by one or more disulfide bonds or associated by other means. Polypeptides may contain L-amino acids, D-amino acids, or both and may contain any of a variety of amino acid modifications or analogs known in the art. Useful modifications include, e.g., terminal acetylation, amidation, methylation, etc. In some embodiments, proteins may comprise natural amino acids, non-natural amino acids, synthetic amino acids, and combinations thereof. The term "peptide" is generally used to refer to a polypeptide having a length of less than about 100 amino acids, less than about 50 amino acids, less than 20 amino acids, or less than 10 amino acids.

Providing: As used herein, the term "providing" refers to performing a manipulation that causes an entity of interest to be present at a level and/or with an activity higher than that observed under otherwise comparable conditions prior to or absent the manipulation. In some embodiments, providing consists of or comprises administering the entity itself (alone or as part of a composition); in some embodiment, providing consists of or comprises administering an agent that causes an increase in level and/or activity of the entity of interest. For example, where the entity of interest is or comprises a polypeptide, in some embodiments, "providing" the polypeptide consists of or comprises administering the polypeptide (e.g., to a cell, whether isolated or in an organism); in some embodiments, "providing" the polypeptide consists of or comprises administering a nucleic acid encoding the polypeptide; in some embodiments, "providing" the polypeptide consists of or comprises administering an agent that results in increased expression of an endogenous copy of the polypeptide (e.g., by stimulating one or more of transcription, RNA processing, translation, etc. and/or by inhibiting an inhibitor of one of these).

Reference: A "reference" entity, system, amount, set of conditions, etc., is one against which a test entity, system, amount, set of conditions, etc. is compared as described herein. For example, in some embodiments, a "reference" individual is a control individual who is not suffering from or susceptible to any form of ALS disease; in some embodiments, a "reference" individual is a control individual afflicted with the same form of ALS disease as an individual being treated, and optionally who is about the same age as the individual being treated (to ensure that the stages of the disease in the treated individual and the control individual(s) are comparable).

Subject: As used herein, the term "subject", "individual", or "patient" refers to any organism upon which embodiments of the invention may be used or administered, e.g., for experimental, diagnostic, prophylactic, and/or therapeutic purposes. Typical subjects include animals (e.g., mammals such as mice, rats, rabbits, non-human primates, and humans; insects; worms; etc.).

Target cell or target tissue: As used herein, the terms "target cell" or "target tissue" refers to any cell, tissue, or organism that is affected by ALS to be treated, or any cell, tissue, or organism in which a protein involved in ALS is expressed. In some embodiments, target cells, target tissues, or target organisms include those cells, tissues, or organisms in which there is a detectable or abnormally high amount of FUS or TDP-43 (e.g., comparable to that observed in patients suffering from or susceptible to ALS). In some embodiments, target cells, target tissues, or target organisms include those cells, tissues, or organisms that display a disease-associated pathology, symptom, or feature.

Therapeutic agent: As used herein, the phrase "therapeutic agent" refers to any agent that, when administered to a subject, has a therapeutic effect and/or elicits a desired biological and/or pharmacological effect.

Therapeutic regimen: As used herein, the term "therapeutic regimen" refers to any method used to partially or completely alleviate, ameliorate, relieve, inhibit, prevent, delay onset of, reduce severity of and/or reduce incidence of one or more symptoms or features of a particular disease, disorder, and/or condition. It may include administration of one or more doses, optionally spaced apart by regular or varied time intervals. In some embodiments, a therapeutic regimen is one whose performance is designed to achieve and/or is correlated with achievement of (e.g., across a relevant population of cells, tissues, or organisms) a particular effect, e.g., reduction or elimination of a detrimental condition or disease such as ALS. In some embodiments, treatment includes administration of one or more therapeutic agents either simultaneously, sequentially or at different times, for the same or different amounts of time. In some embodiments, a "treatment regimen" includes genetic methods such as gene therapy, gene ablation or other methods known to induce or reduce expression (e.g., transcription, processing, and/or translation of a particular gene product, such as a primary transcript or mRNA).

Therapeutically effective amount: As used herein, the term "therapeutically effective amount" refers to an amount of a therapeutic agent (e.g., an NMD polypeptide) which confers a therapeutic effect on the treated subject, at a reasonable benefit/risk ratio applicable to any medical treatment. Such a therapeutic effect may be objective (i.e., measurable by some test or marker) subjective (i.e., subject gives an indication of or feels an effect). In some embodiments, "therapeutically effective amount" refers to an amount of a therapeutic agent or composition effective to treat, ameliorate, or prevent (e.g., delay onset of) a relevant disease or condition, and/or to exhibit a detectable therapeutic or preventative effect, such as by ameliorating symptoms associated with the disease, preventing or delaying onset of the disease, and/or also lessening severity or frequency of symptoms of the disease. A therapeutically effective amount is commonly administered in a dosing regimen that may comprise multiple unit doses. For any particular therapeutic agent, a therapeutically effective amount (and/or an appropriate unit dose within an effective dosing regimen) may vary, for example, depending on route of administration, or on combination with other therapeutic agents. Alternatively or additionally, a specific therapeutically effective amount (and/or unit dose) for any particular patient may depend upon a variety of factors including the particular form of ALS being treated; the severity of the ALS; the activity of the specific therapeutic agent employed; the specific composition employed; the age, body weight, general health, sex and diet of the patient; the time of administration, route of administration, and/or rate of excretion or metabolism of the specific therapeutic agent employed; the duration of the treatment; and like factors as is well known in the medical arts.

Treatment: As used herein, the term "treatment" (also "treat" or "treating") refers to any administration of a therapeutic agent (e.g., an NMD polypeptide) according to a therapeutic regimen that achieves a desired effect in that it partially or completely alleviates, ameliorates, relieves, inhibits, delays onset of, reduces severity of and/or reduces incidence of one or more symptoms or features of a particular disease, disorder, and/or condition (e.g., ALS); in some embodiments, administration of the therapeutic agent according to the therapeutic regimen is correlated with achievement of the desired effect. Such treatment may be of a subject who does not exhibit signs of the relevant disease, disorder and/or condition and/or of a subject who exhibits only early signs of the disease, disorder, and/or condition. Alternatively or additionally, such treatment may be of a subject who exhibits one or more established signs of the relevant disease, disorder and/or condition. In some embodiments, treatment may be of a subject who has been diagnosed as suffering from the relevant disease, disorder, and/or condition. In some embodiments, treatment may be of a subject known to have one or more susceptibility factors that are statistically correlated with increased risk of development of the relevant disease, disorder, and/or condition.

DETAILED DESCRIPTION

The present disclosure encompasses the surprising discovery that UPF1 can prevent neuronal toxicity due to TDP-43 or FUS/TLS. UPF1 is a protein involved in nonsense-mediated mRNA decay (NMD). Accordingly, the disclosure provides, among other things, various therapeutic modalities, including use of NMD polypeptides (e.g., UPF1, UPF2, UPF3, SMG1, SMG5, SMG6, or SMG7) to treat amyotrophic lateral sclerosis (ALS).

Amyotrophic Lateral Sclerosis (ALS)

ALS, which exists as both inherited and random forms, is characterized by degeneration of spinal motor neurons, leading to paralysis and death. While most forms of ALS are sporadic and idiopathic (sALS), about 10% of cases are inherited in a Mendelian fashion and are designated familial ALS (fALS). The present invention provides compositions and methods useful in treating ALS.

Using genetic analysis, several genes that cause fALS have been identified. The first mutations were identified in SOD1, which encodes the ubiquitously expressed copper/zinc superoxide dismutase. These variants are involved in about 20% of fALS cases worldwide (Rosen et al., Nature 362:59-62 (1993)). Other genes involved in fALS include genes coding for alsin (ALS2), vesicle associated membrane protein B (VAPB) (Nishimura et al. Am. J. Hum. Genet. 75:822-831 (2004)), senataxin (SETX) (Chen et al., Am. J. Hum. Genet. 74:1128-1135 (2004)), TAR-DNA-binding protein (TDP-43) (Sreedharan et al., Science 319:1668-1672 (2008)), fused in sarcoma or translocated liposarcoma (FUS/TLS) (Kwiatkowski et al., Science 323:1205-1208 (2009); Vance et al., Science 323:1208-1211 (2009)), and optineurin (OPTN) (Maruyama et al., Nature 465:223-226 (2010)). FUS/TLS is a nucleic acid binding protein that, when mutated, can cause a subset of fALS and can also increase risk for the sporadic disease. Although FUS/TLS is normally located predominantly in the nucleus, pathogenic mutant forms of FUS/TLS traffic to, and form inclusions in, the cytoplasm of affected spinal motor neurons or glia.

Studies of these genes have provided insight into the biochemical processes that may underlie ALS. Putative mechanisms of toxicity targeting motor neurons include glutamate excitotoxicity, oxidative damage, proteasome inhibition, mitochondrial dysfunction, ER stress, axonal transport defects, growth factor signaling deficiency, and glial cell dysfunction (Rothstein et al., Ann. Neurol. 65:S3-S9 (2009); Ilieva et al., J. Cell Biol. 187:761-772 (2009)).

Nonsense-Mediated mRNA Decay

In mammalian cells, expression of protein-encoding genes requires a series of steps in which pre-mRNA is processed to mRNA in the nucleus before mRNA is translated into protein in the cytoplasm. These steps are subject to quality control to ensure that only completely processed mRNA is exported to the cytoplasm (see, e.g., Maquat et al., Cell 104:173-176 (2001)). One form of quality control, called mRNA surveillance or nonsense-mediated mRNA decay (NMD), degrades mRNAs that prematurely terminate translation more than 50-55 nucleotides upstream of an exon-exon junction as a means to prevent the synthesis of potentially harmful truncated proteins (see, e.g., Maquat, J. Cell Sci. 118:1773-1776 (2005); Nicholson et al., Biochem. Soc. Trans. 38:1615-20 (2010)). A number of proteins are involved in NMD in mammalian cells, including UPF1, UPF2, UPF3, SMG1, SMG5, SMG6, and SMG7 (Wittkopp et al., Mol. Cell. Biol. 29:3517-3528 (2009); Rehwinkel et al, Trends Biochem. Sci. 31:639-646 (2006); Rehwinkel et al., RNA 11:1530-1544 (2005)). According to the present disclosure, any NMD polypeptides can be used to treat ALS in methods described herein.

Nucleic Acid Sequences Encoding NMD Polypeptides

Methods and compositions described herein include, for example, nucleic acids encoding NMD polypeptides (e.g., UPF1, UPF2, UPF3, SMG1, SMG5, SMG6, or SMG7). According to the present disclosure, such nucleic acids (and polypeptides) are useful in the treatment of ALS. In some embodiments, such nucleic acids have or include nucleotide sequences as set forth in SEQ ID NO:1, 3, 5, 7, 9, 11, or 13, or characteristic sequence elements thereof or therein. In some embodiments, useful nucleic acids show at least 100%, 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, or 70% overall sequence identity with one or more of SEQ ID NO:1, 3, 5, 7, 9, 11, or 13. Alternatively or additionally, in some embodiments, useful nucleic acids include at least 5, 6, 7, 8, 9, 10, 11, 12, 13, 14, 15, 16, 17, 18, 19, 20, 21, 22, 23, 24, 25 or more contiguous residues found in SEQ ID NO:1, 3, 5, 7, 9, 11 or 13. In some embodiments, useful nucleic acids are generated in vitro; in some embodiments, useful nucleic acids are generated in vivo. In some embodiments, useful nucleic acids are generated using genetic engineering techniques (e.g., for production and/or mutagenesis of a reference sequence). To give but a few examples, in some embodiments, nucleic acid variants (e.g., of SEQ ID NO:1, 3, 5, 7, 9, 11 or 13) are generated using techniques such as site directed mutagenesis, random chemical mutagenesis, Exonuclease III deletion procedures, and standard cloning techniques. In some embodiments, useful nucleic acids are generating using chemical synthesis and/or modification procedures.

A variety of methods of making nucleic acids that are "variants" with respect to a reference nucleic acid (e.g., a naturally-occurring or other reference nucleic acid) are well known in the art. These include, for example, procedures in which nucleic acid sequences obtained from natural isolates are modified to generate nucleic acids that encode polypeptides having characteristics that enhance their value in industrial or laboratory applications. In such some embodiments of such procedures, a large number of variant sequences having one or more nucleotide differences with respect to the sequence obtained from the natural isolate are generated and characterized. Typically, these nucleotide differences result in amino acid changes with respect to the polypeptides encoded by the nucleic acids from the natural isolates.

For example, variants can be created using error prone PCR (see, e.g., Leung et al., Technique 1:11-15, 1989; and Caldwell et al., PCR Methods Applic. 2:28-33, 1992). In error prone PCR, PCR is performed under conditions where the copying fidelity of the DNA polymerase is low, such that a rate of point mutations is obtained along the entire length of the PCR product. Briefly, in such procedures, nucleic acids to be mutagenized are mixed with PCR primers, reaction buffer, $MgCl_2$, $MnCl_2$, Taq polymerase, and an appropriate concentration of dNTPs for achieving a high rate of point mutation along the entire length of the PCR product. For example, the reaction can be performed using 20 fmoles of nucleic acid to be mutagenized, 30 pmole of each PCR primer, a reaction buffer comprising 50 mM KCl, 10 mM Tris HCl (pH 8.3), and 0.01% gelatin, 7 mM $MgCl_2$, 0.5 mM $MnCl_2$, 5 units of Taq polymerase, 0.2 mM dGTP, 0.2 mM dATP, 1 mM dCTP, and 1 mM dTTP. PCR can be performed for 30 cycles of 94° C. for 1 min, 45° C. for 1 min, and 72° C. for 1 min. However, it will be appreciated that these parameters can be varied as appropriate. The mutagenized nucleic acids are then cloned into an appropriate vector and the activities of the polypeptides encoded by the mutagenized nucleic acids are evaluated.

Variants can also be created using oligonucleotide directed mutagenesis to generate site-specific mutations in any cloned DNA of interest. Oligonucleotide mutagenesis is described in, for example, Reidhaar-Olson et al., Science 241:53-57 (1988). Briefly, in such procedures a plurality of double stranded oligonucleotides bearing one or more mutations to be introduced into the cloned DNA are synthesized and inserted into the cloned DNA to be mutagenized. Clones containing the mutagenized DNA are recovered, and the activities of the polypeptides they encode are assessed.

Another method for generating variants is assembly PCR. Assembly PCR involves the assembly of a PCR product from a mixture of small DNA fragments. A large number of different PCR reactions occur in parallel in the same vial, with the products of one reaction priming the products of another reaction. Assembly PCR is described in, for example, U.S. Pat. No, 5,965,408. Still another method of generating variants is sexual PCR mutagenesis. In sexual PCR mutagenesis, forced homologous recombination occurs between DNA molecules of different, but highly related, DNA sequence in vitro as a result of random fragmentation of the DNA molecule based on sequence homology. This is followed by fixation of the crossover by primer extension in a PCR reaction. Sexual PCR mutagenesis is described in, for example, Stemmer, Proc. Natl. Acad. Sci., USA 91:10747-10751 (1994).

Variants can also be created by in vivo mutagenesis. In some embodiments, random mutations in a nucleic acid sequence are generated by propagating the sequence in a bacterial strain, such as an *E. coli* strain, which carries mutations in one or more of the DNA repair pathways. Such "mutator" strains have a higher random mutation rate than that of a wild-type strain. Propagating a DNA sequence in one of these strains will generate random mutations within the DNA. Mutator strains suitable for use for in vivo mutagenesis are described in, for example, PCT Publication No. WO 91/16427.

Variants can also be generated using cassette mutagenesis. In cassette mutagenesis, a small region of a double stranded DNA molecule is replaced with a synthetic oligonucleotide "cassette" that differs front the native sequence. The oligonucleotide often contains a completely and/or partially randomized native sequence. Recursive ensemble mutagenesis can also be used to generate variants. Recursive ensemble mutagenesis is an algorithm for protein engineering (i.e., protein mutagenesis) developed to produce diverse populations of phenotypically related mutants whose members differ in amino acid sequence. This method uses a feedback mechanism to control successive rounds of combinatorial cassette mutagenesis. Recursive ensemble mutagenesis is described in, for example, Arkin et al., Proc. Natl. Acad. Sci., USA 89:7811-7815 (1992).

In some embodiments, variants are created using exponential ensemble mutagenesis. Exponential ensemble mutagenesis is a process for generating combinatorial libraries with a high percentage of unique and functional mutants, wherein small groups of residues are randomized in parallel to identify, at each altered position, amino acids which lead to functional proteins. Exponential ensemble mutagenesis is described in, for example, Delegrave et al., Biotech. Res. 11:1548-1552 (1993). Random and site-directed mutagenesis are described in, for example, Arnold, Curr. Opin. Biotech. 4:450-455 (1993). In some embodiments, variants are created using shuffling procedures wherein portions of a plurality of nucleic acids that encode distinct polypeptides are fused together to create chimeric nucleic acid sequences that encode chimeric polypeptides as described in, for example, U.S. Pat. Nos. 5,965,408 and 5,939,250.

In some embodiments, nucleic acids for use in accordance with the present disclosure comprise naturally-occurring nucleotide residues. In some embodiments, nucleic acids for use in accordance with the present disclosure include one or more nucleotide "analogs". A nucleotide analog is a nucleotide (i.e., an entity that is incorporated into a nucleic acid polymer without significantly disrupting the structure and/or function of that polymer) whose chemical structure differs from that of reference naturally-occurring ribonucleic or deoxyribonucleic acid residues adenine, guanine, cytosine, thymine, and uracil. In some embodiments, a nucleotide analog differs from its reference nucleotide at the base moiety, sugar moiety, and/or phosphate backbone. In some embodiments, a nucleotide analog contributes to one or more altered features in a nucleic acid polymer into which it is incorporated as compared with a comparable nucleic acid polymer containing its reference nucleotide rather than the analog. For example, in some embodiments, such analog-containing polymer shows improved, stability, hybridization, and/or solubility.

In some embodiments, base moiety alterations found in nucleotide analogs include deoxyuridine for deoxythymidine and 5-methyl-2'-deoxycytidine or 5-bromo-2'-deoxycytidine for deoxycytidine. In some embodiments, sugar moiety alterations found in nucleotide analogs include modification of the 2' hydroxyl of the ribose sugar to form 2'-O-methyl or 2'-O-allyl sugars. In some embodiments, deoxyribose phosphate backbone alterations found in nucleotide analogs include morpholino nucleic acids, in which each base moiety is linked to a six-membered, morpholino ring, or peptide nucleic acids, in which the deoxyphosphate backbone is replaced by a pseudopeptide backbone and the four bases are retained (see, e.g., Summerton et al., Antisense Nucleic Acid. Drug Dev. 7:187-195 (1997); Hyrup et al., Bioorgan. Med. Chem. 4:5-23(1996). Alternatively or additionally, nucleotide analogs may have a phosphorothioate or phosphorodithioate backbone, a phosphoroamidite, or an alkyl phosphotriester backbone.

In certain instances, an NMD polynucleotide or variant for use in accordance with the present disclosure includes alterations to codon(s) to optimize for expression in a particular host cell. For example, for expression in *E. coli,* an NMP polynucleotide or variant can include one or more altered codons as described in, e.g., Grosjean et al., Gene 18:199-209 (1982).

NMD Polypeptides

In some embodiments, methods and compositions described utilize NMD polypeptides (e.g., UPF1, UPF2, UPF3, SMG1, SMG5, SMG6, or SMG7 polypeptides). According to the present disclosure, such polypeptides are useful in the treatment of ALS. In some embodiments, such polypeptides useful in the practice of the present disclosure have or include amino acid sequences as set forth in SEQ ID NO:2, 4, 6, 8, 10, 12, or 14, or characteristic sequence elements thereof or therein. In some embodiments, useful polypeptides show at least 100%, 99%, 98%, 97%, 96%, 95%, 94%, 93%, 92%, 91%, 90%, 89%, 88%, 87%, 86%, 85%, 84%, 83%, 82% ,81%, 80%, 79%, 78%, 77%, 76%, 75%, 74%, 73%, 72%, 71%, or 70% overall sequence identity with one or more of SEQ ID NO:2, 4, 6, 8, 10, 12, or 14. Alternatively or additionally, in some embodiments, useful polypeptides include at least about 5, 10, 15, 20, 25, 30, 35, 40, 45, 50, 75. 100. or 150 or more contiguous amino acid residues found in SEQ ID NO:2, 4, 6, 8, 10, 12, or 14.

In some embodiments, a useful polypeptide differs from its reference polypeptide (e.g., a polypeptide having or including an amino acid sequence as set forth in SEQ ID NO:2, 4, 6, 8, 10, 12, or 14, or characteristic sequence elements thereof or therein) by one or more amino acid residues. For example, in some embodiments, the difference is a conservative or nonconservative substitution of one or more amino acid residues. Conservative substitutions are those that substitute a given amino acid in a polypeptide by another amino acid of similar characteristics. Typical conservative substitutions are the following replacements: replacement of an aliphatic amino acid, such as alanine, valine, leucine, and isoleucine, with another aliphatic amino acid; replacement of a serine with a threonine or vice versa; replacement of an acidic residue, such as aspartic acid and glutamic acid, with another acidic residue; replacement of a residue bearing an amide group, such as asparagine and glutamine, with another residue bearing an amide group; exchange of a basic residue, such as lysine and arginine, with another basic residue; and replacement of an aromatic residue, such as phenylalanine and tyrosine, with another aromatic residue.

In some embodiments, useful NMD polypeptides include a substituent group on one or more amino acid residues. Still other useful polypeptides are associated with (e.g., fused, linked, or coupled to) another moiety (e.g., a peptide or molecule). For example, useful NMD polypeptides can be fused, linked, or coupled to an amino acid sequence (e.g., a leader sequence, a secretory sequence, a proprotein sequence, a second polypeptide, or a sequence that facilitates purification, enrichment, or stabilization of the polypeptide). In certain other embodiments, a polypeptide includes a targeting agent, e.g., a targeting agent described herein.

A variety of methods of making polypeptides are known in the art and can be used to make NMD polypeptides. For example, NMD polypeptides can be recombinantly produced by utilizing a host cell system engineered to express a nucleic acid encoding an NMD polypeptide (e.g., a nucleic acid described herein). Alternatively or additionally, an NMD polypeptide can be produced by activating an endogenous gene (e.g., a nucleic acid encoding an NMD polypeptide present endogenously in a cell). Alternatively or additionally, an NMD polypeptide can be partially or fully prepared by chemical synthesis. Alternatively or additionally, an NMD polypeptide can be purified from natural sources.

Where an NMD polypeptide is recombinantly produced, any expression system can be used. Known expression systems include, without limitation, for example, egg, baculovirus, plant, yeast, or mammalian cells.

In some embodiments, an NMD polypeptide suitable for use in methods described herein are produced in mammalian cells. Non-limit examples of mammalian cells that can be used include BALB/c mouse myeloma line (NSO/l, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (e.g., HT1080); baby hamster kidney cells (BHK, ATCC CCL 10); Chinese hamster ovary cells +/−DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

Targeting Agents

An NMD agent described herein can provided in association with and/or can include a targeting agent.

The present disclosure is not limited to any particular targeting agent, and a variety of targeting agents can be used. Examples of such targeting agents include, but are not limited to, nucleic acids (e.g., RNA and DNA), polypeptides (e.g., receptor ligands, signal peptides, avidin, Protein A, and antigen binding proteins), polysaccharides, biotin, hydrophobic groups, hydrophilic groups, drugs, and any organic molecules that bind to target cells or target tissues (e.g., receptors on target cells or target tissues).

Targeting agents can be associated with NMD agents in any of a number of ways. For example, polypeptide targeting agents can be coupled to or fused to an NMD polypeptide. In other embodiments, a targeting agent is associated (e.g., covalently or noncovalently bound) to an NMD agent with either short (e.g., direct coupling), medium (e.g., using small-molecule bifunctional linkers such as SPDP (Pierce Biotechnology, Inc., Rockford, Ill.)), or long (e.g., PEG bifunctional linkers (Nektar Therapeutics, Inc., San Carlos, Calif.)) linkages.

In some instances, targeting agents are or comprise antigen binding proteins or antibodies or binding portions thereof. Antibodies can be generated to allow for specific targeting of antigens or immunogens (e.g., target cell or target tissue specific antigens). Such antibodies include, but are not limited to, polyclonal antibodies; monoclonal antibodies or antigen binding fragments thereof; modified antibodies such as chimeric antibodies, reshaped antibodies, humanized antibodies, or fragments thereof (e.g., Fv, Fab', Fab, F(ab')$_2$); or biosynthetic antibodies, e.g., single chain antibodies, single domain antibodies (DAB), Fvs, or single chain Fvs (scFv) (see, e.g., in Harlow et al., Using Antibodies: A Laboratory Manual: Portable Protocol I. Cold Spring Harbor Laboratory (Dec. 1, 1998); Zola, Monoclonal Antibodies: Preparation and Use of Monoclonal Antibodies and Engineered Antibody Derivatives, Springer Verlag (Dec. 15, 2000; 1st edition)). Antibody attachment can be performed by any known method e.g., through standard covalent binding to free amine groups (see, e.g., Torchilin et al., Hybridoma 6:229-240 (1987); Torchilin et al, Biochim. Biophys. Acta 1511:397-411 (2001); Masuko et al., Biomacromol. 6:800-884 (2005)).

In some instances, a targeting agent is or comprises a nucleic acid (e.g., RNA or DNA). In some examples, nucleic acid targeting agents are designed to hybridize by base pairing to a particular nucleic acid (e.g., chromosomal DNA, mRNA, or ribosomal RNA). In some situations, nucleic acid targeting agents bind a ligand on a target cell or target tissue. For example, a nucleic acid can bind human nerve growth factor (Binkley et al., Nuc. Acids Res. 23:3198-205 (1995)). Nucleic acids that bind ligands can be identified by known methods, such as SELEX procedures (see, e.g., U.S. Pat. Nos. 5,475,096; 5,270,163; and 5,475,096; and WO 97/38134; WO 98/33941; and WO 99/07724). In some embodiments, targeting agents can be or comprise aptamers, for example that bind to particular sequences.

In some embodiments, a targeting agent binds to a receptor on the surface of a brain cell to facilitate cellular uptake. For example, a targeting agent can be mannose-6-phosphate (M6P), bis-phosphorylated oligosaccharides, or IGF-II, which are useful for targeting the cation-independent mannose-6-phosphate receptor (CI-MPR) on a brain cell. In some embodiments, a targeting agent is or comprises ascorbate, which is taken up by a sodium-dependent-vitamin C transporter (SVCT2), (see, e.g., Tsukaguchi et al., Nature 399:70-75 (1999)), which is useful for targeting to a brain cell.

Therapeutic Administration

NMD agents (e.g., NMD polynucleotides, a nucleic acid encoding an NMD polypeptide, or an agent that increases NMD polypeptide level and/or activity) described herein can be used to treat ALS, e.g., subjects suffering from or susceptible to ALS. The route and/or mode of administration of an NMD agent described herein can vary depending upon the desired results. One with skill in the art, i.e., a physician, is aware that dosage regimens can be adjusted to provide the desired response, e.g., a therapeutic response.

Methods of administration include, but are not limited to, intradermal, intramuscular, intraperitoneal, intravenous, subcutaneous, intranasal, epidural, oral, sublingual, intracerebral, intrathecal, intravaginal, transdermal, rectal, by inhalation, or topical, particularly to the ears, nose, eyes, or skin. The mode of administration is left to the discretion of the practitioner.

In some instances, an NMD agent described herein (e.g., a pharmaceutical formulation of an NMD agent) can effectively cross the blood brain barrier and enter the brain. In other instances, an NMD agent can be delivered using techniques designed to permit or to enhance the ability of the formulation to cross the blood-brain barrier. Such techniques are known in the art (e.g., WO 89/10134; Cloughesy et al., J. Neurooncol. 26:125-132 (1995); and Begley, J. Pharm. Pharmacol, 48:136-146 (1996)). Components of a formulation can also be modified (e.g., chemically) using methods known in the art to facilitate their entry into the CNS.

For example, physical methods of transporting compositions across the blood-brain barrier include, but are not limited to, circumventing the blood-brain barrier entirely, or by creating openings in the blood-brain barrier. Circumvention methods include, but are not limited to, direct injection into the brain (see e.g., Papanastassiou et al., Gene Therapy 9: 398-406 (2002)) and implanting a delivery device in the brain (see e.g., Gill et al., Nature Med. 9: 589-595 (2003); and Gliadel Wafers™, Guildford Pharmaceutical). Methods of creating openings in the barrier include, but are not limited to, ultrasound (see e.g., U.S. Patent Publication No. 2002/0038086), osmotic pressure (e.g., by administration of hypertonic mannitol (Neuwelt, E. A., Implication of the Blood-Brain Barrier and its Manipulation, Vols 1 & 2, Plenum Press, N.Y. (1989))), permeabilization by, e.g., bradykinin or permeabilizer A-7 (see, e.g., U.S. Pat. Nos. 5,112,596, 5,268,164, 5,506,206, and 5,686,416), and transfection of neurons that straddle the blood-brain barrier with vectors containing genes encoding an NMD agent (see, e.g., U.S. Patent Publ. No. 20030083299).

Lipid-based methods can also be used to transport an NMD agent across the blood-brain barrier. Exemplary, non-limiting methods include encapsulating an NMD agent in liposomes that are coupled to a targeting agent described herein (e.g., an antibody that binds to receptors on vascular endothelium of the blood-brain barrier (see, e.g., U.S. Patent Publ. No. 20020025313). In certain other embodiments, a targeting agent is coated in low-density lipoprotein particles (see, e.g., U.S. Patent Publ. No. 20040204354) or apolipoprotein E (see, e.g., U.S. Patent Publ. No. 20040131692).

In some embodiments, an NMD agent is delivered to the CNS of a subject, e,g., by administering into the cerebrospinal fluid (CSF) of a subject in need of treatment. As used herein, intrathecal administration (also referred to as intrathecal injection) refers to an injection into the spinal canal (intrathecal space surrounding the spinal cord). Various techniques may be used including, without limitation, lateral cerebroventricular injection through a burrhole or cisternal or lumbar puncture or the like. Exemplary methods are described in Lazorthes et al., Adv. Tech. Stand. Neurosurg. 18:143-192 (1991), and Omaya, Cancer Drug Deliv. 1:169-179 (1984).

In some instances, an NMD agent described herein is administered locally. This can be achieved, for example, by local infusion during surgery, topical application (e.g., in a cream or lotion), by injection, by means of a catheter, by means of a suppository or enema, or by means of an implant, said implant being of a porous, non-porous, or gelatinous material, including membranes, such as sialastic membranes, or fibers. In some situations, an NMD agent described herein is introduced into the central nervous system, circulatory system or gastrointestinal tract by any suitable route, including intraventricular injection, intrathecal injection, paraspinal injection, epidural injection, enema, and by injection adjacent to a peripheral nerve.

Specifically, various devices can be used for intrathecal delivery of NMD agents described herein. In some embodiments, a device for intrathecal administration contains a fluid access port (e.g., injectable port); a hollow body (e.g., catheter) having a first flow orifice in fluid communication with the fluid access port and a second flow orifice configured for insertion into spinal cord; and a securing mechanism for securing the insertion of the hollow body in the spinal cord. Various other devices may be used to effect intrathecal administration of a therapeutic composition. For example, formulations containing NMD agents can be administered using an Ommaya reservoir that is in common use for intrathecally administering drugs for meningeal carcinomatosis (Lancet 2: 983-84, 1963). More specifically, in this method, a ventricular tube is inserted through a hole formed in the anterior horn and is connected to an Ommaya reservoir installed under the scalp, and the reservoir is subcutaneously punctured to intrathecally deliver an NMD agent, which is injected into the reservoir. Other devices for intrathecal administration of therapeutic compositions or formulations to an individual are described in U.S. Pat. No. 6,217.552. Alternatively, an NMD agent can be intrathecally given, for example, by a single injection, or continuous infusion. It should be understood that the dosage treatment may be in the form of a single dose administration or multiple doses.

In some embodiments, intrathecal administration can be performed by either lumbar puncture (i.e., slow bolus) or via a port-catheter delivery system (i.e., infusion or bolus).

Relative to intravenous administration, a single dose volume suitable for intrathecal administration is typically small. Typically, intrathecal delivery maintains the balance of the composition of the CSF as well as the intracranial pressure of the subject. In some embodiments, intrathecal delivery is performed absent the corresponding removal of CSF from a subject. In some embodiments, a suitable single dose volume may be e.g., less than about 10 ml, 8 ml, 6 ml, 5 ml, 4 ml, 3 ml, 2 ml, 1.5 ml, 1 ml, or 0.5 ml. In some embodiments, a suitable single dose volume may be about 0.5-5 ml, 0.5-4 ml, 0.5-3 ml, 0.5-2 ml, 0.5-1 ml, 1-3 ml, 1-5 ml, 1.5-3 ml, 1-4 ml, or 0.5-1.5 ml. In some embodiments, intrathecal delivery according to the present invention involves a step of removing a desired amount of CSF first. In some embodiments, less than about 10 ml (e.g., less than about 9 ml, 8 ml, 7 ml, 6 ml, 5 ml, 4 ml, 3 ml, 2 ml, 1 ml) of CSF is first removed before intrathecal administration. In those cases, a suitable single dose volume may be e.g., more than about 3 ml, 4 ml, 5 ml, 6 ml, 7 ml, 8 ml, 9 ml, 10 ml, 15 ml, or 20 ml.

Pulmonary administration can also be employed, e.g., by use of an inhaler or nebulizer, and formulation with an aerosolizing agent, or via perfusion in a fluorocarbon or synthetic pulmonary surfactant.

An NMD agent described herein can be formulated as a pharmaceutical composition that includes a suitable amount physiologically acceptable excipient (see, e.g., Remington's Pharmaceutical Sciences pp. 1447-1676 (Alfonso R. Gennaro, ed., 19th ed. 1995)). Such physiologically acceptable excipients can be, e.g., liquids, such as water and oils, including those of petroleum, animal, vegetable, or synthetic origin, such as peanut oil, soybean oil, mineral oil, sesame oil and the like. The physiologically acceptable excipients can be saline, gum acacia, gelatin, starch paste, talc, keratin, colloidal silica, urea and the like. In addition, auxiliary, stabilizing, thickening, lubricating, and coloring agents can be used. In one situation, the physiologically acceptable excipients are sterile when administered to an animal. The physiologically acceptable excipient should be stable under the conditions of manufacture and storage and should be preserved against the contaminating action of microorganisms. Saline solutions and aqueous dextrose and glycerol solutions can also be employed as liquid excipients, particularly for injectable solutions. Suitable physiologically acceptable excipients also include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. Other examples of suitable physiologically acceptable excipients are described in Remington's Pharmaceutical Sciences pp. 1447-1676 (Alfonso R. Gennaro, ed., 19th ed. 1995). The pharmaceutical compositions, if desired, can also contain minor amounts of wetting or emulsifying agents, or pH buffering agents.

Liquid carriers can be used in preparing solutions, suspensions, emulsions, syrups, and elixirs. An NMD agent described herein can be suspended in a pharmaceutically acceptable liquid carrier such as water, an organic solvent, a mixture of both, or pharmaceutically acceptable oils or fat. The liquid carrier can contain other suitable pharmaceutical additives including solubilizers emulsifiers, buffers, preservatives, sweeteners, flavoring agents, suspending agents, thickening agents, colors, viscosity regulators, stabilizers, or osmo-regulators. Suitable examples of liquid carriers for oral and parenteral administration include water (particular containing additives described herein, e.g., cellulose derivatives, including sodium carboxymethyl cellulose solution), alcohols (including monohydric alcohols and polyhydric alcohols, e.g., glycols) and their derivatives, and oils (e.g., fractionated coconut oil and arachis oil). For parenteral administration the carrier can also be an oily ester such as ethyl oleate and isopropyl myristate. The liquid carriers can be in sterile liquid form for administration. The liquid carrier for pressurized compositions can be halogenated hydrocarbon or other pharmaceutically acceptable propellant.

In other instances, an NMD agent described herein is formulated for intravenous administration. Compositions for intravenous administration can comprise a sterile isotonic aqueous buffer. The compositions can also include a solubilizing agent. Compositions for intravenous administration can optionally include a local anesthetic such as lidocaine to lessen pain at the site of the injection. The ingredients can be supplied either separately or mixed together in unit dosage form, for example, as a dry lyophilized powder or water-tree concentrate in a hermetically sealed container such as an ampule or sachette indicating the quantity of active agent. Where an NMD agent described herein is administered by infusion, it can be dispensed, for example, with an infusion bottle containing sterile pharmaceutical grade water or saline. Where an NMD agent described herein is administered by injection, an ampule of sterile water for injection or saline can be provided so that the ingredients can be mixed prior to administration.

An NMD agent described herein can be administered rectally or vaginally in the form of a conventional suppository. Suppository formulations can be made using methods known to those in the art from traditional materials, including cocoa butter, with or without the addition of waxes to alter the suppository's melting point, and glycerin. Water-soluble suppository bases, such as polyethylene glycols of various molecular weights, can also be used.

The amount of an NMD agent described herein that is effective for treating ALS can be determined using standard clinical techniques known to those with skill in the art. In addition, in vitro or in vivo assays can optionally be employed to help identify optimal dosage ranges. The precise dose to be employed can also depend on the route of administration, the condition, the seriousness of the condition being treated, as well as various physical factors related to the individual being treated, and can be decided according to the judgment of a health-care practitioner.

Compositions described herein (e.g., therapeutically effective amounts of compositions described herein) can be administered as single administrations or as multiple administrations. Such compositions can be administered at regular intervals, depending on the nature, severity and extent of the subject's condition (e.g., ALS). In some embodiments, a therapeutically effective amount of a therapeutic agent (e.g., an NMD agent) is administered intrathecally periodically at regular intervals (e.g., once every year, once every six months, once every five months, once every three months, bimonthly (once every two months), monthly (once every month), biweekly (once every two weeks), or weekly).

As used herein, the term "therapeutically effective amount" is largely determined based on the total amount of the therapeutic agent contained in pharmaceutical compositions described herein. Generally, a therapeutically effective amount is sufficient to achieve a meaningful benefit to a subject (e.g., treating, modulating, curing, preventing and/or ameliorating ALS). For example, a therapeutically effective amount can be an amount sufficient to achieve a desired therapeutic and/or prophylactic effect, such as an amount sufficient to treat ALS or the symptoms thereof. Generally, the amount of a therapeutic agent (e.g., an NMD agent) administered to a subject in need thereof will depend upon the characteristics of the subject. Such characteristics include the condition, disease severity, general health, age, sex and body weight of the subject. One of ordinary skill in the art will be readily able to determine appropriate dosages depending on these and other related factors. In addition, both objective and subjective assays can optionally be employed to identify optimal dosage ranges. A therapeutically effective amount can be administered in a dosing regimen that can include multiple unit doses.

In some embodiments, a therapeutically effective dose ranges from about 0.005 mg/kg brain weight to 500 mg/kg brain weight, e.g., from about 0.005 mg/kg brain weight to 400 mg/kg brain weight, from about 0.005 mg/kg brain weight to 300 mg/kg brain weight, from about 0.005 mg/kg brain weight to 200 mg/kg brain weight, from about 0.005 mg/kg brain weight to 100 mg/kg brain weight, from about 0.005 mg/kg brain weight to 90 mg/kg brain weight, from about 0.005 mg/kg brain weight to 80 mg/kg brain weight, from about 0.005 mg/kg brain weight to 70 mg/kg brain weight, from about 0.005 mg/kg brain weight to 60 mg/kg brain weight, from about 0.005 mg/kg brain weight to 50 mg/kg brain weight, from about 0.005 mg/kg brain weight to 40 mg/kg brain weight, from about 0.005 mg/kg brain weight to 30 mg/kg brain weight, from about 0.005 mg/kg brain weight to 25 mg/kg brain weight, from about 0.005 mg/kg brain weight to 20 mg/kg brain weight, from about 0.005 mg/kg brain weight to 15 mg/kg brain weight, from about 0.005 mg/kg brain weight to 10 mg/kg brain weight.

In some embodiments, a therapeutically effective dose is greater than about 0.1 mg/kg brain weight, greater than about 0.5 mg/kg brain weight, greater than about 1.0 mg/kg brain weight, greater than about 3 mg/kg brain weight, greater than about 5 mg/kg brain weight, greater than about 10 mg/kg brain weight, greater than about 15 mg/kg brain weight, greater than about 20 mg/kg brain weight, greater than about 30 mg/kg brain weight, greater than about 40 mg/kg brain weight, greater than about 50 mg/kg brain weight, greater than about 60 mg/kg brain weight, greater than 70 mg/kg brain weight, greater than about 80 mg/kg brain weight, greater than about 90 mg/kg brain weight, greater than about 100 mg/kg brain weight, greater than about 150 mg/kg brain weight, greater than about 200 mg/kg brain weight, greater than about 250 mg/kg brain weight, greater than about 300 mg/kg brain weight, greater than about 350 mg/kg brain weight, greater than about 400 mg/kg brain weight, greater than about 450 mg/kg brain weight, greater than about 500 mg/kg brain weight.

In some embodiments, a therapeutically effective dose can be expressed as mg/kg body weight. As one skilled in the art would appreciate, brain weights and body weights can be correlated (see, e.g., Dekaban, Ann. Neurol. 4:345-56 (1978)).

In some embodiments, a therapeutically effective dose can be expressed as mg/15 cc of CSF. As one skilled in the art would appreciate, therapeutically effective doses based on brain weights and body weights can be converted to mg/15 cc of CSF. For example, the volume of CSF in adult humans is approximately 150 mL (Johanson et al., Cerebrospinal Fluid Res. 14:5:10 (2008)). Therefore, single dose injections of 0.1 mg to 50 mg protein to adults would be approximately 0.01 mg/15 cc of CSF (0.1 mg) to 5.0 mg/15 cc of CSF (50 mg) doses in adults.

It is to be further understood that for any particular subject, specific dosage regimens can be adjusted over time according to the individual need and the professional judgment of the person administering or supervising the administration of an NMD agent and that dosage ranges set forth herein are exemplary only and are not intended to limit the scope or practice of the claimed invention.

In some instances, a pharmaceutical composition described herein is in unite dosage form, e.g., as a tablet, capsule, powder, solution, suspension, emulsion, granule, or suppository. In such form, the pharmaceutical composition can be sub-divided into unit doses containing appropriate quantities of an NMD agent described herein. The unit dosage form can be a packaged pharmaceutical composition, for example, packeted powders, vials, ampoules, pre-filled syringes or sachets containing liquids. The unit dosage form can be, for example, a capsule or tablet itself, or it can be the appropriate number of any such compositions in package form. Such unit dosage form can contain from about 1 mg/kg to about 250 mg/kg, and can be given in a single dose or in two or more divided doses.

Gene Therapy

In embodiments in which an NMD agent consists of or comprises a nucleic acid encoding an NMD polypeptide, the present disclosure includes methods of administering such nucleic acid to a subject to treat ALS.

In some embodiments, a nucleic acid encoding an NMD polypeptide is inserted into a viral vector for delivery to a subject. For example, retrovirus vectors can be used as a recombinant delivery system for transferring nucleic acids encoding NMD polypeptides vivo (see, e.g., Dropulic, Hum. Gene Ther. 22:649-57 (2011); and Kumar et al., Curr. Gene Ther. 11:144-53 (2011)). Retroviruses useful in methods of the present disclosure include, but are not limited to, murine leukemia virus (MLV), human immunodeficiency virus (HIV), equine infectious anaemia virus (EIAV), mouse mammary tumour virus (MMTV), Rous sarcoma virus (RSV), Fujinami sarcoma virus (FuSV), FBR marine osteosarcoma virus (FBR MSV), Moloney murine sarcoma virus (Mo-MSV), Abelson murine leukemia virus (A-MLV), Avian myelocytomatosis virus-29 (MC29), Avian erythroblastosis virus (AEV) and all other retroviridiae including lentiviruses (see, e.g., Coffin et al., "Retroviruses", 1997 Cold Spring Harbor Laboratory Press Eds: J M Coffin, S M Hughes, H E Varmus, pp 758-763)). A replication defective retrovirus can be packaged into virions that can be used to infect a target cell through the use of a helper virus by standard techniques (see, e.g., Current Protocols in Molecular Biology, Ausubel, F. M. et al. (eds.) Greene Publishing Associates, (1989), Sections 9.10-9.14).

In other embodiments, adenovirus-derived vectors are used to deliver nucleic acids encoding NMD polypeptides. The genome of an adenovirus can be manipulated such that it encodes and expresses an NMD polypeptide, but is inactivated in terms of its ability to replicate in a normal lytic viral life cycle (see, e.g., Berkner et al. (1988) BioTechniques 6:616; Rosenfeld et al. (1991) Science 252:431-434; and Rosenfeld et al. (1992) Cell 68:143-155). Suitable adenoviral vectors useful in the methods of the present disclosure include those derived from the adenovirus Ad type 5 d1324 or other strains of adenovirus (e.g., Ad2, Ad3, Ad7 etc.).

In some embodiments, an adeno-associated virus (AAV) is used to deliver a nucleic acid encoding an NMD polypeptide (see, e.g., Muzyczka et al. (1992) Curr. Topics in Micro. and Immunol. 158:97-129). A variety of nucleic acids have been introduced into different cell types using AAV vectors (see, e.g., Hermonate et al. (1984) Proc. Natl. Acad. Sci. USA 81:6466-6470; Tratschin et al. (1985) Mol. Cell. Biol. 4:2072-2081; Wondisford et al. (1988) Mol. Endocrinol. 2:32-39; Tratschin et al. (1984) J. Virol. 51:611-619; and Flotte et al. (1993) J. Biol. Chem 268:3781-3790). Particularly useful AAVs include those that normally infect humans (e.g., serotypes 1, 2, 3A, 3B, 4, 5, and 6) or primates (e.g., serotypes 1 and 4).

In other embodiments, non-viral methods are useful to deliver a nucleic acid encoding an NMD polypeptide to a subject. Such nonviral methods of gene transfer can exploit mechanisms normally used by mammalian cells for uptake and intracellular transport of macromolecules. For example, liposomal delivery systems, poly-lysine conjugates, and artificial viral envelopes can be used. In some embodiments, a nucleic acid encoding an NMD polypeptide is entrapped in liposomes bearing positive charges on their surface (e.g., lipofectins). In some embodiments, a liposome can be conjugated to a targeting agent described herein (see, e.g., Mizuno et al. (1992) No Shinkei Geka 20:547-551).

Certain cationic polymers ("complexation agents") known to spontaneously bind to and condense nucleic acids into nanoparticles can also be used including, e.g., naturally occurring proteins, peptides, or derivatives, as well as synthetic cationic polymers such as polyethylenimine (PEI), polylysine (PLL), etc. Many useful polymers contain both chargeable amino groups, to allow for ionic interaction with negatively charged DNA phosphate, and a degradable region, such as a hydrolyzable ester linkage. Examples of these include, without limitation, poly(alpha-(4-aminobutyl)-L-glycolic acid), network poly(amino ester), and poly (beta-amino esters). Such complexation agents can protect DNA against degradation, e.g., by nucleases, serum components, etc., and create a less negative surface charge, which may facilitate passage through hydrophobic membranes (e.g., cytoplasmic, lysosomal, endosomal, nuclear) of the cell. Certain complexation agents facilitate intracellular trafficking events such as endosomal escape, cytoplasmic transport, and nuclear entry, and can dissociate from the nucleic acid.

Cell-Based Therapy

An NMD polynucleotide can also be advantageously provided to a cell ex vivo, followed by administration of the living cell to the subject. In some embodiments, primary or secondary cells are genetically engineered to express an NMD polypeptide. Such cells can be obtained from a variety of tissues and include cell types which can be maintained propagated in culture. For example, primary and secondary cells include fibroblasts, endothelial cells, glial cells, and neural cells. In some embodiments, primary cells are obtained from an individual to whom a genetically engineered primary or secondary cells is to be administered. Primary cells can also be obtained from a donor (other than the recipient) of the same species or another species (e.g., mouse, rat, rabbit, cat, dog, pig, cow, bird, sheep, goat, horse).

Primary or secondary cells (e.g., of vertebrate or mammalian origin) can be transfected with a nucleic acid encoding an NMD polypeptide. In some embodiments, a cell is transfected with an exogenous nucleic acid sequence that includes a nucleic acid encoding an NMD polypeptide and an additional nucleic acid sequence (e.g., a regulatory sequence, e.g., a promoter, which causes expression, e.g., inducible expression or upregulation, of an endogenous NMD sequence). Transfected primary or secondary cells may also include DNA encoding a selectable marker which confers a selectable phenotype upon them, facilitating their identification and isolation.

Methods for treating disease by implanting a cell that has been modified to express a recombinant protein are also well known. See, for example, U.S. Pat. No. 5,399,346, disclosing methods for introducing a nucleic acid into a primary human cell for introduction into a human. Although use of human cells for ex vivo therapy is preferred in some embodiments, other cells such as bacterial cells may be implanted in a subject's vasculature, continuously releasing a therapeutic agent. See, for example, U.S. Pat. Nos. 4,309, 776 and 5,704,910.

Kits

An NMD agent described herein (e.g., a pharmaceutical composition comprising an NMD agent) can be provided in a kit. In some instances, the kit includes (a) a container that contains an NMD agent described herein (e.g., a pharmaceutical composition comprising an NMD agent) and, optionally (b) informational material. The informational material can be descriptive, instructional, marketing or other material that relates to the methods described herein and/or the use of an NMD agent, e.g., for therapeutic benefit.

The informational material of the kits is not limited in its form. In some instances, the informational material can include information about production of an NMD agent, molecular weight of an NMD agent, concentration, date of expiration, batch or production site information, and so forth. In other situations, the informational material relates to methods of administering an NMD agent, e.g., in a suitable amount, manner, or mode of administration (e.g., a dose, dosage form, or mode of administration described herein). The method can be a method of treating a subject having ALS.

In some cases, the informational material, e.g., instructions, is provided in printed matter, e.g., a printed text, drawing, and/or photograph, e.g., a label or printed sheet. The informational material can also be provided in other formats, such as Braille, computer readable material, video recording, or audio recording. In other instances, the informational material of the kit is contact information, e.g., a physical address, email address, website, or telephone number, where a user of the kit can obtain substantive information about an NMD agent therein and/or their use in the methods described herein. The informational material can also be provided in any combination of formats.

In addition to an NMD agent, the kit can include other ingredients, such as a solvent or buffer, a stabilizer, or a preservative. The kit can also include other agents, e.g., a second or third agent, e.g., other therapeutic agents. The components can be provided in any form, e.g., liquid, dried or lyophilized form. The components can be substantially pure (although they can be combined together or delivered separate from one another) and/or sterile. When the components are provided in a liquid solution, the liquid solution can be an aqueous solution, such as a sterile aqueous solution. When the components are provided as a dried form, reconstitution generally is by the addition of a suitable solvent. The solvent, e.g., sterile water or buffer, can optionally be provided in the kit.

The kit cart include one or more containers for an NMD agent or other agents. In some cases, the kit contains separate containers, dividers or compartments for an NMD agent and informational material. For example, an NMD agent can be contained in a bottle, vial, or syringe, and the informational material can be contained in a plastic sleeve or packet. In other situations, the separate elements of the kit are contained within a single, undivided container. For example, an NMD agent can be contained in a bottle, vial or syringe that has attached thereto the informational material in the form of a label. In some cases, the kit can include a plurality (e.g., a pack) of individual containers, each containing one or more unit dosage forms (e.g., a dosage form described herein) of an NMD agent. The containers can include a unit dosage, e.g., a unit that includes an NMD agent. For example, the kit can include a plurality of syringes, ampules, foil packets, blister packs, or medical devices, e.g., each containing a unit dose. The containers of the kits can be air tight, waterproof (e.g., impermeable to changes in moisture or evaporation), and/or light-tight.

The kit can optionally include a device suitable for administration of an NMD agent, e.g., a syringe or other suitable delivery device. The device can be provided preloaded with an NMD agent, e.g., in a unit dose, or can be empty, but suitable for loading.

Treatment of ALS

The present invention encompasses the surprising finding that NMD agents are useful, among other things, in the treatment or prevention (i.e., delay of onset) of ALS. UPF1 was initially identified as one of many genes able to rescue toxicity mediated by FUS/TLS in a yeast model (Ju et al., PLoS Biol. 9:e1001052 (2011)). However, the present finding that expressing UPF1 in neuronal cells expressing FUS/TLS or TDP-43 reduces cellular toxicity is surprising, especially given the finding that expression of UPF1 had no effect on the cytoplasmic levels of FUS/TLS or TDP-43 in the neuronal cells. Accordingly, in some embodiments, an NMD agent is provided to the central nervous system of a subject, e.g., a subject suffering from or susceptible to ALS. In some embodiments, an NMD agent is provided to one or more of target cells or tissues of brain, spinal cord, and/or peripheral organs. In some embodiments, target cells or tissues include those cells or tissues that display a disease-associated pathology, symptom, or feature. In some embodiments, target cells or tissues include those cells or tissues in which TDP-43 or FUS/TLS is expressed at an elevated level, e.g., cells in which TDP-43 or FUS/TLS is expressed at an elevated level in the cytoplasm of the cells. As used herein, a target tissue may be a brain target tissue, a spinal cord target tissue and/or a peripheral target tissue.

Compositions described herein can be provided directly into the CNS of a subject suffering from or at risk of developing ALS, thereby achieving a therapeutic concentration within the affected cells and tissues of the CNS (e.g., the brain). For example, one or more NMD agents can be provided to target cells or tissues of the brain, spinal cord and/or peripheral organs to treat ALS. As used herein, the term "treat" or "treatment" refers to amelioration of one or more symptoms associated with the disease, prevention or delay of the onset of one or more symptoms of the disease, and/or lessening of the severity or frequency of one or more symptoms of the disease.

In some embodiments, treatment refers to partially or complete alleviation, amelioration, relief, inhibition, delaying onset, reducing severity and/or incidence of neurological impairment in a patient suffering from or susceptible to ALS. As used herein, the term "neurological impairment" includes various symptoms associated with impairment of the central nervous system (e.g., the brain and spinal cord). Symptoms of neurological impairment may include, for example, developmental delay, progressive cognitive impairment, hearing loss, impaired speech development, deficits in motor skills, hyperactivity, aggressiveness and/or sleep disturbances, among others.

In some embodiments, treatment refers to decreased toxicity of various cells or tissues. In some embodiments, treatment refers to decreased neuronal toxicity due to FUS or TDP-43 in brain target tissues, spinal cord neurons, and/or peripheral target tissues. In certain embodiments, toxicity is decreased by about 5%, 10%, 15%, 20%, 25%, 30%, 35%, 40%, 45%, 50%, 55%, 60%, 65%, 70%, 75%, 80%, 85%, 90%, 95%, 100% or more as compared to a control. In some embodiments, toxicity is decreased by at least 1-fold, 2-fold, 3-fold, 4-fold, 5-fold, 6-fold, 7-fold, 8-fold, 9-fold or 10-fold as compared to a control. In some embodiments, toxicity is measured by tests known to those of ordinary skill in the art including, but not limited to, neuroimaging methods (e.g., CT scans, MRI, functional MRI, etc.).

In certain embodiments, treatment according to the present disclosure results in a reduction (e.g., about a 5%, 10%, 15%, 20%, 25%, 30%, 40%, 50%, 55%, 60%, 65%, 70%, 75%, 80%, 90%, 95%, 97.5%, 99% or more reduction) or a complete elimination of the presence, or alternatively the accumulation, of one or more pathological, clinical, or biological markers that are associated with ALS. For example, in some embodiments, upon administration to a subject, a pharmaceutical composition described herein demonstrates or achieves a reduction in muscle loss, muscle twitching, muscle weakness, spasticity, abnormal tendon reflexes, Babinski sign, breathing problems, facial weakness, slurred speech, loss of perception, loss of reasoning, loss of judgment, and/or loss of imagination.

In some embodiments, treatment refers to increased survival (e.g., survival time). For example, treatment can result in an increased life expectancy of a patient. In some embodiments, treatment results in an increased life expectancy of a patient by more than about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, about 100%, about 105%, about 110%, about 115%, about 120%, about 125%, about 130%, about 135%, about 140%, about 145%, about 150%, about 155%, about 160%, about 165%, about 170%, about 175%, about 180%, about 185%, about 190%, about 195%, about 200% or more, as compared to the average life expectancy of one or more control individuals with ALS without treatment. In some embodiments, treatment results in an increased life expectancy of a patient by more than about 6 months, about 7 months, about 8 months, about 9 months, about 10 months, about 11 months, about 12 months, about 2 years, about 3 years, about 4 years, about 5 years, about 6 years, about 7 years, about 8 years, about 9 years, about 10 years or more, as compared to the average life expectancy of one or more control individuals with ALS without treatment. In some embodiments, treatment results in long term survival of a patient. As used herein, the term "long term survival" refers to a survival time or life expectancy longer than about 40 years, 45 years, 50 years, 55 years, 60 years, or longer.

The term "improve," "increase" or "reduce," as used herein, indicates values that are relative to a control. In some embodiments, a suitable control is a baseline measurement, such as a measurement in the same individual prior to initiation of the treatment described herein, or a measurement in a control individual (or multiple control individuals) the absence of the treatment described herein. A "control individual" is an individual afflicted with ALS, who is about the same age and/or gender as the individual being treated (to ensure that the stages of the disease in the treated individual and the control individual(s) are comparable).

The individual (also referred to as "patient" or "subject") being treated is an individual (fetus, infant, child, adolescent, or adult human) having ALS or having the potential to develop ALS. In some instances, a subject to be treated is genetically predisposed to developing ALS. For example, a subject to be treated has a mutation in a SOD1 gene, ALS2 gene, VAPB gene, SETX gene, TDP-43 gene, FUS/TLS gene, and/or OPTN gene.

Combination Therapy

In some embodiments, an NMD agent described herein is administered to a subject in combination with one or more additional therapies to treat ALS or one or more symptoms of ALS. For example, an NMD agent can be administered in combination with riluzole (Rilutek®, Sanofi-Aventis, Bridgewater, NJ), baclofen, diazepam, trihexyphenidyl or amitriptyline.

In some embodiments, combined administration of an NMD agent and a second agent results in an improvement in ALS or a symptom thereof to an extent that is greater than one produced by either the NMD agent or the second agent alone. The difference between the combined effect and the effect of each agent alone can be a statistically significant difference.

In some embodiments, combined administration of an NMD agent and a second agent allows administration of the second agent at a reduced dose, at a reduced number of doses, and/or at a reduced frequency of dosage compared to a standard dosing regimen approved for the second agent. For example, approved standard regimen for Rilutek® is 50 mg every 12 hours. Accordingly, for administration in combination with an NMD agent, a therapeutically effective amount of Rilutek® can be a dosage of less than about 50 mg and/or a frequency of greater than about every 12 hours.

In some embodiments, an immunosuppressant agent known to the skilled artisan can be administered to a subject in combination with an NMD polypeptide described herein. Exemplary immunosuppressant agents include, without limitation, cyclosporine, FK506, rapamycin, CTLA4-Ig, anti-TNF agents (such as etanercept), daclizumab (e.g., Zenapax™), anti-CD2 agents, anti-CD4 agents, and anti-CD40 agents.

Methods of Identifying Modulators or NMD Polypeptide Expression or Activity

NMD polypeptides described herein (e.g., UPF1, UPF2, UPF3, SMG1, SMG5, SMG6, or SMG7 polypeptides) are useful for identifying agents that can be potentially used to treat ALS. For example, an agent that increases expression or activity of an NMD polypeptide can be identified as an agent that can be used to treat ALS. Numerous methods exist for evaluating whether an agent alters NMD polypeptide expression or NMD polypeptide activity or level. In one embodiment, the ability of a test agent to modulate (e.g., increase or decrease) (e.g., permanently or temporarily) expression from an NMD polynucleotide promoter is evaluated by e.g., routine reporter (e.g., LacZ, luciferase, or GFP) transcription assay. For example, a cell or transgenic animal whose genome comprises a reporter gene operably linked to an NMD polynucleotide promoter, can be contacted with a test agent, and the ability of the test agent to increase or decrease reporter activity is indicative of the ability of the agent to modulate an NMD polypeptide.

In some embodiments, effects of a test agent on NMD polypeptide expression or NMD polypeptide activity or level can be evaluated in a cell, cell lysate, or subject, preferably a non-human experimental mammal, and more preferably a rodent (e.g., a rat, mouse, rabbit), or explant thereof. Methods of assessing NMD polypeptide expression are well know in the art, e.g., Northern analysis, ribonuclease protection assay, reverse transcription-polymerase chain reaction (RT-PCR) or RNA in situ hybridization (see, e.g., Sambrook et al. Molecular Cloning: A Laboratory Manual ($3^{rd}$ ed. 2001)). The level of NMD polypeptide can be monitored by, e.g., Western analysis, immunoassay, or in situ hybridization. In some embodiments, a DNA construct encoding an NMD polypeptide/GFP fusion protein is transfected into cells, and level of GFP fluorescence in the presence or absence of a test agent is determined. An increase in fluorescence in the presence of the test agent is indicative of the ability of the test agent to increase NMD polypeptide level.

In some embodiments, the effect of a test agent on NMD polypeptide expression or NMD polypeptide activity or level is confirmed in a second assay, e.g., is observed as a change, in the presence of the test agent, in the ability of the NMD polypeptide to reduce toxicity of a cell, e.g., a neuronal cell, expressing TDP-43 and/or FUS.

Agents and test agents to be used in the methods described herein include crude or partially or substantially purified extracts of organic sources, e.g., botanical (e.g., herbal) and algal extracts, inorganic elements or compounds, as well as partially or substantially purified or synthetic agents, e.g., small molecules, polypeptides, antibodies, and polynucleotides, and libraries of these.

In one example, combinatorial chemical libraries can be produced or obtained that sample chemical compounds that are structurally or chemically related or unrelated. Preparation and screening of combinatorial chemical libraries is well known to those of skill in the art. Such combinatorial chemical libraries include, but are not limited to, peptide libraries (see, e.g., U.S. Pat. No. 5,010,175; Furka, Int. J. Pept. Prot. Res. 37:487-493 (1991); and Houghton et al., Nature 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries, peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), and small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

The invention is further illustrated by the following examples. The examples are provided for illustrative purposes only. They are not to be construed as limiting the scope or content of the invention in any way.

EXAMPLES

Example 1: Expression of UPF1 in Neurons Eliminates Toxicity of FUS or TDP-43

The present Example describes reduction of TDP-43 or FUS-mediated neuronal toxicity by UPF1.

A yeast model of ALS was used to identify a human gene, UPF1, which suppressed toxicity of FUS/TLS in yeast (Ju et al., PLoS Biol. 9:e1001052 (2011)). Further, UPF1 was able to suppress the cytotoxicity of ALS-associated TDP-43 mutations in yeast as well.

To test efficacy of UPF1 in reducing TDP-43 or FUS-mediated cytotoxicity in neurons, UPF1 was expressed in motor neurons expressing disease-associated FUS or TDP-43. Motor neurons were either isolated from mice or created from fibroblasts taken from human ALS patients using iPS cell techniques (described in Yamanaka et al, Cell 126:663-676 (2006)). FUS or TDP-43 were tagged with EGFP (Enhanced Green Fluorescent Protein) and expressed in motor neurons, which were visualized by fluorescent microscopy using mApple.

Figure 1B:
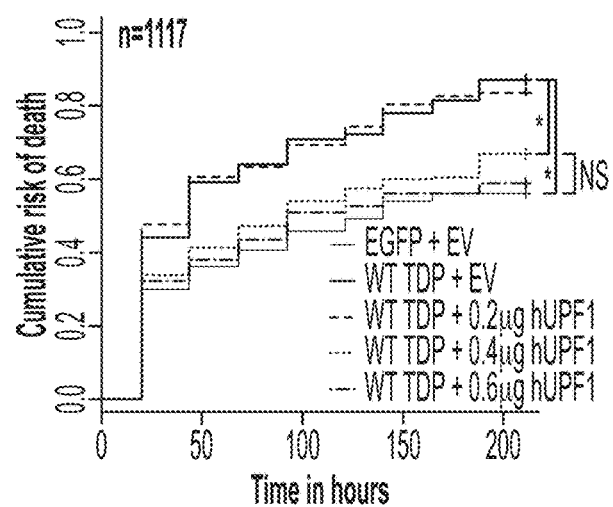
FIG. 1B is a graphical representation of cell death of neurons following expression of TDP-43 and UPF1.

The motor neurons died within a few days of FUS or TDP-43 expression due to toxicity of these ALS-related proteins. UPF1 was expressed in the motor neurons and Kaplan-Meyer survival curves were determined. As shown in FIG. 1A, UPF1 expression had no effect on survival of wild type neurons, indicating that UPF1 was not a generic survival factor. However, as shown in FIG. 1B, UPF1 was able to completely eliminate the toxicity of TDP-43 in a dose-dependent manner. UPF1 had a similar effect on cells expressing FUS (data not shown). Moreover, UPF1 expression was unable to rescue the toxicity of ALS-associated mutants of SOD1, demonstrating for the first time that SOD1-dependent fALS is a distinct disease mechanistically.

Example 2: Yeast Screening Assay for Compounds that Rescue FUS Toxicity

A drug screen based on the yeast model described in Example 1 was developed to identify compounds that rescue toxicity that resulted from FUS expression. Because the phenotype was rescue from cell death, the screen demonstrated exceptionally good signal-to noise, with a Z' score of around 0.8.

Briefly, two yeast strains were engineered: "1XFUS", in which a FUS gene was stably integrated at the HIS locus; and "1XVec", in which an empty vector was integrated at the same locus. The media used were YPRaffinose and 2XYPGalactose (2× concentrated). Yeast cells were grown by inoculating a single colony of 1XFUS strain or 1XVec strain into 2 ml YPRaffinose medium and were grown overnight at 30° C. The overnight cultures were then used to inoculate 50 ml YPRaffinose medium at OD600=0.2 and were grown for 24 hrs at 30° C.

The cultures were then diluted in 500 ml 2× YPGalactose medium at OD600=0.2. 384 well plates were pre-filled with 25 μl of each test compound at a concentration of 30 μM. A Multidrop was used to add 25 μl of the suspension of 1XFUS to each well on columns 1-23 of the plate; 1XVec was added to each well on column 24 as control. The yeast and compounds were mixed thoroughly. The plates were kept in a humidified incubator at 30° C. The OD600 of each plate was monitored at 24 hr and 48 hrs.

The compound(s) that rescued the growth of 1XFUS were selected and retested. The compounds that passed the retest were further checked in a 10-dose response experiment. The compounds that demonstrated good dose responses were re-ordered, and retested.

EQUIVALENTS

It is to be understood that while the invention has been described in conjunction with the detailed description thereof, the foregoing description is intended to illustrate and not limit the scope of the invention, which is defined by the scope of appended claims. Other aspects, advantages, and modifications are within the scope of the following claims.

```
                                 Sequences
                                                             (SEQ ID NO: 1)
UPF1 nucleotide sequence (GenBank Accession No. U59323.1, nt 176-3532)
   176                                                               atgag
   181 cgtggaggcg tacgggccca gctcgcagac tctcactttc ctggacacgg aggaggccga
   241 gctgcttggc gccgacacac agggctccga gttcgagttc accgacttta ctcttcctag
   301 ccagacgcag acgcccccg gcggccccgg cggcccggc ggtggoggcg cgggaagccc
   361 gggcggcgcg ggcgccggcg ctgcggcggg acagctcgac gcgcaggttg ggcccgaagg
   421 catcctgcag aacggggctg tggacgacag tgtagccaag accagccagt tgttggctga
   481 gttgaacttc gaggaagatg aagaagacac ctattacacg aaggacatcc ccatacacgc
   541 ctgcagttac tgtggaatac acgatcctgc ctgcgtggtt tactgtaata ccagcaagaa
   601 gtggttctgc aacggacgtg gaaatacttc tggcagccac attgtaaatc accttgtgag
   661 ggcaaaatgc aaagaggtga ccctgcacaa ggacgggccc ctgggggaga cagtcctgga
   721 gtgctacaac tgcggctgtc gcaacgtctt cctcctcggc ttcatcccgg ccaaagctga
   781 ctcagtggtg gtgctgctgt gcaggcagcc ctgtgccagc cagagcagcc tcaaggacat
   841 caactgggac agctcgcagt ggcagccgct gatccaggac cgctgcttcc tgtcctggct
   901 ggtcaagatc ccctccgagc aggagcagct gcgggcacgc cagatcacgg cacagcagat
   961 caacaagctg gaggagctgt ggaaggaaaa cccttatgcc acgctggagg acctggagaa
  1021 gccggggtg gacgaggagc cgcagcatgt cctcctgcgg tacgaggacg cctaccagta
  1081 ccagaacata ttcgggcccc tggtcaagct ggaggccgac tacgacaaga gctgaagga
  1141 gtcccagact caagataaca tcactgtcag gtgggacctg ggccttaaca agaagagaat
  1201 cgcctacttc actttgccca agactgactc tgacatgcgg ctcatgcagg gggatgagat
  1261 atgcctgcgg tacaaagggg accttgcgcc cctgtggaaa gggatcggcc acgtcatcaa
  1321 ggtccctgat aattatggcg atgagatcgc cattgagctg cggagcagcg tgggtgcacc
  1381 tgtggaggtg actcacaact tccaggtgga ttttgtgtgg aagtcgacct cctttgacag
  1441 gatgcagagc gcattgaaaa cgtttgccgt ggatgagacc tcggtgtctg gctacatcta
  1501 ccacaagctg ttgggccacg aggtggagga cgtaatcacc aagtgccagc tgcccaagcg
```

-continued

| Sequences |
|---|

```
1561  cttcacggcg cagggcctcc ccgacctcaa ccactcccag gtttatgccg tgaagactgt
1621  gctgcaaaga ccactgagcc tgatccaggg cccgccaggc acggggaaga cggtgacgtc
1681  ggccaccatc gtctaccacc tggcccggca aggcaacggg ccggtgctgg tgtgtgctcc
1741  gagcaacatc gccgtggacc agctaacgga gaagatccac cagacggggc taaaggtcgt
1801  gcgcctctgc gccaagagcc gtgaggccat cgactcccccg gtgtcttttc tggccctgca
1861  caaccagatc aggaacatgg acagcatgcc tgagctgcag aagctgcagc agctgaaaga
1921  cgagactggg gagctgtcgt ctgccgacga gaagcggtac cgggccttga agcgcaccgc
1981  agagagagag ctgctgatga acgcagatgt catctgctgc acatgtgtgg gcgccggtga
2041  cccgaggctg gccaagatgc agttccgctc cattttaatc gacgaaagca cccaggccac
2101  cgagccggag tgcatggttc ccgtggtcct cggggccaag cagctgatcc ttgtaggcga
2161  ccactgccag ctgggcccag tggtgatgtg caagaaggcg gccaaggccg gctgtcaca
2221  gtcgctcttc gagcgcctgg tggtgctggg catccggccc atccgcctgc aggtccagta
2281  ccggatgcac cctgcactca gcgccttccc atccaacatc ttctacgagg gctccctcca
2341  gaatggtgtc actgcagcgg atcgtgtgaa aagggatttt gacttccagt ggccccaacc
2401  cgataaaccg atgttcttct acgtgaccca gggccaagag gagattgcca gctcgggcac
2461  ctcctacctg aacaggaccg aggctgcgaa cgtggagaag atcaccacga agttgctgaa
2523  ggcaggcgcc aagccggacc agattggcat catcacgccc tacgagggcc agcgctccta
2581  cctggtgcag tacatgcagt tcagcggctc cctgcacacc aagctctacc aggaagtgga
2641  gatcgccagt gtggacgcct ttcagggacg cgagaaggac ttcatcatcc tgtcctgtgt
2701  gcgggccaac gagcaccacg gcattggctt tttaaatgac cccaggcgtc tgaacgtggc
2761  cctgaccaga gcaaggtatg gcgtcatcat tgtgggcaac ccgaaggcac tatcaaagca
2821  gccgctctgg aaccacctgc tgaactacta taaggagcag aaggtgctgg tggaggggcc
2881  gctcaacaac ctgcgtgaga gcctcatgca gttcagcaag ccacggaagc tggtcaacac
2941  tatcaacccg ggagcccgct tcatgaccac agccatgtat gatgcccggg aggccatcat
3001  cccaggctcc gtctatgatc ggagcagcca gggccggcct tccagcatgt acttccagac
3061  ccatgaccag attggcatga tcagtgccgg ccctagccac gtggctgcca tgaacattcc
3121  catcccttc aacctggtca tgccacccat gccaccgcct ggctattttg acaagccaa
3181  cgggcctgct gcagggcgag cacccccgaa aggcaagact ggtcgtgggg acgccagaa
3241  gaaccgcttt gggcttcctg acccagcca gactaacctc cccaacagcc aagccagcca
3301  ggatgtggcg ccacagccct tctctcaggg cgccctgacg cagggctaca tctccatgag
3361  ccagccttcc cagatgagcc agcccggcct ctcccagccg gagctgtccc aggacagtta
3421  ccttggtgac gagtttaaat cacaaatcga cgtggcgctc tcacaggact ccacgtacca
3481  gggagagcgg gcttaccagc atggcggggt gacggggctg tcccagtatt aa
```

(SEQ ID NO: 2)
UPF1 amino acid sequence (GenBank Accession No. AAC51140.1)
```
  1  msveaygpss qtltfldtee aellgadtqg sefeftaftl psqtqtppgg pggpggggag
 61  spggagagaa agqldaqvgp cgilqngavd dsvaktsqll aelnfeedee dtyytkdlpi
121  hacsycgihd pacvvycnts kkwfcngrgn tsgshivnhl vrakckcvtl hkdgplgetv
181  lecyncgcrn vfllgfipak adsvvvllcr qpcasqsslk dinwdssqwq pliqdrcfls
```

-continued

| Sequences |
|---|
| 241 wlvkipseqe qlrarqitaq qinkleelwk enpsatledl ekpgvdeepg hvllryeday |
| 301 qyqnifgplv kleadydkkl kesqtqdnit vrwdlglnkk riayftlpkt dsdmrlmqgd |
| 361 eiclrykgdl aplwkgighv ikvpdnygde iaielrssvg apvevthnfg vdfvwkstsf |
| 421 drmqsalktf avdetsvsgy iyhkllghcv edvitkcqlp krftaqglpd lnhsqvyavk |
| 481 tvlqrplsli qgppgtgktv tsativyhla rqgngpvlvc apsniavdql tekihqtglk |
| 541 vvrlcaksre aidspvsfla lhnqirnmds mpelqklqql kdetgelssa dekryralkr |
| 601 taerellmna dvicctcvga gdprlakmgf rsilidestq atepecmvpv vlgakqlilv |
| 661 gdhcqlgpvv mckkaakagl sqslferlvv lgirpirlqv qyrmhpalsa fpsnifyegs |
| 721 lqngvtaadr vkkgfdfqwp qpdkpmffyv tqgqeeiass gtsylnrtca anvckittkl |
| 781 lkagakpdgi giitpyeqgr sylvgymgfs gslhtklyge veiasvdafg grekdfiils |
| 841 cvranehqgi gflndprrln valtrarygv iivgnpkals kqplwnhlln yykeqkvlvc |
| 901 gplnnlrcsl mgfskprklv ntinpgarfm ttamydarea iipgsvydrs sqgrpssmyf |
| 961 qthdqigmis agpshvaamn ipipfnlvmp pmpppgyfgq angpaagrgt pkgktgrggr |
| 1021 qknrfglpgp sqtnlpnsqa sqdvasqpfs qgaltqgyis msqpsqmsqp glsqpelsqd |
| 1081 sylgdefksq idvalsqdst yqgerayqhg gvtglsqy |

(SEQ ID NO: 3)
UPF2 nucleotide sequence (GenBank Accession No. AF318574.1) (nt 76-3894)

| 76 atgcc agctgagcgt aaaaagccag caagtatgga agaaaaagac |
|---|
| 121 tctttaccaa acaacaagga aaaagactgc agtgaaaggc ggacagtgag cagcaaggag |
| 181 aggccaaaag acgatatcaa gctcactgcc aagaaggagg tcagcaaggc ccctgaagac |
| 241 aagaagaaga gactggaaga tgataagaga aaaaaggaag acaaggaacg caagaaaaaa |
| 301 gacgaagaaa aggtgaaggc acaggaagaa tcaaagaaaa aagaagagga gaaaaaaaag |
| 361 aaacatcaag aggaagagag aaagaagcaa gaagagcagg ccaaacgtca gcaagaagaa |
| 421 gaagcagctg ctcagatgaa agaaaaagaa gaatccattc agcttcatca ggaagcttgg |
| 481 gaacgacatc atttaagaaa ggaacttcgt agcaaaaacc aaaatgctcc ggacagccga |
| 541 ccagaggaaa acttcttcag ccgcctcgac tcaagtctga gaaaaaatac tgcttttgtc |
| 601 aagaaactaa aaactattac agaacaacag agagactoct tgtcccatga tttttaatggc |
| 661 ctaaatttaa gcaaatacat tgcagaagct gtagcttcca tcgtggaagc aaaactaaaa |
| 721 atctctgatg tgaactgtgc tgtgcacctc tgctctctct ttcaccagcg ttatgctgac |
| 781 tttgccccat cacttcttca ggtctggaaa aaacattttg aagcaaggaa agaggagaaa |
| 841 acacctaaca tcaccaagtt aagaactgat tgcgtttta ttgcagaatt gacaatagtt |
| 901 gggatttca ctgacaagga aggtcttcc ttaatctatg aacagctaaa aatatattt |
| 961 aatgctgatc gggagtccca cactcatgtc tctgtagtga ttagtttctg tcgacattgt |
| 1021 ggagatgata ttgctggact tgtaccaagg aaagtaaaga gtgctgcaga aagtttaat |
| 1081 ttgagttttc ctcctagtga gataattagt ccagagaaac aacagccctt ccagaatctt |
| 1141 ttaaaagagt actttacgtc tttgaccaaa cacctgaaaa gggaccacag ggagctccag |
| 1201 aatactgaga gacaaaacag gcgcattcta cattctaaag gggagctcag tgaagataga |
| 1261 cataaacagt atgaggaatt tgctatgtct taccagaagc tgctggcaaa ttctcaatcc |
| 1321 ttagcagacc ctttggatga aaatatgcca gatcttcctc aagcaaaacc cacaccagaa |
| 1381 gaacatgggc ctggaattga tatattcaca cctggtaaac ctggagaata tgacttggaa |

-continued

| Sequences |
|---|
| 1441 ggtggtatat gggaagatga agatgctcgg aattttatg agaacctcat tgatttgaag |
| 1501 gcttttgtcc cagccatctt gtttaaagac aatgaaaaaa gttgtcagaa taaagagtcc |
| 1561 aacaaagatg ataccaaaga ggcaaaagaa tctaaggaga ataaggaggt atcaagtccc |
| 1621 gatgatttgg aacttgagtt ggagaatcta gaaattaatg atgacacctt agaattagag |
| 1681 ggtggagatg aagctgaaga tcttacaaag aaacttcttg atgaacaaga caagaagat |
| 1741 gaggaagcca gcactggatc tcatctcaag ctcatagtag atgctttcct acagcagtta |
| 1801 cccaactgtg tcaaccgaga tctgatagsc aaggcagcaa tggattttg catgaacatg |
| 1861 aacacaaaag caaacaggaa gaagttggta cgggcactct tcatagttcc tagacaaagg |
| 1921 ttggatttgc taccatttta tgcaagattg gttgctacat tgcatccctg catgtctgat |
| 1981 gtagcagagg atctttgttc catgctgagg ggggatttca gatttcatgt acggaaaaag |
| 2041 gaccagatca acattgaaac aaagaataaa actgttcgtt ttataggaga actaactaag |
| 2101 tttaagatgt tcaccaaaaa tgacacactg cattgtttaa agatgcttct gtcagacttc |
| 2161 tctcatcacc atattgaaat ggcatgcacc ctgctggaga catgtggacg gtttctttc |
| 2221 agatctccag aatctcacct gaggaccagt gtacttttgg agcaaatgat gagaaagaag |
| 2281 caagcaatgc atcttgatgc gagatacgtc acaatggtag agaatgcata ttactactgc |
| 2341 aacccacctc cagctgaaaa aaccgtgaaa aagaaacgtc ctcctctcca ggaatatgtc |
| 2401 cggaaacttt cgcacaaaca tctctctaag gttaccaccg agaaggtttt gagacagatg |
| 2461 cgaaagctgc cctggcagga ccaagaagtg aaagactatg ttatttgttg tatgataaac |
| 2521 atctggaatg tgaaatataa tagtattcat tgtgtagcca acctcttagc aggactagtg |
| 2581 ctctaccaag aggatgttgg gatccacgtt gtggatggag tgttagaaga tattcgatta |
| 2641 ggaatggagg ttaatcaacc taaatttaat cagaggcgca tcagcagtgc caagttctta |
| 2701 ggagaacttt acaattaccg aatggtggaa tcagctgtta ttttcagaac tctgtattct |
| 2761 tttacctcat ttggtgttaa tctgatggc tctccaagtt ccctggaccc acctgagcat |
| 2821 cttttcagaa ttagactcgt atgcactatt ctggacacat gtggccagta ctttgacaga |
| 2881 ggttccagta aacgaaaact tgattgtttc cttgtatatt ttcagcgtta tgtttggtgg |
| 2941 aagaaaagtt tggaggtttg gacaaaagac catccatttc ctattgatat agattacatg |
| 3001 atcagtgata cactagaact gctaagacca aagatcaaac tctgtaattc tctggaagaa |
| 3061 tccatcaggc aggtacaaga cttggaacga gaattcttaa taaaactagg cctagtaaat |
| 3121 gacaaagact caaaagattc tatgacagaa ggagaaaatc ttgaagagga tgaagaagaa |
| 3181 gaagaaggtg gggctgaaac agaagaacaa tctggaaatg aaagtgaagt aaatgagcca |
| 3241 gaagaagagg agggttctga taatgatgat gatgagggag aagaagagga ggaagagaat |
| 3301 acagattacc ttacagattc caataaggaa aatgaaacog atgaagagaa tactgaggta |
| 3361 atgattaaag gcggtggact taagcatgta ccttgtgtag aagatgagga cttcattcaa |
| 3421 gctctggata aaatgatgct agaaaatcta cagcaacgaa gtggtgaatc tgttaaagtg |
| 3481 caccaactag atgtggccat tcctttgcat ctcaaaagcc agctgaggaa agggccccca |
| 3541 ctgggaggtg gggaaggaga ggctgagtct gcagacacaa tgccgtttgt catgttaaca |
| 3601 agaaaaggca ataaacagca gtttaagatc cttaatgtac ccatgtcctc tcaacttgct |
| 3601 gcaaatcact ggaaccagca acaggcagaa caagaagaga ggatgagaat gaagaagctc |
| 3721 acactagata tcaatgaacg gcaagaacaa gaagattatc aagaaatgtt gcagtctctt |

| Sequences |
| --- |
| 3781 gcacagcgcc cagctccagc aaacaccaat cgtgagaggc ggcctcgcta ccaacatccg |
| 3841 aagggagcac ctaatgcaga tctaatcttt aagactggtg ggaggagacg ttga |

(SEQ ID NO: 4)
UPF2 amino acid sequence (GenBank Accession No. AAG60689.1)
```
   1 mpaerkkpas meekdslpnn kekdcserrt vsskerpkdd ikltakkevs kapedkkkrl
  61 eddkrkkedk erkkkdeekv kaeeeskkke eeekkkhqee erkkqeeqak rqqeeeaaaq
 121 mkekeesiql hgeawerhhl rkelrsknqn apdsrpeenf fsrldsslkk ntafvkklkt
 181 iteqqrdsls hdfnglnlsk yiaeavasiv eaklkisdvn cavhlcslfh qryadtapsl
 241 lqvwkkhfea rkeektpnit klrtdlrfia eltivgiftd keglsliyeq lkniinadre
 301 shthvsvvis fcrhcgddia glvprkvksa aekfnlsfpp seiispekgg pfqnllkcyf
 361 tsltkhlkrd hrelqnterq nrrilhskge lsedrhkgye efamsyqkll ansqsladll
 421 denmpalpgd kptpeehgpg idiftpgkpg eydleggiwe dedarnfyen lidlkafvpa
 481 ilfkdneksc qnkesnkddt keakeskenk evsspddlel elenleindd tleleggdea
 541 edltkkllde qeqedeeast gshlklivda flqqlpncvn rdlidkaamd fcmnmntkan
 610 rkklvralfi vprqrldllp fyarlvatlh pcmsdvacdl csmlrgdfrf hvrkkdqini
 661 etknktvrfi geltkfkmft kndtlhclkm llsdfshhhi emactlletc grflfrspes
 721 hlrtsvlleg mmrkkqamhl daryvtmvcn ayyycnpppa ektvkkkrpp lqeyvrklly
 781 kdlskvttek vlrgmrklpw qdqevkdyvi ccminiwnvk ynsihcvanl laglvlyqed
 841 vgihvvdgvl edirlgmevn qpkfnqrris sakflgelyn yrmvesavif rtlysftsfg
 901 vnpdgspssl dppchlfrir lvctildtcg qyfdrgsskr kldcflvyfg ryvwwkksle
 961 vwtkdhpfpi didymisdtl ellrpkiklc nsleesirqv qdlereflik lglvndkask
1021 dsmtegenle edeeeeegga eteeqsgnes evnepeeeeg sdndddegee eeeentdylt
1081 dsnkenedce entevmikgg glkhvpcved edfiqaldkm mlenlqqrsg esvkvhqldv
1141 aiplhlksql rkgpplggge geaesadtmp fvmltrkgnk qqfkilnvpm ssqlaanhwn
1201 qqqaeqeerm rmkkltldin erqeqedyqe mlqslaqrpa pantnrerrp ryqhpkgapn
1261 adlifktggr rr
```

(SEq ID NO: 5)
UPF3 nucleotide sequence (GenBank Accession No. AF318575_1 ) (nt 22-1380)
```
  22                    atgctgtcg gccctagaag tgcagttcca ccgcgactcg
  61 cagcagcagg aggctgagac gccgccaact tcgtcctccg gttgcggggg cggtgcgggc
 121 aaacctcgcg aggagaagag gacggccctg agcaaggtgg tcatccgccg cctgcctccg
 181 ggcctcacca aggagcagct ggaggagcag ctgcgccgc tgccagcaca cgactacttc
 241 gagttcttcg cagccgacct gagtctttat cctcatctct actcaagagc atacattaat
 301 tttaggaatc ctgatgacat ccttcttttt agagatcgtt ttgatggata tatcttcctt
 361 gacagcaaag gcctacaata tcctgcagtg gtagagtttg ctccattcca gaagatagcc
 421 aaaaagaagc tgagaaaaaa agatgccaag actggaagca tcgaagatga tccagaatat
 481 aagaagtttt tagaaaccta ctgtgtggag gaagagaaga ccagtgccaa ccctgagact
 541 ctgctggggg agatggaggc gaagacaaga gagctcattg ctagaagaac cacacctctt
 601 ttggaatata ttaaaaatag aaaattagaa aagcagagaa ttcgagaaga gaagcgagaa
 661 gaacggagga ggagagagtt agaaaagaaa cgtttgcggg aagaggaaaa aagaagaaga
```

| Sequences |
|---|
| 721 agagaagaag aaagatgcaa aaaaaaagag acagataaac agaagaaaat tgcagagaaa |
| 781 gaagtaagga ttaagcttct taagaaacca gaaaagggag aggaaccaac cacagagaaa |
| 841 ccaaaagaaa gaggagagga gattgatact ggaggtggca agcaggaatc ctgtgccccc |
| 901 ggtgcagtcg taaaagccag gcccatggaa ggctcgctgg aggagcccca ggagacgtca |
| 961 cacagcggca gtgataaaga gcacagggat gtggagagat ctcaagaaca agaatctgaa |
| 1021 gcacaaagat accatgtgga tgacggcagg aggcacagag ctcaccacga gcctgaacgg |
| 1081 cttccagaa ggagtgagga tgagcagaga tggggaaag gacctggcca agacagaggg |
| 1141 aagaagggga gccaggacag cggggctccg ggggaggcca tggagagact gggaagagcg |
| 1201 caaggtgtg acgacagtcc agcacccaga aaagagcgac tggcaaacaa ggaccggcca |
| 1261 gccttgcagc tgtatgatcc aggagctcgc ttccgagcgc gagagtgtgg cggaaacagg |
| 1321 aggatctgca aggcagaagg ttcggggact ggtcctgaga gagggaaga ggcagagtga |

(SEQ ID NO: 6)
UPF3 amino acid sequence (GenBank Accession No. AAG60690.1)
```
  1 mlsalevgfh rdsqqqeaet pptsssgcgg gagkpreekr talskvvirr lppgltkeql
 61 eeqlrplpah dyfeffaadl slyphlysra yinfrnpddi llfrdrfdgy ifldskgley
121 pavvefapfq kiakkklrkk daktgsiedd peykkflety cveeektsan pctllgemea
181 ktreliarrt tplleyiknr klekqriree kreerrrrel ekkrlreeek rrrreeerck
241 kketdkgkki aekevrikll kkpekgeept tekpkergee idtgggkges capgavvkar
301 pmegsleepg etshsgsdke hrdversqeq eseaqryhvd dgrrhrahhr perlsrrsed
361 eqrwgkgpgq drgkkgsqds gapgeamerl graqrcddsp aprkerlank drpalqlydp
421 garfrarecg gnrrickaeg sgtgpekree ae
```

(SEQ ID NO: 7)
SMG1 nucleotide sequence (GenBank Accession No. NM_015092.4. nt 364-11349)
| 364 atgagcc gcagagcccc ggggtctcgg ctgagcagcg gcggcggcgg cggoggcacc |
|---|
| 421 aagtatccgc ggagctggaa tgactggcaa cccagaactg atagtgcatc agccgaccca |
| 481 gataatttaa atattcttc atccagagat agaggtggtt cttcctctta tggactgcaa |
| 541 ccttcaaatt cagctgtggt gtctcggcaa aggcacgatg ataccagagt ccacgctgac |
| 601 atacagaatg acgaaaaggg tggctacagt gtcaatggag gatctgggga aaatacttat |
| 661 ggtcggaagt cgttggggca agagctgagg gttaacaatg tgaccagccc tgagttcacc |
| 721 agtgttcagc atggcagtcg tgctttagcc accaaagaca tgaggaaatc acaggagaga |
| 781 tcgatgtctt attctgatga gtctcgactg tcgaatcttc ttcggaggat caccccgggaa |
| 841 gacgacagag accgaagatt ggctactgta aagcagttga agaatttat tcagcaacca |
| 901 gaaaataagc tggtactagt taaacaattg gataatatct ggctgctgt acatgacgtg |
| 961 cttaatgaaa gtagcaaatt gcttcaggag ttgagacagg agggagcttg ctgtcttggc |
| 1021 cttctttgtg cttctctgag ctatgaggct gagaagatct tcaagtggat tttagcaaa |
| 1081 tttagctcat ctgcaaaaga tgaagttaaa ctcctctact tatgtgccac ctacaaagca |
| 1141 ctagagactg taggagaaaa gaaagccttt tcatctgtaa tgcagattgt aatgaccagc |
| 1201 ctgcagtcta ttcttgaaaa tgtggataca ccagaattgc tttgtaaatg tgttaagtgc |
| 1261 attctttgg tggctcgatg ttacccctcat attttcagca ctaattttag ggatacagtt |
| 1321 gatatattag ttggatggca tatagatcat actcagaaac cttcgctcac gcagcaggta |
| 1381 tctgggtggt tgcagagttt ggagccattt tgggtagctg atcttgcatt ttctactact |

| Sequences |
| --- |
| 1441 cttcttggtc agtttctgga agacatggaa gcatatgctg aggacctcag ccatgtggcc |
| 1501 tctggggaat cagtggatga agatgtccct cctccatcag tgtcattacc aaagctggct |
| 1561 gcacttctcc gggtatttag tactgtggtg aggagcattg gggaacgctt cagcccaatt |
| 1621 aggggtcctc caattactga ggcatatgta acagatgttc tgtacagagt aatgagatgt |
| 1681 gtgacggctg caaaccaggt gttttttct gaggctgtgt tgacagctgc taatgagtgt |
| 1741 gttggtgttt tgctaggcag cttggatcct agcatgacta tacattgtga catggtcatt |
| 1801 acatatggat tagaccaact ggagaattgc cagacttgtg gtaccgatta tatcatctca |
| 1861 gtcttgaatt tactcacgct gattgttgaa cagataaata cgaaactgcc atcatcattt |
| 1921 gtagaaaaac tgtttatacc atcatctaaa ctactattct tgcgttatca caaagaaaaa |
| 1981 gaggttgttg ctgtagccca tgctgtttat caagcagtgc tcagcttgaa gaatattcct |
| 2041 gttttggaga ctgcctataa gttaatattg ggagaaatga cttgtgccct aaacaacctc |
| 2101 ctacacagtc tacaacttcc tgaggcctgt tctgaaataa acatgaggc ttttaagaat |
| 2161 catgtgttca atgtagacaa tgcaaaattt gtagttatat ttgacctcag tgccctgact |
| 2221 acaattggaa atgccaaaaa ctcactaata gggatgtggg cgctatctcc aactgtcttt |
| 2281 gcacttctga gtaagaatct gatgattgtg cacagtgacc tggctgttca cttccctgcc |
| 2341 attcagtatg ctgtgctcta cacattgtat tctcattgta ccaggcatga tcactttatc |
| 2401 tctagtagcc tcagttcttc ctctccttct ttgtttgatg gagctgtgat tagcactgta |
| 2461 actacggcta caaagaaaca tttctcaatt atattaaatc ttctgggaat attacttaag |
| 2521 aaagataacc ttaaccagga cacgaggaaa ctgttaatga cttgggcttt ggaagcagct |
| 2581 gttttaatga agaagtctga aacatacgca cctttattct ctcttccgtc tttccataaa |
| 2641 ttttgcaaag gccttttagc caacactctc gttgaagatg tgaatatctg tctgcaggca |
| 2701 tgcagcagtc tacatgctct gtcctcttcc ttgccagatg atctttttaca gagatgtgtc |
| 2761 gatgtttgcc gtgttcaact agtgcacagt ggaactcgta ttcgacaagc atttggaaaa |
| 2821 ctgttgaaat caattccttt agatgttgtc ctaagcaata acaatcacac agaaattcaa |
| 2881 gaaatttctt tagcattaag aagtcacatg agtaaagcac caagtaatac attccacccc |
| 2941 caagatttct ctgatgttat tagtttatt ttgtatggga actctctag aacagggaag |
| 3001 gacaattggt tggaaagact gttctatagc tgccagagac tggataagcg tgaccagtca |
| 3061 acaattccac gcaatctcct gaagacagat gctgtccttt ggcagtgggc catatgggaa |
| 3121 gctgcacaat tcactgttct ttctaagctg agaaccccac tgggcagagc tcaagacacc |
| 3181 ttccagacaa ttgaaggtat cattcgaagt ctcgcagctc acacattaaa ccctgatcag |
| 3241 gatgttagtc agtggacaac tgcagacaat gatgaaggcc atggtaacaa ccaacttaga |
| 3301 cttgttcttc ttctgcagta tctggaaaat ctggagaaat taatgtataa tgcatacgag |
| 3361 ggatgtgcta atgcattaac ttcacctccc aaggtcatta gaacttttt ctataccaat |
| 3421 cgccaaactt gtcaggactg gctaacgcgg attcgactct ccatcatgag ggtaggattg |
| 3481 ttggcaggcc agcctgcagt gacagtgaga catggctttg acttgcttac agagatgaaa |
| 3541 acaaccagcc tatctcaggg gaatgaattg gaagtaacca ttatgatggt ggtagaagca |
| 3601 ttatgtgaac ttcattgtcc tgaagctata cagggaattg ctgtctggtc atcatctatt |
| 3661 gttggaaaaa atcttctgtg gattaactca gtggctcaac aggctgaagg gaggtttgaa |

-continued

| Sequences |
|---|
| 3721 aaggcctctg tggagtacca ggaacacctg tgtgccatga caggcgttga ttgctgcatc |
| 3781 tccagctttg acaaatcggt gctcacctta gccaatgctg ggcgtaacag tgccagcccg |
| 3841 aaacattctc gtaatggtga atccagaaaa actgtgctgt ccaaaccgac tgactcttcc |
| 3901 cctgaggtta taaattattt aggaaataaa gcatgtgagt gctacatctc aattgccgat |
| 3961 tgggctgctg tgcaggaatg gcagaacgct atccatgact gaaaaagag taccagtagc |
| 4021 acttccctca acctgaaagc tgacttcaac tatataaaat cattaagcag ctttgagtct |
| 4081 ggaaaatttg ttgaatgtac cgagcagtta gaattgttac caggagaaaa tatcaatcta |
| 4141 cttgctggag gatcaaaaga aaaaatagac atgaaaaaac tgcttcctaa catgttaagt |
| 4201 ccggatccga gggaacttca gaaatccatt gaagttcaat tgttaagaag ttctgtttgt |
| 4261 ttggcaactg ctttaaaccc gatagaacaa gatcagaagt ggcagtctat aactgaaaat |
| 4321 gtggtaaagt acttgaagca aacatcccgc atcgctattg gacctctgag actttctact |
| 4381 ttaacagttt cacagtcttt gccagttcta agtaccttgc agctgtattg ctcatctgct |
| 4441 ttggagaaca cagtttctaa cagactttca acagaggact gtcttattcc actcttcagt |
| 4501 gaagctttac gttcatgtaa acagcatgac gtgaggccat ggatgcaggc attaaggtat |
| 4561 actatgtacc agaatcagtt gttggagaaa attaagaac aaacagtccc aattagaagc |
| 4621 catctcatgg aattaggtct aacagcagca aaatttgcta gaaaacgagg gaatgtgtcc |
| 4681 cttgcaacaa gactgctggc acagtgcagt gaagttcagc tgggaaagac caccactgca |
| 4741 caggatttag tccaacattt taaaaaacta tcaacccaag gtcaagtgga tgaaaaatgg |
| 4801 gggcccgaac ttgatattga agaaaccaaa ttgctttata cagcaggcca gtcaacacat |
| 4861 gcaatggaaa tgttgagttc ttgtgccata tctttctgca agtctgtgaa agctgaatat |
| 4921 gcagttgcta aatcaattct gacactggct aaatggatcc aggcagaatg gaaagagatt |
| 4981 tcaggacagc tgaaacaggt ttacagagct cagcaccaac agaacttcac aggtctttct |
| 5041 actttgtcta aaaacatact cactctaata gaactgccat ctgttaatac gatggaagaa |
| 5101 gagtatcctc ggatcgagag tgaatctaca gtgcatattg gagttggaga acctgacttc |
| 5161 attttgggac agttgtatca cctgtcttca gtacaggcac ctgaagtagc caaatcttgg |
| 5221 gcagcgttgg ccagctgggc ttataggtgg ggcagaaagg tggttgacaa tgccagtcag |
| 5281 ggagaaggtg ttcgtctgct gcctagagaa aaatctgaag ttcagaatct acttccagac |
| 5341 actataactg aggaagagaa agagagaata tatggtattc ttggacaggg tgtgtgtagg |
| 5401 ccggcgggga ttcaggatga agatataaca cttcagataa ctgagagtga agacaacgaa |
| 5461 gaagatgaca tggttgatgt tatctggcgt cagttgatat caagctgtcc atggctttca |
| 5521 gaacttgatg aaagtgcaac tgaaggagtt attaaagtgt ggaggaaagt tgtagataga |
| 5581 atattcagcc tgtacaaact ctcttgcagt gcatacttta ctttccttaa actcaacgct |
| 5641 ggtcaaattc ctttagatga ggatgaccct aggctgcatt taagtcacag agtggaacag |
| 5701 agcactgatg acatgattgt gatcgccaca ttgcgcctgc tgcggttgct cgtgaagcat |
| 5761 gctggtgagc ttcggcagta tctggagcac ggcttggaga caacacccac tgcaccatgg |
| 5821 agaggaatta ttccgcaact tttctcacgc ttaaaccacc ctgaagtgta tgtgcgccaa |
| 5881 agtatttgta accttctctg ccgtgtggct caagattccc cacatctcat attgtatcct |
| 5941 gcaatagtgg gtaccatatc gcttagtagt gaatcccagg cttcaggaaa taaattttcc |
| 6001 actgcaattc caactttact tggcaatatt caaggagaag aattgctggt ttctgaatgt |

-continued

| Sequences |
|---|
| 6061 gagggaggaa gtcctcctgc atctcaggat agcaataagg atgaacctaa aagtggatta |
| 6121 aatgaagacc aagccatgat gcaggattgt tacagcaaaa ttgtagataa gctgtcctct |
| 6181 gcaaacccca ccatggtatt acaggttcag atgctcgtgg ctgaactgcg cagggtcact |
| 6241 gtgctctggg atgagctctg gctgggagtt ttgctgcaac aacacatgta cgtcctgaga |
| 6301 cgaattcagc agcttgaaga tgaggtgaag agagtccaga caacaacac cttacgcaaa |
| 6361 gaagagaaaa ttgcaatcat gagggagaag cacacagctt tgatgaagcc catcgtattt |
| 6421 gctttggagc atgtgaggag tatcacagcg gctcctgcag aaacacctca tgaaaaatgg |
| 6481 tttcaggata actatggtga tgccattgaa aatgccctag aaaaactgaa gactccattg |
| 6541 aaccctgcaa agctgggag cagctggatt ccatttaaag agataatgct aagtttgcaa |
| 6601 cagagagcac agaaacgtgc aagttacatc ttgcgtcttg aagaaatcag tccatggttg |
| 6661 gctgccatga ctaacactga aattgctctt cctggggaag tctcagccag agacactgtc |
| 6721 acaatccata gtgtgggcgg aaccatcaca atcttaccga ctaaaaccaa gccaaagaaa |
| 6781 cttctctttc ttggatcaga tgggaagagc tatccttatc ttttcaaagg actggaggat |
| 6841 ttacatctgg atgagagaat aatgcagttc ctatctattg tgaataccat gtttgctaca |
| 6901 attaatcgcc aagaaacacc ccggttccat gctcgacact attctgtaac accactagga |
| 6961 acaagatcag gactaatcca gtgggtagat ggagccacac ccttatttgg tctttacaaa |
| 7021 cgatggcaac aacgggaagc tgccttacaa gcacaaaagg cccaagattc ctaccaaact |
| 7081 cctcagaatc ctggaattgt accccgtcct agtgaacttt attacagtaa aattggccct |
| 7141 gctttgaaaa cagttgggct tagcctggat gtgtcccgtc gggattggcc tcttcatgta |
| 7201 atgaaggcag tattggaaga gttaatggag gccacacccc cgaatctcct tgccaaagag |
| 7261 ctctggtcat cttgcacaac acctgatgaa tggtggagag ttacgcagtc ttatgcaaga |
| 7321 tctactgcag tcatgtctat ggttggatac ataattggcc ttggagacag acatctggat |
| 7381 aatgttctta tagatatgac gactggagaa gttgttcaca tagattacaa tgtttgcttt |
| 7441 gaaaaaggta aaagccttag agttcctgag aaagtacctt ttcgaatgac acaaaacatt |
| 7501 gaaacagcac tgggtgtaac tggagtagaa ggtgtatttta ggctttcatg tgagcaggtt |
| 7561 ttacacatta tgcggcgtgg cagagagacc ctgctgacgc tgctggaggc ctttgtgtac |
| 7621 gaccctctgg tggactggac agcaggaggc gaggctgggt ttgctggtgc tgtctatggt |
| 7681 ggaggtggcc agcaggccga gagcaagcag agcaagagag atgggagcg agagatcacc |
| 7741 cgcagcctgt tttcttctag agtagctgag attaaggtga actggtttaa gaatagagat |
| 7801 gagatactgg ttgtgcttcc caagttggac ggtagcttag atgaatacct aagcttgcaa |
| 7861 gagcaactga cagatgtgga aaaactgcag ggcaaactac tggaggaaat agagtttcta |
| 7921 gaaggagctg aaggggtgga tcatccttct catactctgc aacacaggta ttctgagcac |
| 7981 acccaactac agaatcagca aagagctgtt caggaagcaa tccaggtgaa gctgaatgaa |
| 8041 tttgaacaat ggataacaca ttatcaggct gcattcaata atttagaagc aacacagctt |
| 8101 gcaagcttgc ctcaagagat aagcacacaa atggaacttc gtcctccaag ttacgtgcca |
| 8161 gcaacagcct tctgcagaa tgctggtcag gcccacttga ttagccagtg cgagcagctg |
| 8221 gagggggagg ttggtgctct cctgcagcag aggcgctccg tgctccgtgg ctgtctggag |
| 8281 caactgcatc actatgcaac cgtggccctg cagtatccga aggccatatt tcagaaacat |

-continued

| Sequences |
|---|
| 8341 cgaattgaac agtggaagac ctggatggaa gagctcatct gtaacaccac agtagagcgt |
| 8401 tgtcaagagc tctataggaa atatgaaatg caatatgctc cccagccacc cccaacagtg |
| 8461 tgtcagttca tcactgccac tgaaatgacc ctgcagcgat acgcagcaga catcaacagc |
| 8521 agacttatta gacaagtgga acgcttgaaa caggaagctg tcactgtgcc agtttgtgaa |
| 8581 gatcagttga agaaattga acgttgcatt aaagttttcc ttcatgagaa tggagaagaa |
| 8641 ggatctttga gtctagcaag tgttattatt tctgcccttt gtacccttac aaggcgtaac |
| 8701 ctgatgatgg aaggtgcagc gtcaagtgct ggagaacagc tggttgatct gacttctcgg |
| 8761 gatggagcct ggttcttgga ggaactctgc agtatgagcg aaacgtcac ctgcttggtt |
| 8821 cagttactga agcagcgcca cctggtgcca caggacttag atatcccgaa ccccatggaa |
| 8881 gcgtctgaga cagttcactt agccaatgga gtgtatacct cacttcagga attgaattcg |
| 8941 aatttccggc aaatcatatt tccagaagca cttcgatgtt aatgaaagg ggaatacacg |
| 9001 ttagaaagta tgctgcatga actggacggt cttattgagc agaccaccga tggcgttccc |
| 9061 ctgcagactc tagtggaatc tcttcaggcc tacttaagaa acgcagctat gggactggaa |
| 9121 gaagaaacac atgctcatta catcgatgtt gccagactac tacatgctca gtacggtgaa |
| 9181 ttaatccaac cgagaaatgg ttcagttgat gaaacaccca aaatgtcagc tggccagatg |
| 9241 cttttggtag cattcgatgg catgtttgct caagttgaaa ctgctttcag cttattagtt |
| 9301 gaaaagttga caagatgga aattcccata gcttggcgaa agattgacat cataagggaa |
| 9361 gccaggagta ctcaagttaa tttttttgat gatgataatc accggcaggt gctagaagag |
| 9421 attttctttc taaaaagact acagactatt aaggagttct toaggctctg tggtaccttt |
| 9481 tctaaaacat tgtcaggatc aagttcactt gaagatcaga atactgtgaa tgggcctgta |
| 9541 cagattgtca atgtgaaaac cctttttaga aactottgtt tcagtgaaga ccaaatggcc |
| 9601 aaacctatca aggcattcac agctgacttt gtgaggcagc tattgatagg gctacccaac |
| 9661 caagccctcg gactcacacc gtgcagtttt accactactc tgggtgtaga catcattgct |
| 9721 caagtagagg caaaggactt tggtgccgaa agcaaagttt ctgttgatga tctctgtaag |
| 9781 aaagcggtgg aacataacat ccagataggg aagttctctc agctggttat gaacasgggc |
| 9841 actgtgttag caagttctta cgacactgcc tggaagaagc atgacttggt gcgaaggcta |
| 9901 gaaaccagta tttcttcttg taagacaagc ctgcagcggg ttcagctgca tattgccatg |
| 9961 tttcagtggc aacatgaaga tctacttatc aatagaccac aagccatgtc agtcacacct |
| 10021 cccccacggt ctgctatoct aaccagcacg aaaaagaagc tgcataccct gagccagatt |
| 10081 gaaacttcta ttgcaacagt tcaggagaag ctagctgcac ttgaatcaag tattgaacag |
| 10141 cgactcaagt gggcaggtgg tgccaaccct gcattggccc ctgtactaca agattttgaa |
| 10201 gcaacgatag ctgaaagaag aaatcttgtc cttaaagaga gccaaagagc aagtcaggtc |
| 10261 acatttctct gcagcaatat cattcatttt gasagtttac gaacaagaac tgcagaagcc |
| 10321 ttaaacctgg atgcggcgtt atttgaacta atcaagcgat gtcagcagat gtgttcgttt |
| 10381 gcatcacagt ttaacagttc agtgtctgag ttagagcttc gtttattaca gagagtggac |
| 10441 actggtcttg aacatcctat tggcagctct gaatggcttt tgtcagcaca caaacagttg |
| 10501 acccaggata tgtctactca gagggcaatt cagacagaga aagagcagca gatagaaacg |
| 10561 gtctgtgaaa caattcagaa totggttgat aatataaaga ctgtgctcac tggtcataac |
| 10621 cgacagcttg gagatgtcaa acatctctcg aaagctatgg ctaaggatga agaagctgct |

| Sequences |
|---|
| 10681 ctggcagatg gtgaagatgt tccctatgag aacagtgtta ggcagttttt gggtgaatat |
| 10741 aaatcatggc aagacaacat tcaaacagtt ctatttacat tagtccaggc tatgggtcag |
| 10801 gttcgaagtc aagaacacgt tgaaatgctc caggaaatca ctcccacctt gaaagaactg |
| 10861 aaaacacaaa gtcagagtat ctataataat ttagtgagtt ttgcatcacc cttagtcacc |
| 10921 gatgcaacaa atgaatgttc gagtccaacg tcatctgcta cttatcagcc atccttcgct |
| 10981 gcagcagtcc ggagtaacac tggccagaag actcagcctg atgtcatgtc acagaatgct |
| 11041 agaaagctga tccagaaaaa tcttgctaca tcagctgata ctccaccaag caccgttcca |
| 11101 ggaactggca agagtgttgo ttgtagtcct aaaaaggcag ccagagaccc taaaactggg |
| 11161 aaagcggtgc aagagagaaa ctccctatgca gtgagtgtgt ggaagagagt gaaagccaag |
| 11221 ttagagggcc gagatgttga tccgaatagg aggatgtcag ttgctgaaca ggttgactat |
| 11281 gtcattaagg aagcaactaa tctagataac ttggctcagc tgtatgaagg ttggacagcc |
| 11341 tgggtgtga |

(SEQ ID NO: 8)
SMG1 amino acid sequence (GenBank Accession No. NP_055907.3)

```
   1 msrrapgsrl ssgggggtk yprswndwqp rtdsasadpd nlkysssrdr ggsssyglqp
  61 snsavvsrgr hddtrvhadi qndekggysv nggsgentyg rkslgqelrv nnvtspefts
 121 vqhgsralat kdmrksqers msysdesrls nllrritred drdrrlatvk qlkefiqqpe
 181 nklvlvkqld nilaavhdvl nesskllqel rqegacclgl lcaslsyeae kifkwifskf
 241 sssakdevkl lylcatykal etvgekkafs svmqlvmtsl qsilenvdtp ellckcvkci
 301 llvarcyphi fstnfrdtvd ilvgwhidht qkpsltqqvs gwlqslepfw vadlafsttl
 361 lgqfledmea yaedlshvas gesvdedvpp psvslpklaa llrvfstvvr sigerfspir
 421 gppiteayvt dvlyrvmrcv taangvffsc avltaanfcv gvllgsldps mtihcdmvit
 481 ygldglcncq tcgtdyiisv lnlltliveq intklpssfv eklfipsskl lflryhkeke
 541 vvavahavyq avlslknipv letayklilg emtcalnnll hslqlpeacs eikheafknh
 601 vfnvdnakfv vifdlsaltt ignaknslig mwalsptvfa llsknlmivh sdlavhfpai
 661 qyavlytlys hctrhdhfis sslsssspsl fdgavistvt tatkkhfsii lnllgillkk
 721 dnlnqdtrkl lmtwalcaav lmkksetyap lfslpsfhkf ckgllantlv edvniclqac
 781 sslhalsssl pddllqrcvd vcrvqlvhsg trirqafgkl lksipldvvl snnnhtqiqe
 841 islalrshms kapsntfhpq dfsdvisfil ygnshrtgkd nwlerlfysc qrldkrdqst
 901 iprnllktda vlwqwaiwea aqftvlsklr tplgraqdtf qtiegiirsl aahtlnpdqd
 961 vsgwttadnd eghgnnqlrl vlllqylenl eklmynayeg canaltsppk virtffytnr
1021 qtcqdwltri rlsimrvgll agqpavtvrh gfdlltemkt tslsqgnele vtimmvveal
1081 celhcpeaig giavwsssiv gknllwinsv aqgaegrfck asvetqehlc amtgvdccis
1141 sfdksvltla nagrnsaspk hslngearkt vlskptdssp evinylgnka cecyisiadw
1201 aavqewqnai hdlkkststt slnlkadfny ikslssfcsg kfvectcglc llpgeninll
1261 aggskckidm kkllpnmlsp dprelqksie vqllrssvcl atalnpieqd gkwqsitenv
1321 vkylkqtsri aigplrlstl tvsqslpvls tlqlycssal entvsnrlst edcliplfse
1381 alrsckghdv rpwmgalryt mygngllekl kcgtvpirsh lmelgltaak farkrgnvsl
1441 atrllagcse vglgktttaq dlvghfkkls tqgqvdekwg peldiektkl lytagqstha
1501 memlsscais fcksvkaeya vaksiltlak wiqaewkeis gqlkqvyraq hqqnftglst
```

-continued

| Sequences |
| --- |

```
1561 lskniltlie lpsvntmeee ypriesestv higvgepdfi lgqlyhlssv qapevakswa 1621 alaswayrwg rkvvdnasqg egvrllprek sevqnllpdt iteeekeriy gilgqavcrp 1681 agiqdeditl qitesednee ddmvdviwrg lisscpwlse ldesategvi kvwrkvvdri 1741 fslyklscsa yftflklnag qipldeddpr lhlshrveqs tddmiviatl rllrllvkha 1801 gelrgylehg lettptapwr giipqlfsrl nhpevyvrqs icnllcrvaq dsphlilypa 1861 ivgtislssc sgasgnkfst aiptllgniq geellvsece ggsppasqds nkdepksgln 1921 edqammgdcy skivdklssa nptmvlqvqm lvaelrrvtv lwdelwlgvl lqqhmyvlrr 1981 iqqledevkr vqnnntlrke ekiaimrckh talmkpivfa lehvrsitaa paetphekwf 2041 qdnygdaien aleklktpln pakpgsswip fkeimlslgq raqkrasyil rleeispwla 2101 amtnteialp gevsardtvt ihsvggtiti lptktkpkkl lflgsdgksy pylfkgledl 2161 hldcrimgfl sivntmfati nrqetprfha rhysvtplgt rsgliqwvdg atpltglykr 2221 wqqreaalqa gkagdsyqtp qnpgivprps elyyskigpa lktvglsldv srrdwplhvm 2281 kavleelmea tppnllakel wsscttpdcw wrvtqsyars tavmsmvgyi iglgdrhldn 2341 vlidmttgev vhidynvcfe kgkslrvpek vpfrmtqnie talgvtgvcg vfrlsceqvl 2401 himrrgretl ltllcafvyd plvdwtaggc agfagavygg ggqgaeskqs kremereitr 2461 slfssrvaei kvnwfknrde mlvvlpkldg sldeylslqe qltdvekleg kllleeiefle 2521 gaegvdhpsh tlqhryseht qlqtgqravq eaiqvklnef eqwithyqaa fnnleatqla 2581 sllqeistqm dlgppsyvpa taflqnagqa hlisqceqle ecvgallqqr rsvlrgcleg 2641 lhhyatvalq ypkaifgkhr ieqwktwmee licnttverc qelyrkyemq yaqgppptve 2701 qfitatemtl qryaadinsr lirqvcrlkq eavtvpvced qlkeiercik vflhengeeg 2761 slslasviis alctltrrnl mmegaassag eqlvdltsrd gawfleelcs msgnvtclvg 2821 llkqchlvpq dldipnpmea setvhlangv ytslqelnsn frqiifpeal rclmkgeytl 2881 esmlheldgl ieqttdgvpl qtlveslqay lrnaamglee ethahyidva rllhaqygel 2941 iqprngsvde tpkmsagqml lvafdgmfaq vetafsllve klnkmeipia wrkidiirea 3001 rstgvnffdd dnhrgvleei fflkrlqtik effrlcgtfs ktlsgsssle dqntvngpvq 3061 ivnvktlfrn scfsedqmak pikaftadfv rqlliglpnq algltlosfi salgvdiiaq 3121 veakdfgaes kvsvddlckk avehnigigk fsglvmnrat vlassydtaw kkhdivrrle 3181 tsisscktsl qrvqlhiamf qwqhedllin rpqamsvtpp prsailtsmk kklhtlsgie 3241 tsiatvqwkl aalessieqr lkwagganpa lapvlqdfea tiaerrnlvl kesqrasgvt 3301 flcsniihfe slrtrtaeal nldaalfeli krcqqmcsfa sqfnssvsel elrllqrvdt 3361 glehpigsse wllsahkqlt qdmstgraiq tekeqqietv cetiqnlvdn iktvllghnr 3421 qlgdvkhllk amakdeeaal adgedvpyen svrqflgeyk swqdniqtvl ftlqamgqv 3481 rsqehvemlq eitptlkelk tqsqsiynnl vsfasplvtd atnecsspts satyqpsfaa 3541 avrsntgqkt qpdvmsqnar kliqknlats adtppstvpg tgksvacspk kavrdpktgk 3601 avqernsyav svwkrvkakl egrdvdpnrr msvaeqvdyv ikeatnldnl aqlyegwtaw 3661 v
```

-continued

| Sequences |
|---|

(SEQ ID NO: 9)
SMG5 nucleotide sequence (GenBank Accession No. NM_015327.2, nt 150-3200)

```
 150                                          a tgagccaagg ccccccaca ggggagagca
 181 gcgagcccga agcaaaagtc ctccacacta agcggcttta ccgggctgtg gtgaggctg
 241 tgcatcgact tgacctcatc ctttgcaaca aaactgctta tcaagaagta ttcaaaccag
 301 aaaacattag cctgaggaac aagctgcgtg agctctgogt caagcttatg ttcctgcacc
 361 cagtggacta tgggagaaag gctgaggagc tgctgtggag aaaggtatac tatgaagtta
 421 tccagcttat caagactaac aaaaagcaca tccacagccg agcactttg aatgtgcct
 481 acaggacgca cctggttgct ggtattggct tctaccagca tctccttctc tatatccagt
 541 cccactacca gctggaactg cagtgctgca tcgactggac ccatgtcact gaccccctca
 601 taggatgcaa gaagccagtg tctgcctcag ggaaggagat ggattgggca cagatggcat
 661 gtcaccgatg tctggtgtat ctggaggatt tgtcccgata tcagaatgaa ttagctggcg
 721 tagatacca gctgctagcc gagagatttt actaccaagc cctgtcagta gctcctcaga
 781 ttggaatgcc cttcaatcag ctgggcaccc tggcaggcag caagtactat aatgtggaag
 841 ccatgtattg ctacctgcgc tgcatccagt cagaagtgtc ctttgaggga gcctatggga
 901 acctcaagcg gctgtatgac aaggcagcca aaatgtacca ccaactgaag aagtgtgaga
 961 ctcggaaact gtctcctggc aaaaagcgat gtaaagacat taaaaggttg ctagtgaact
1021 ttatgtatct gcaaagcctc ctacagccca aaagccaggt cgtggactca gagctgacct
1081 cactttgcca gtcagtcctg gaggacttca acctctgcct cttctacctg ccctcctcac
1141 ccaacctcag cctggccagt gaggatgagg aggagtatga gagtggatat gctttcctcc
1201 cggaccttct catctttcaa atggtcatca tctgccttat gtgtgtgcac agcttggaga
1261 gagcaggatc caagcagtac agtgcagcca ttgccttcac cctggccctc ttttcccacc
1321 tcgtcaatca tgtcaacata cggctgcagg ctgagctgga agagggcgag aatcccgtcc
1381 cggcattcca gagtgatggc acagatgaac cagagtccaa ggaacctgtg gagaaagagg
1441 aggagccaga tcctgagcct cctcctgtaa caccccaagt gggtgagggc agaaagagcc
1501 gtaagttctc tcgcctctcc tgtctccgcc gtcgccgcca cccacccaaa gttggtgatg
1561 acagtgacct gagtgaaggc tttgaatcgg actcaagcca tgactcagcc cgggccagtg
1621 agggctcaga cagtggctct gacaagagtc ttgaaggtgg gggaacggcc tttgatgctg
1681 aaacagactc ggaaatgaat agccaggagt cccgatcaga cttggaagat atgaggaag
1741 aggagggac acggtcacca accctggagc cccctcgggg cagatcagag gctcccgatt
1801 ccctcaatgg cccactgggc cccagtgagg ctagcattgc cagcaatcta caagccatgt
1861 ccacccagat gttccagact aagcgctgct tccgactggc cccacccttt agcaacctgc
1921 tcctccagcc caccaccaac cctcatacct cggccagcca caggccttgc gtcaatgggg
1981 atgtagacaa gccttcagag ccagcctctg aggagggctc tgagtcggag gggagtgagt
2041 ccagtggacg ctcctgtcgg aatgagcgca gcatccagga gaagcttcag gtcctgatgg
2101 ccgaaggtct gcttcctgct gtgaaagtct tcctggactg gcttcggacc aaccccgacc
2161 tcatcatcgt gtgtgcgcag agctctcaaa gtctgtggaa ccgcctgtct gtgttgctga
2221 atctgttgcc tgctgctggt gaactccagg agtctggcct ggccttgtgt cctgaggtcc
2281 aagatcttct tgaaggttgt gaactgcctg acctccctc tagccttctg ctcccagagg
```

| Sequences |
|---|
| 2341 acatggøtct tcgtaacctg cccccgctcc gagctgccca cagacgcttt aactttgaca |
| 2401 cggatcggcc cctgctcagc accttagagg agtcagtggt gcgcatctgc tgcatccgca |
| 2461 gctttggtca tttcatcgcc cgcctgcaag gcagcatcct gcagttcaac ccagaggttg |
| 2521 gcatcttcgt cagcattgcc cagtctgagc aggagagcct gctgcagcag gcccaggcac |
| 2581 agttccgaat ggcacaggag gaagctcgtc ggaacaggct catgagagac atggctcagc |
| 2641 tacgacttca gctcgaagtg tctcagctgg agggcagcct gcagcagccc aaggcccagt |
| 2701 cagccatgtc tccctacctc gtccctgaca cccaggccct ctgccaccat ctccctgtca |
| 2761 tccgccaact ggccaccagt ggccgcttca ttgtcatcat cccaaggaca gtgatcgatg |
| 2821 gcctagattt gctgaagaag gaacacccag gggcccggga tgggattcgg tacctggagg |
| 2881 cagagtttaa aaaggaaac aggtacattc gctgccagaa agaggtggga aagagctttg |
| 2941 agcggcataa gctgaagagg caggatgcag atgcctggac tctctataag atcctagaca |
| 3001 gctgcaaaca gctgactctg gcccaggggg caggtgagga ggatccgagt ggcatggtga |
| 3061 ccatcatcac aggccttcca ctggacaacc ccagcgtgct ttcaggcccc atgcaggcag |
| 3121 ccctgcaggc cactgcccac gccagtgtgg acatcaagaa tgttctcgac ttctacaagc |
| 3181 agtggaagga aattggttga |

(SEQ ID NO: 10)
SMG5 amino acid sequence (GenBank Accession No. NP_056142.2)
```
  1 msqgpptges sepeakvlht krlyravvea vhrldlilcn ktayqevfkp enislrklr
 61 elcvklmflh pvdygrkaee llwrkvyyev iqliktnkkh ihsrstleca yrthlvagig
121 fyghlllyig shyglelqcc idwthvtdpl igckkpvsas gkemdwaqma chrcivylgd
181 lsryqnelag vdtellaerf yygalsvapq igmpfnqlgt lagskyynve amycylrciq
241 sevsfegayg nlkrlydkaa kmyhqlkkce trklspokkr ckdikrllvn fmylqsllqp
301 ksssvdselt slcqsvledf nlclfylpss pnlslasede eeyesgyafl pdllifqmvi
361 iclmovhsle ragskqysaa iaftlalfsh lvnhvnirlq aeleegenpv pafqsdgtde
421 pcskcpvckc eepdpcpppv tpgvgegrks rkfsrlsclr rrhppkvgd dsdlsegfes
481 dsshdsaras egsdsgsdks legggtafda etdsemnsqe srsdledmee eegtrsptle
541 pprgrseapd slngplgpse asiasnlgam stqmfqtkrc frlaptfsnl llqpttnpht
601 sashrpcvng dvdkpsepas eegsesegse ssgrscrner siqeklqvlm aegllpavkv
661 fldwlrtnpd liivcaqssq slwnrlsvll nllpaagclq esglalcpev qdllegcelp
721 dlpsslllpe dmalrnlppl raahrrfnfd tdrpllstle esvvriccir sfghfiarlq
781 gsilqfnpev gifvsiaqse qesllqqaqa qfrmaqeear rnrlmrdmaq lrlqlevsql
841 egslqqpkaq samspylvpd tqalchhlpv irqlatsgrf iviiprtvid gldllkkehp
901 gardgiryle aefkkgnryi rcqkevgksf erhklkrqda dawtlykild sckgltlaqg
961 ageedpsgmv tiitglpldn psvlsgpmqa alqaaahasv diknvldfyk qwkeig
```

(SEQ ID NO: 11)
SMG6 nucleotide sequence (GenBank Accession No. BC064916.1, nt 296-1831)

| |
|---|
| 296                                                                 atgga |
| 301 gacattccct gcagtggctg agaaggtcct caaggagttc aggtgttac tgcagcacag |
| 361 cccctctccc attggaagta cccgcatgct gcagcttatg accatcaata tgtttgcagt |
| 421 acacaactcc cagctgaaag actgcttctc ggaggagtgc cgctctgtga tccaggaaca |
| 481 agccgcagct ctgggcttgg ccatgttttc tctactggtc cgccgctgca cctgcttact |

-continued

| Sequences |
|---|

```
 541 taaggagtcc gccaaagctc agctgtcctc tcctgaggac caggatgacc aagacgacat
 601 caaggtgtct tcctttgtcc cggacctgaa ggagctgctc cccagtgtca agtctggtc
 661 agattggatg ctcggctacc cggacacctg gaatcctcct cccacatccc tggatctgcc
 721 ctcgcatgtt gctgtggatg tatggtcgac gctggctgat ttctgtaaca tactgactgc
 781 agtgaatcag tctgaggtgc cactgtacaa ggacccggat gatgacctca cccttcttat
 841 cctggaagag gatcggcttc tctcgggctt tgtccccttg ctggctgccc ctcaggaccc
 901 ctgctacgtg gagaaaacct cggataaggt tattgcagct gactgcaaaa gggtcacagt
 961 gctgaagtat tttctggaag ccctttgtgg acaagaagag cctctgctgg cattcaaggg
1021 tggaaagtat gtgtcagtgg cacccgtccc agacaccatg ggaaaggaaa tgggaagcca
1081 agagggaaca cgactggaag atgaggagga ggatgtggtg attgaagact tgaggaaga
1141 ttcagaggct gaaggcagcg gaggcgagga tgacatcagg agcttcggg ccaagaagct
1201 ggctctggcc aggaagatag ctgagcagca gcgtcgccag gaaaagatcc aggctgtcct
1261 ggaggaccac agtcagatga ggcagatgga gctcgaaatc agaccttttgt tcctcgtacc
1321 agacaccaac ggcttcattg accacctggc cagtctggcg cggctgctgg agagcaggaa
1381 gtacatcctg gtggtgcccc tcatcgtgat caatgagctg gacggcctgc ccaaggggca
1441 ggagacagac caccgggctg ggggctacgc ccgtgtggta caagagaagg cccgcaagtc
1501 catcgagttc ctcgagcagc gattcgagag tcgggactct tgcctgcgag ccctgaccag
1561 ccgtggcaat gaactcgaat ccatcgcctt ccgcagtgag gacatcactg gccagctggg
1621 taacaacgat gatctcatcc tgtcctgctg cctccactac tgcaaagaca aggctaagga
1681 cttcatgccc gccagcaaag aggagccaat ccggctactc cgggaggtgg tgctgttgac
1741 ggatgaccgg aacctgcgtg tgaaggcgct cacaaggaat gttcctgtac gggacatccc
1801 agccttcctc acgtgggccc aggtgggctg a
```

(SEQ ID NO: 12)
SMG6 amino acid sequence (GenBank Accession No. AAH64916.1)

```
   1 metfpavaek vlkefqvllq hspspigstr mlqlmtinmf avhnsqlkdc fseecrsviq
  61 eqaaalglam fsllvrrctc llkcsakagl sspedqddqd dikvssfvpd lkellpsvkv
 121 wsdwmlgypd twnppptsld lpshvavdvw stladfcnil tavnqsevpl ykdpdddltl
 181 lileedrlls gfvpllaapq dpcyvektsd kviaadckrv tvlkyfleal cgqeepllaf
 241 kggkyvsvap vpdtmgkcmg sqegtrlede eedvviedfc edseaegsgg eddirelrak
 301 klalarkiae qqrrqekiqa vledhsqmrq meleirplfl vpdtngfidh laslarlles
 361 rkyilvvpli vineldglak gqetdhragg yarvvqekar ksiefleqrf esrdsclral
 411 tsrgnelesi afrseditgq lgnnddlils cclhyckdka kdfmpaskee pirllrevvl
 481 ltddrnlrvk altrnvpvrd ipafltwagv g
```

(SEQ ID NO: 13)
SMG7 nucleotide sequence (GenBank Accession No. BC036381.1, nt 119-3655)

```
 119                                                                   at
 121 gagcctgcag agcgcgcagt acctccggca ggcagaagtc ctgaaggctg acatgacaga
 181 ttctaagctg ggtccagctg aagtctggac atccaggcag gctctgcagg acctgtacca
 241 gaaaatgcta gttaccgatt tggaatacgc tttagacaag aaagtagaac aggatctctg
 301 gaatcacgcc tttaagaatc agatcacaac actacaaggc caggcaaaga atcgagcaaa
```

-continued

| | Sequences |
|---|---|
| 361 | tccgaatcgg agtgaagttc aggcaaacct ttctctgttc ctagaggcag ctagtggctt |
| 421 | ctatactcag ttattacaag aactgtgtac agtatttaat gtagatttac catgccgtgt |
| 481 | gaagtcttcc caattgggaa ttatcagcaa taaacagacg cataccagcg ccatagtgaa |
| 541 | gccacagtct agctcctgtt cctatatctg ccagcactgc ctgtccacc ttgcagacat |
| 601 | tgctcgatac agaaaccaga ccagccaggc agagtcctac tataggcatg cagctcagct |
| 661 | tgtcccctcc aatggtcagc cttataatca gttggctatc ttagcttctt ccaaaggaga |
| 721 | ccatctgacc acaatttct actactgcag aagcattgct gtgaagttcc ctttcccagc |
| 781 | tgcctccact aatctgcaaa aagcactttc taaagcactc gaaagccgag atgaggtgaa |
| 841 | aaccaagtgg ggtgtttctg acttcatcaa ggcctttatt aaattccacg tcatgtgta |
| 901 | cctgagtaag agcttggaaa agttgagccc tcttcgagac aaattggaag aacagtttaa |
| 961 | gaggctgcta ttccaaaaag ctttcaactc tcagcagtta gttcatgtca ctgtcattaa |
| 1021 | cctgtttcaa cttcatcacc ttcgtgactt tagcaatgaa accgagcagc acacttatag |
| 1081 | ccaagatgag cagctatgtt ggacacagtt gctggccctc tttatgtctt ttctcggcat |
| 1141 | cctgtgcaag tgtcctctac agaatgagtc tcaggaggag tcctacaatg cctatcctct |
| 1201 | tccagcagtc aaggtctcca tggactggct aagactcaga cccagggtct ttcaggaggc |
| 1261 | agtggtggat gaaagacagt acatttggcc ctggttgatt tctcttctga atagtttcca |
| 1321 | tccccatgaa gaggacctct caagtattag tgcgacacca cttccagagg agtttgaatt |
| 1381 | acaaggattt ttggcattga gaccttcttt caggaacttg gatttttcca aaggtcacca |
| 1441 | gggtattaca ggggacaaag aaggccagca acgacgaata cgacagcaac gcttgatctc |
| 1501 | tataggcaaa tggattgctg ataatcagcc aaggctgatt cagtgtgaaa atgaggtagg |
| 1561 | gaaattgttg tttatcacag aaatcccaga attaatactg gaagaccca gtgaagccaa |
| 1621 | agagaaccctc attctgcaag aaacatctgt gatagagtcg ctggctgcag atgggagccc |
| 1681 | agggctaaaa tcagtgctat ctacaagccg aaatttaagc aacaactgtg acacaggaga |
| 1741 | gaagccagtg gttaccttca agaaaacat taagacacga gaagtgaaca gagaccaagg |
| 1801 | aagaagtttt cctcccaaag aggtaaaatc ccagacagaa ctaagaaaga ctccagtgtc |
| 1861 | tgaagccaga aaaacacctg taactcaaac cccaacacaa gcaagtaact cccagttcat |
| 1921 | ccccattcat caccctggag ccttccctcc tcttcccagc aggccagggt ttccgccccc |
| 1581 | aacatatgtt atccccccgc ctgtggcatt ttctatgggc tcaggttaca ccttcccagc |
| 2041 | tggtgtttct gtcccaggaa cctttcttca gcctacagct cactctcaag caggaaacca |
| 2101 | ggtgcaagct gggaaacagt cccacattcc ttacagccag caacggcccc ctggaccagg |
| 2161 | gccaatgaac cagggacctc aacaatcaca gccaccttcc cagcaacccc ttacatcttt |
| 2221 | accagctcag ccaacagcac agtctacaag ccagctgcag gttcaagctc taactcagca |
| 2281 | acaacaatcc cctacaaaag ctgtgccggc tttggggaaa agcccgcctc accactctgg |
| 2341 | attccagcag tatcaacagg cagatgcctc caaacagctg tggaatcccc ctcaggttca |
| 2401 | aggcccatta gggaaaatta tgcctgtgaa acagcoctac taccttcaga cccaagaccc |
| 2461 | cataaaactg tttgagccgt cattgcaacc tcctgtaatg cagcagcagc ctctagaaaa |
| 2521 | aaaaatgaag cctttttccca tggagccata taaccataat ccctcagaag tcaaggtccc |
| 2581 | agaattctac tgggattctt cctacagcat ggctgataac agatctgtaa tggcacagca |
| 2641 | agcaaacata gaccgcaggg gcaaacggtc accaggaatc ttccgtccag agcaggatcc |

-continued

| Sequences |
|---|

```
2701 tgtacccaga atgccgtttg aggaccccaa gagctcccct ctgcttcctc cggacctgtt 2761 aaagagtctg gctgccttgg aggaagagga agagctgatt ttttctaaca ctcctgatct 2821 ttacccggct ctgctggggc ctctcgcctc tcttcctgga cgaagccttt ttaaatcctt 2881 attggagaag ccctcagagc tcatgtcaca ttcatcctct ttcctgtccc tcaccggatt 2841 ctctctcaat caggaaagat acccaaataa tagtatgttc aatgaggtat atgggaaaaa 3001 cctgacatcc agctccaaag cagaactcag tccctcaatg gccccccagg aaacatctct 3061 gtattccctt tttgaaggga ctcgtggtc tcatcactt cctgccagtt cagatcattc 3121 aacaccagcc agccagtctc ctcattcctc taacccaagc agcctaccca gctctcctcc 3181 aacacacaac cataattctg ttccattctc caattttgga cccattggga ctcagataa 3241 cagggataga aggactgcag atcggtggaa aactgataag ccagccatgg gtgggtttgg 3301 cattgattat ctctcagcaa cgtcatcctc tgagagcagt tggcatcagg ccagcactcc 3361 gagtggcacc tggacaggcc atggcccttc catggaggat tcctctgctg tcctcatgga 3421 aagcctaaag aagcaacagc atggggtcca gcagttgggg cccaaaagac agtctgaaga 3481 ggaaggaagc agcagtatct gcgtagccca cagagggccc aggcccctgc ccagctgcag 3541 tctcccagcc tccactttca gagtgaaatt caaggcagca cggacatgtg cccatcaggc 3601 acagaagaaa acgacgtc gtccattttg aagagacga aagaaggaa ataa
```

(SEQ ID NO: 14)

SMG7 amino acid sequence (GenBank Accession No. AAH36381.1)

```
   1 mslgsagylr gaevlkadmt dsklgpaevw tsrqalqdly gkmlvtdley aldkkveqdl 61 wnhafknqit tlqggaknra npnrsevqan lslfleaasg fytqllqelc tvfnvdlpcr 121 vkssqlgiis nkgthtsaiv kpqssscsyi cqhclvhlgd iaryrnqtsq aesyyrhaaq 181 lvpsngqpyn glailasskg dhlttifyyc rsiavkfpfp aastnlqkal skalesrdev 241 ktkwgvsdfi kafikfhghv ylskslckls plrekleeqf krllfqkafn sqqlvhvtvi 301 nlfqlhhlrd fsneteqhty sqdeqlcwtq llalfmsflg ilckcplqnc sqeesynayp 361 lpavkysmdw lrlrprvfqc avvdergyiw pwlisllnsf hpheedlssi satplpeefe 421 lggflalrps frnldfskgh qgitgdkcgq qrrirqqrli sigkwiadnq prliqcenev 481 gkllfiteip eliledpsea kenlilqets vieslaadgs pglksvlsts rnlsnncdtg 541 ekpvvtfken iktrevnrdg grsfppkcvk sqtelrktpv searktpvtq tptqasnsqf 601 ipihhpgafp plpsrpgfpp ptyvipppva fsmgsgytfp agvsvpqtfl qptahspagn 661 qvqagkqshi pysqqrpsgp gpmnqgpqqs qppsqqplts lpaqptaqst sqlqvqaltq 721 qqqsptkavp algksppbhs gfggyqqada skqlwnpqgv qgplgkimpv kqpyylqtqd 781 piklfepslq ppvmqqqple kkmkpfpmep ynhnpsevkv pefywdssys madnrsvmaq 841 qanidrrgka spgifrpeqd pvprmpfedp ksspllppdl lkslaaleee eelif sntpd 901 lypallgpla slpgrslfks llekpselms hsssflsltg fslnqerypn nsmfnevygk 961 nltssskael spsmapqcts lyslfegtpw spslpassdh stpasqsphs snpsslpssp 1021 pthnhnsvpf snfgpigtpd nrdrrtadrw ktdkpamggf gidylsatss sesswhqast 1081 psgtwtghgp smedssavlm eslkkqqkgv qqlqpkrqse eegsssicva hrgprplpsc 1141 slpastfrvk fkaartcahq aqkktrrrpf wkrrkkgk
```

We claim:

1. A method of reducing TAR-DNA-binding protein 43 (TDP-43)-mediated neuronal cytotoxicity in a human subject suffering from amyotrophic lateral sclerosis (ALS), wherein the human subject does not have a mutation in a SOD1 gene, the method comprising: administering to the human subject a composition comprising a UPF2 polypeptide or a nucleic acid encoding the UPF2 polypeptide or a vector comprising the nucleic acid encoding the UPF2 polypeptide, thereby reducing the TDP-43-mediated neuronal cytotoxicity in the human subject, wherein the UPF2 polypeptide comprises the amino acid sequence of SEQ ID NO:4.

2. The method of claim 1, wherein the composition comprises the nucleic acid encoding the UPF2 polypeptide.

3. The method of claim 1, wherein the composition comprises the vector comprising the nucleic acid encoding the UPF2 polypeptide.

4. The method of claim 3, wherein the vector is a viral vector.

5. The method of claim 4, wherein the viral vector is a retroviral vector, a lentiviral vector, an adenoviral vector, or an adeno-associated viral vector.

6. The method of claim 1, wherein the composition is administered into a central nervous system of the human subject.

7. The method of claim 1, wherein the composition is administered to the human subject by intrathecal injection.

8. A method of reducing fused in sarcoma/translocated in sarcoma (FUS/TLS)- or TDP-43-mediated neuronal cytotoxicity in a neuronal or glial cell in need thereof, wherein the neuronal or glial cell does not have a SOD1 mutation, the method comprising: providing to the neuronal or glial cell a composition comprising a UPF2 polypeptide or a nucleic acid encoding the UPF2 polypeptide or a vector comprising the nucleic acid encoding the UPF2 polypeptide, thereby reducing the FUS/TLS- or TDP-43-mediated neuronal cytotoxicity in the neuronal or glial cell; wherein the UPF2 polypeptide comprises the amino acid sequence of SEQ ID NO:4.

9. The method of claim 8, wherein the neuronal or glial cell is in a human subject and wherein the composition is administered into a central nervous system of the human subject.

10. The method of claim 9, wherein the composition is administered to the human subject by intrathecal injection.

11. The method of claim 8, wherein the composition comprises the nucleic acid encoding the UPF2 polypeptide.

12. The method of claim 8, wherein the composition comprises the vector comprising the nucleic acid encoding the UPF2 polypeptide.

13. The method of claim 12, wherein the vector is a viral vector.

14. The method of claim 13, wherein the viral vector is a retroviral vector, a lentiviral vector, an adenoviral vector, or an adeno-associated viral vector.

15. The method of claim 8, wherein the neuronal cytotoxicity is the FUS/TLS-mediated neuronal cytotoxicity.

16. The method of claim 8, wherein the neuronal cytotoxicity is the TDP-43-mediated neuronal cytotoxicity.

* * * * *

SEQUENCE LISTING

<160> NUMBER OF SEQ ID NOS: 14

<210> SEQ ID NO 1
<211> LENGTH: 3357
<212> TYPE: DNA
<213> ORGANISM: Homo sapiens

<400> SEQUENCE: 1

| | | | | | |
|---|---|---|---|---|---|
| atgagcgtgg | aggcgtacgg | gcccagctcg | cagactctca | ctttcctgga | cacggaggag | 60 |
| gccgagctgc | ttggcgccga | cacacagggc | tccgagttcg | agttcaccga | ctttactctt | 120 |
| cctagccaga | cgcagacgcc | ccccggcggc | cccggcggcc | cgggcggtgg | cggcgcggga | 180 |
| agcccgggcg | gcgcgggcgc | cggcgctgcg | gcgggacagc | tcgacgcgca | ggttgggccc | 240 |
| gaaggcatcc | tgcagaacgg | ggctgtggac | gacagtgtag | ccaagaccag | ccagttgttg | 300 |
| gctgagttga | acttcgagga | agatgaagaa | gacacctatt | acacgaagga | cctcccccata | 360 |
| cacgcctgca | gttactgtgg | aatacacgat | cctgcctgcg | tggtttactg | taataccagc | 420 |
| aagaagtggt | tctgcaacgg | acgtggaaat | acttctggca | ccacattgt | aaatcacctt | 480 |
| gtgagggcaa | aatgcaaaga | ggtgaccctg | cacaaggacg | ggcccctggg | ggagacagtc | 540 |
| ctggagtgct | acaactgcgg | ctgtcgcaac | gtcttcctcc | tcggcttcat | cccggccaaa | 600 |
| gctgactcag | tggtggtgct | gctgtgcagg | cagcccgtg | ccagcagag | cagcctcaag | 660 |
| gacatcaact | gggacagctc | gcagtggcag | ccgctgatcc | aggaccgctg | cttcctgtcc | 720 |
| tggctggtca | gatcccctc | cgagcaggag | cagctgcggg | cacgccagat | cacggcacag | 780 |
| cagatcaaca | agctggagga | gctgtggaag | gaaaacccct | ctgccacgct | ggaggacctg | 840 |
| gagaagccgg | gggtggacga | ggagccgcag | catgtcctcc | tgcggtacga | ggacgcctac | 900 |
| cagtaccaga | acatattcgg | gcccctggtc | aagctggagg | ccgactacga | caagaagctg | 960 |
| aaggagtccc | agactcaaga | taacatcact | gtcaggtggg | acctgggcct | taacaagaag | 1020 |
| agaatcgcct | acttcactt | gcccaagact | gactctgaca | tgcggctcat | gcaggggat | 1080 |
| gagatatgcc | tgcggtacaa | aggggaccct | gcgcccctgt | ggaaagggat | cggccacgtc | 1140 |
| atcaaggtcc | ctgataatta | tggcgatgag | atcgccattg | agctgcggag | cagcgtgggt | 1200 |
| gcacctgtgg | aggtgactca | caacttccag | gtggattttg | tgtggaagtc | gacctccttt | 1260 |
| gacaggatgc | agagcgcatt | gaaaacgttt | gccgtggatg | agacctcggt | gtctggctac | 1320 |
| atctaccaca | agctgttggg | ccacgaggtg | gaggacgtaa | tcaccaagtg | ccagctgccc | 1380 |
| aagcgcttca | cggcgcaggg | cctccccgac | ctcaaccact | cccaggttta | tgccgtgaag | 1440 |
| actgtgctgc | aaagaccact | gagcctgatc | cagggcccgc | caggcacggg | gaagacggtg | 1500 |
| acgtcggcca | ccatcgtcta | ccacctggcc | cggcaaggca | acggccggt | gctggtgtgt | 1560 |
| gctccgagca | acatcgccgt | ggaccagcta | acggagaaga | tccaccagac | ggggctaaag | 1620 |
| gtcgtgcgcc | tctgcgccaa | gagccgtgag | gccatcgact | ccccggtgtc | ttttctggcc | 1680 |
| ctgcacaacc | agatcaggaa | catggacagc | atgcctgagc | tgcagaagct | gcagcagctg | 1740 |
| aaagacgaga | ctggggagct | gtcgtctgcc | gacgagaagc | ggtaccgggc | cttgaagcgc | 1800 |
| accgcagaga | gagctgct | gatgaacgca | gatgtcatct | gctgcacatg | tgtgggcgcc | 1860 |
| ggtgacccga | ggctggccaa | gatgcagttc | cgctccattt | taatcgacga | aagcacccag | 1920 |
| gccaccgagc | cggagtgcat | ggttcccgtg | gtcctcgggg | ccaagcagct | gatccttgta | 1980 |
| ggcgaccact | gccagctggg | cccagtggtg | atgtgcaaga | aggcggccaa | ggccgggctg | 2040 |
| tcacagtcgc | tcttcgagcg | cctggtggtg | ctgggcatcc | ggcccatccg | cctgcaggtc | 2100 |

-continued

```
cagtaccgga tgcaccctgc actcagcgcc ttcccatcca acatcttcta cgagggctcc   2160
ctccagaatg gtgtcactgc agcggatcgt gtgaagaagg gatttgactt ccagtggccc   2220
caacccgata aaccgatgtt cttctacgtg acccagggcc aagaggagat tgccagctcg   2280
ggcacctcct acctgaacag gaccgaggct gcgaacgtgg agaagatcac cacgaagttg   2340
ctgaaggcag gcgccaagcc ggaccagatt ggcatcatca cgccctacga gggccagcgc   2400
tcctacctgg tgcagtacat gcagttcagc ggctccctgc acaccaagct ctaccaggaa   2460
gtggagatcg ccagtgtgga cgcctttcag ggacgcgaga aggacttcat catcctgtcc   2520
tgtgtgcggg ccaacgagca ccaaggcatt ggcttttaa atgaccccag gcgtctgaac    2580
gtggccctga ccagagcaag gtatggcgtc atcattgtgg caacccgaa ggcactatca    2640 aagcagccgc tctggaacca cctgctgaac tactataagg agcagaaggt gctggtggag   2700
gggccgctca acaacctgcg tgagagcctc atgcagttca gcaagccacg gaagctggtc   2760
aacactatca acccgggagc ccgcttcatg accacagcca tgtatgatgc ccggaggcc    2820 atcatcccag gctccgtcta tgatcggagc agccagggcc ggccttccag catgtacttc   2880
cagacccatg accagattgg catgatcagt gccggcccta gccacgtggc tgccatgaac   2940
attcccatcc ccttcaacct ggtcatgcca cccatgccac cgcctggcta ttttggacaa   3000
gccaacgggc tgctgcagg gcgaggcacc ccgaaaggca agactggtcg tggggggacgc    3060 cagaagaacc gctttgggct tcctggaccc agccagacta acctccccaa cagccaagcc   3120
agccaggatg tggcgtcaca gcccttctct cagggcgccc tgacgcaggg ctacatctcc   3180
atgagccagc cttcccagat gagccagccc ggcctctccc agccggagct gtcccaggac   3240
agttaccttg gtgacgagtt taaatcacaa atcgacgtgg cgctctcaca ggactccacg   3300 taccaggag agcgggctta ccagcatggc ggggtgacgg ggctgtccca gtattaa      3357
```

<210> SEQ ID NO 2
<211> LENGTH: 1118
<212> TYPE: PRT
<213> ORGANISM: Homo sapiens

<400> SEQUENCE: 2

```
Met Ser Val Glu Ala Tyr Gly Pro Ser Ser Gln Thr Leu Thr Phe Leu
1               5                   10                  15

Asp Thr Glu Glu Ala Glu Leu Leu Gly Ala Asp Thr Gln Gly Ser Glu
                20                  25                  30

Phe Glu Phe Thr Asp Phe Thr Leu Pro Ser Gln Thr Gln Thr Pro Pro
            35                  40                  45

Gly Gly Pro Gly Gly Pro Gly Gly Gly Ala Gly Ser Pro Gly Gly
        50                  55                  60

Ala Gly Ala Gly Ala Ala Gly Gln Leu Asp Ala Gln Val Gly Pro
65                  70                  75                  80

Glu Gly Ile Leu Gln Asn Gly Ala Val Asp Asp Ser Val Ala Lys Thr
                85                  90                  95

Ser Gln Leu Leu Ala Glu Leu Asn Phe Glu Glu Asp Glu Glu Asp Thr
                100                 105                 110

Tyr Tyr Thr Lys Asp Leu Pro Ile His Ala Cys Ser Tyr Cys Gly Ile
            115                 120                 125

His Asp Pro Ala Cys Val Val Tyr Cys Asn Thr Ser Lys Lys Trp Phe
        130                 135                 140

Cys Asn Gly Arg Gly Asn Thr Ser Gly Ser His Ile Val Asn His Leu
```

-continued

```
            145                 150                 155                 160

Val Arg Ala Lys Cys Lys Glu Val Thr Leu His Lys Asp Gly Pro Leu
                            165                 170                 175

Gly Glu Thr Val Leu Glu Cys Tyr Asn Cys Gly Cys Arg Asn Val Phe
                            180                 185                 190

Leu Leu Gly Phe Ile Pro Ala Lys Ala Asp Ser Val Val Leu Leu
                            195                 200                 205

Cys Arg Gln Pro Cys Ala Ser Gln Ser Ser Leu Lys Asp Ile Asn Trp
                            210                 215                 220

Asp Ser Ser Gln Trp Gln Pro Leu Ile Gln Asp Arg Cys Phe Leu Ser
        225                 230                 235                 240

Trp Leu Val Lys Ile Pro Ser Glu Gln Glu Leu Arg Ala Arg Gln
                            245                 250                 255

Ile Thr Ala Gln Gln Ile Asn Lys Leu Glu Glu Leu Trp Lys Glu Asn
                            260                 265                 270

Pro Ser Ala Thr Leu Glu Asp Leu Glu Lys Pro Gly Val Asp Glu Glu
                            275                 280                 285

Pro Gln His Val Leu Leu Arg Tyr Glu Asp Ala Tyr Gln Tyr Gln Asn
                            290                 295                 300

Ile Phe Gly Pro Leu Val Lys Leu Glu Ala Asp Tyr Asp Lys Lys Leu
        305                 310                 315                 320

Lys Glu Ser Gln Thr Gln Asp Asn Ile Thr Val Arg Trp Asp Leu Gly
                            325                 330                 335

Leu Asn Lys Lys Arg Ile Ala Tyr Phe Thr Leu Pro Lys Thr Asp Ser
                            340                 345                 350

Asp Met Arg Leu Met Gln Gly Asp Glu Ile Cys Leu Arg Tyr Lys Gly
                            355                 360                 365

Asp Leu Ala Pro Leu Trp Lys Gly Ile Gly His Val Ile Lys Val Pro
                            370                 375                 380

Asp Asn Tyr Gly Asp Glu Ile Ala Ile Glu Leu Arg Ser Ser Val Gly
        385                 390                 395                 400

Ala Pro Val Glu Val Thr His Asn Phe Gln Val Asp Phe Val Trp Lys
                            405                 410                 415

Ser Thr Ser Phe Asp Arg Met Gln Ser Ala Leu Lys Thr Phe Ala Val
                            420                 425                 430

Asp Glu Thr Ser Val Ser Gly Tyr Ile Tyr His Lys Leu Leu Gly His
                            435                 440                 445

Glu Val Glu Asp Val Ile Thr Lys Cys Gln Leu Pro Lys Arg Phe Thr
                            450                 455                 460

Ala Gln Gly Leu Pro Asp Leu Asn His Ser Gln Val Tyr Ala Val Lys
        465                 470                 475                 480

Thr Val Leu Gln Arg Pro Leu Ser Leu Ile Gln Gly Pro Pro Gly Thr
                            485                 490                 495

Gly Lys Thr Val Thr Ser Ala Thr Ile Val Tyr His Leu Ala Arg Gln
                            500                 505                 510

Gly Asn Gly Pro Val Leu Val Cys Ala Pro Ser Asn Ile Ala Val Asp
                            515                 520                 525

Gln Leu Thr Glu Lys Ile His Gln Thr Gly Leu Lys Val Val Arg Leu
                            530                 535                 540

Cys Ala Lys Ser Arg Glu Ala Ile Asp Ser Pro Val Ser Phe Leu Ala
        545                 550                 555                 560

Leu His Asn Gln Ile Arg Asn Met Asp Ser Met Pro Glu Leu Gln Lys
                            565                 570                 575
```

```
Leu Gln Gln Leu Lys Asp Glu Thr Gly Glu Leu Ser Ser Ala Asp Glu
            580                 585                 590

Lys Arg Tyr Arg Ala Leu Lys Arg Thr Ala Glu Arg Glu Leu Leu Met
            595                 600                 605

Asn Ala Asp Val Ile Cys Cys Thr Cys Val Gly Ala Gly Asp Pro Arg
            610                 615                 620

Leu Ala Lys Met Gln Phe Arg Ser Ile Leu Ile Asp Glu Ser Thr Gln
625                 630                 635                 640

Ala Thr Glu Pro Glu Cys Met Val Pro Val Leu Gly Ala Lys Gln
                645                 650                 655

Leu Ile Leu Val Gly Asp His Cys Gln Leu Gly Pro Val Val Met Cys
            660                 665                 670

Lys Lys Ala Ala Lys Ala Gly Leu Ser Gln Ser Leu Phe Glu Arg Leu
            675                 680                 685

Val Val Leu Gly Ile Arg Pro Ile Arg Leu Gln Val Gln Tyr Arg Met
            690                 695                 700

His Pro Ala Leu Ser Ala Phe Pro Ser Asn Ile Phe Tyr Glu Gly Ser
705                 710                 715                 720

Leu Gln Asn Gly Val Thr Ala Ala Asp Arg Val Lys Lys Gly Phe Asp
                725                 730                 735

Phe Gln Trp Pro Gln Pro Asp Lys Pro Met Phe Phe Tyr Val Thr Gln
            740                 745                 750

Gly Gln Glu Glu Ile Ala Ser Ser Gly Thr Ser Tyr Leu Asn Arg Thr
            755                 760                 765

Glu Ala Ala Asn Val Glu Lys Ile Thr Thr Lys Leu Leu Lys Ala Gly
            770                 775                 780

Ala Lys Pro Asp Gln Ile Gly Ile Ile Thr Pro Tyr Glu Gly Gln Arg
785                 790                 795                 800

Ser Tyr Leu Val Gln Tyr Met Gln Phe Ser Gly Ser Leu His Thr Lys
                805                 810                 815

Leu Tyr Gln Glu Val Glu Ile Ala Ser Val Asp Ala Phe Gln Gly Arg
            820                 825                 830

Glu Lys Asp Phe Ile Ile Leu Ser Cys Val Arg Ala Asn Glu His Gln
            835                 840                 845

Gly Ile Gly Phe Leu Asn Asp Pro Arg Arg Leu Asn Val Ala Leu Thr
            850                 855                 860

Arg Ala Arg Tyr Gly Val Ile Val Gly Asn Pro Lys Ala Leu Ser
865                 870                 875                 880

Lys Gln Pro Leu Trp Asn His Leu Leu Asn Tyr Tyr Lys Glu Gln Lys
                885                 890                 895

Val Leu Val Glu Gly Pro Leu Asn Asn Leu Arg Glu Ser Leu Met Gln
            900                 905                 910

Phe Ser Lys Pro Arg Lys Leu Val Asn Thr Ile Asn Pro Gly Ala Arg
            915                 920                 925

Phe Met Thr Thr Ala Met Tyr Asp Ala Arg Glu Ala Ile Ile Pro Gly
            930                 935                 940

Ser Val Tyr Asp Arg Ser Ser Gln Gly Arg Pro Ser Ser Met Tyr Phe
945                 950                 955                 960

Gln Thr His Asp Gln Ile Gly Met Ile Ser Ala Gly Pro Ser His Val
                965                 970                 975

Ala Ala Met Asn Ile Pro Ile Pro Phe Asn Leu Val Met Pro Pro Met
            980                 985                 990
```

```
Pro Pro Pro Gly Tyr Phe Gly Gln Ala Asn Gly Pro Ala  Ala Gly Arg
        995                 1000                1005

Gly Thr  Pro Lys Gly Lys Thr  Gly Arg Gly Gly Arg  Gln Lys Asn
    1010                 1015                 1020

Arg Phe  Gly Leu Pro Gly Pro  Ser Gln Thr Asn Leu  Pro Asn Ser
    1025                 1030                1035

Gln Ala  Ser Gln Asp Val Ala  Ser Gln Pro Phe Ser  Gln Gly Ala
    1040                 1045                1050

Leu Thr  Gln Gly Tyr Ile Ser  Met Ser Gln Pro Ser  Gln Met Ser
    1055                 1060                1065

Gln Pro  Gly Leu Ser Gln Pro  Glu Leu Ser Gln Asp  Ser Tyr Leu
    1070                 1075                1080

Gly Asp  Glu Phe Lys Ser Gln  Ile Asp Val Ala Leu  Ser Gln Asp
    1085                 1090                1095

Ser Thr  Tyr Gln Gly Glu Arg  Ala Tyr Gln His Gly  Gly Val Thr
    1100                 1105                1110

Gly Leu  Ser Gln Tyr
    1115
```

<210> SEQ ID NO 3
<211> LENGTH: 3819
<212> TYPE: DNA
<213> ORGANISM: Homo sapiens

<400> SEQUENCE: 3

| | | | | | |
|---|---|---|---|---|---|
| atgccagctg | agcgtaaaaa | gccagcaagt | atggaagaaa | aagactcttt | accaaacaac | 60 |
| aaggaaaaag | actgcagtga | aaggcggaca | gtgagcagca | aggagaggcc | aaaagacgat | 120 |
| atcaagctca | ctgccaagaa | ggaggtcagc | aaggcccctg | aagacaagaa | gaagagactg | 180 |
| gaagatgata | agagaaaaaa | ggaagacaag | gaacgcaaga | aaaagacga | agaaaaggtg | 240 |
| aaggcagagg | aagaatcaaa | gaaaaaagaa | gaggaagaaa | aaagaaaca | tcaagaggaa | 300 |
| gagagaaaga | agcaagaaga | gcaggccaaa | cgtcagcaag | aagaagaagc | agctgctcag | 360 |
| atgaaagaaa | aagaagaatc | cattcagctt | catcaggaag | cttgggaacg | acatcattta | 420 |
| agaaaggaac | ttcgtagcaa | aaaccaaaat | gctccggaca | gccgaccaga | ggaaaacttc | 480 |
| ttcagccgcc | tcgactcaag | tttgaagaaa | atactgcttt | tgtcaagaa | actaaaaact | 540 |
| attacagaac | aacagagaga | ctccttgtcc | catgatttta | atggcctaaa | tttaagcaaa | 600 |
| tacattgcag | aagctgtagc | ttccatcgtg | gaagcaaaac | taaaaatctc | tgatgtgaac | 660 |
| tgtgctgtgc | acctctgctc | tctctttcac | cagcgttatg | ctgactttgc | cccatcactt | 720 |
| cttcaggtct | ggaaaaaaca | ttttgaagca | aggaaagagg | agaaaacacc | taacatcacc | 780 |
| aagttaagaa | ctgatttgcg | ttttattgca | gaattgacaa | tagttgggat | tttcactgac | 840 |
| aaggaaggtc | tttccttaat | ctatgaacag | ctaaaaaata | ttattaatgc | tgatcgggag | 900 |
| tcccacactc | atgtctctgt | agtgattagt | ttctgtcgac | attgtggaga | tgatattgct | 960 |
| ggacttgtac | aaggaaagt | aaagagtgct | gcagagaagt | taatttgag | ttttcctcct | 1020 |
| agtgagataa | ttagtccaga | gaaacaacag | cccttccaga | tcttttaaa | agagtacttt | 1080 |
| acgtctttga | ccaaacacct | gaaaagggac | acagggagc | tccagaatac | tgagagacaa | 1140 |
| aacaggcgca | ttctacattc | taaaggggag | ctcagtgaag | atagacataa | acagtatgag | 1200 |
| gaatttgcta | tgtcttacca | gaagctgctg | gcaaattctc | aatccttagc | agaccttttg | 1260 |
| gatgaaaata | tgccagatct | tcctcaagac | aaacccacac | cagaagaaca | tgggcctgga | 1320 |

-continued

```
attgatatat tcacacctgg taaacctgga gaatatgact tggaaggtgg tatatgggaa    1380
gatgaagatg ctcggaattt ttatgagaac ctcattgatt tgaaggcttt tgtcccagcc    1440
atcttgttta aagacaatga aaaaagttgt cagaataaag agtccaacaa agatgatacc    1500
aaagaggcaa aagaatctaa ggagaataag gaggtatcaa gtcccgatga tttggaactt    1560
gagttggaga atctagaaat taatgatgac accttagaat tagagggtgg agatgaagct    1620
gaagatctta caaagaaact tcttgatgaa caagaacaag aagatgagga agccagcact    1680
ggatctcatc tcaagctcat agtagatgct ttcctacagc agttacccaa ctgtgtcaac    1740
cgagatctga tagacaaggc agcaatggat ttttgcatga acatgaacac aaaagcaaac    1800
aggaagaagt tggtacgggc actcttcata gttcctagac aaaggttgga tttgctacca    1860
ttttatgcaa gattggttgc tacattgcat ccctgcatgt ctgatgtagc agaggatctt    1920
tgttccatgc tgagggggga tttcagattt catgtacgga aaaaggacca gatcaatatt    1980
gaaacaaaga ataaaactgt tcgttttata ggagaactaa ctaagtttaa gatgttcacc    2040
aaaaatgaca cactgcattg tttaaagatg cttctgtcag acttctctca tcaccatatt    2100
gaaatggcat gcaccctgct ggagacatgt ggacggtttc ttttcagatc tccagaatct    2160
cacctgagga ccagtgtact tttggagcaa atgatgagaa agaagcaagc aatgcatctt    2220
gatgcgagat acgtcacaat ggtagagaat gcatattact actgcaaccc acctccagct    2280
gaaaaaaccg tgaaaagaa acgtcctcct ctccaggaat atgtccggaa acttttgtac    2340
aaagatctct ctaaggttac caccgagaag gttttgagac agatgcgaaa gctgccctgg    2400
caggaccaag aagtgaaaga ctatgttatt tgttgtatga taaacatctg gaatgtgaaa    2460
tataatagta ttcattgtgt agccaacctc ttagcaggac tagtgctcta ccaagaggat    2520
gttgggatcc acgttgtgga tggagtgtta aagatattc gattaggaat ggaggttaat    2580
caacctaaat ttaatcagag gcgcatcagc agtgccaagt tcttaggaga actttacaat    2640
taccgaatgg tggaatcagc tgttatttc agaactctgt attcttttac ctcatttggt    2700
gttaatcctg atggctctcc aagttccctg gacccacctg agcatctttt cagaattaga    2760
ctcgtatgca ctattctgga cacatgtggc cagtactttg acagaggttc cagtaaacga    2820
aaacttgatt gtttccttgt atattttcag cgttatgttt ggtggaagaa aagtttggag    2880
gtttggacaa aagaccatcc atttcctatt gatatagatt acatgatcag tgatacacta    2940
gaactgctaa gaccaaagat caaactctgt aattctctgg aagaatccat caggcaggta    3000
caagacttgg aacgagaatt cttaataaaa ctaggcctag taaatgacaa agactcaaaa    3060
gattctatga cagaaggaga aaatcttgaa gaggatgaag aagaagaaga aggtggggct    3120
gaaacagaag aacaatctgg aaatgaaagt gaagtaaatg agccagaaga agaggagggt    3180
tctgataatg atgatgatga gggagaagaa gaggaggaag agaatacaga ttaccttaca    3240
gattccaata aggaaaatga aaccgatgaa gagaatactg aggtaatgat taaaggcggt    3300
ggacttaagc atgtaccttg tgtagaagat gaggacttca ttcaagctct ggataaaatg    3360
atgctagaaa atctacagca acgaagtggt gaatctgtta aagtgcacca actagatgtg    3420
gccattcctt tgcatctcaa aagccagctg aggaaagggc ccccactggg aggtggggaa    3480
ggagaggctg agtctgcaga cacaatgccg tttgtcatgt taacaagaaa aggcaataaa    3540
cagcagttta gatccttaa tgtacccatg tcctctcaac ttgctgcaaa tcactggaac    3600
cagcaacagg cagaacaaga agagaggatg agaatgaaga agctcacact agatatcaat    3660
gaacggcaag aacaagaaga ttatcaagaa atgttgcagt ctcttgcaca gcgcccagct    3720
```

```
ccagcaaaca ccaatcgtga gaggcggcct cgctaccaac atccgaaggg agcacctaat    3780
gcagatctaa tctttaagac tggtgggagg agacgttga                           3819
```

<210> SEQ ID NO 4
<211> LENGTH: 1272
<212> TYPE: PRT
<213> ORGANISM: Homo sapiens

<400> SEQUENCE: 4

```
Met Pro Ala Glu Arg Lys Lys Pro Ala Ser Met Glu Glu Lys Asp Ser
1               5                   10                  15

Leu Pro Asn Asn Lys Glu Lys Asp Cys Ser Glu Arg Arg Thr Val Ser
            20                  25                  30

Ser Lys Glu Arg Pro Lys Asp Asp Ile Lys Leu Thr Ala Lys Lys Glu
        35                  40                  45

Val Ser Lys Ala Pro Glu Asp Lys Lys Arg Leu Glu Asp Asp Lys
    50                  55                  60

Arg Lys Lys Glu Asp Lys Glu Arg Lys Lys Asp Glu Glu Lys Val
65                  70                  75                  80

Lys Ala Glu Glu Glu Ser Lys Lys Glu Glu Glu Lys Lys Lys
                85                  90                  95

His Gln Glu Glu Glu Arg Lys Lys Gln Glu Glu Gln Ala Lys Arg Gln
                100                 105                 110

Gln Glu Glu Glu Ala Ala Ala Gln Met Lys Glu Lys Glu Glu Ser Ile
            115                 120                 125

Gln Leu His Gln Glu Ala Trp Glu Arg His His Leu Arg Lys Glu Leu
        130                 135                 140

Arg Ser Lys Asn Gln Asn Ala Pro Asp Ser Arg Pro Glu Glu Asn Phe
145                 150                 155                 160

Phe Ser Arg Leu Asp Ser Ser Leu Lys Lys Asn Thr Ala Phe Val Lys
                165                 170                 175

Lys Leu Lys Thr Ile Thr Glu Gln Gln Arg Asp Ser Leu Ser His Asp
            180                 185                 190

Phe Asn Gly Leu Asn Leu Ser Lys Tyr Ile Ala Glu Ala Val Ala Ser
        195                 200                 205

Ile Val Glu Ala Lys Leu Lys Ile Ser Asp Val Asn Cys Ala Val His
    210                 215                 220

Leu Cys Ser Leu Phe His Gln Arg Tyr Ala Asp Phe Ala Pro Ser Leu
225                 230                 235                 240

Leu Gln Val Trp Lys Lys His Phe Glu Ala Arg Lys Glu Glu Lys Thr
                245                 250                 255

Pro Asn Ile Thr Lys Leu Arg Thr Asp Leu Arg Phe Ile Ala Glu Leu
            260                 265                 270

Thr Ile Val Gly Ile Phe Thr Asp Lys Glu Gly Leu Ser Leu Ile Tyr
        275                 280                 285

Glu Gln Leu Lys Asn Ile Ile Asn Ala Asp Arg Glu Ser His Thr His
    290                 295                 300

Val Ser Val Val Ile Ser Phe Cys Arg His Cys Gly Asp Asp Ile Ala
305                 310                 315                 320

Gly Leu Val Pro Arg Lys Val Lys Ser Ala Ala Glu Lys Phe Asn Leu
                325                 330                 335

Ser Phe Pro Pro Ser Glu Ile Ile Ser Pro Glu Lys Gln Gln Pro Phe
            340                 345                 350
```

-continued

```
Gln Asn Leu Leu Lys Glu Tyr Phe Thr Ser Leu Thr Lys His Leu Lys
            355                 360                 365
Arg Asp His Arg Glu Leu Gln Asn Thr Glu Arg Gln Asn Arg Arg Ile
370                 375                 380
Leu His Ser Lys Gly Glu Leu Ser Glu Asp Arg His Lys Gln Tyr Glu
385                 390                 395                 400
Glu Phe Ala Met Ser Tyr Gln Lys Leu Leu Ala Asn Ser Gln Ser Leu
                405                 410                 415
Ala Asp Leu Leu Asp Glu Asn Met Pro Asp Leu Pro Gln Asp Lys Pro
            420                 425                 430
Thr Pro Glu Glu His Gly Pro Gly Ile Asp Ile Phe Thr Pro Gly Lys
            435                 440                 445
Pro Gly Glu Tyr Asp Leu Glu Gly Gly Ile Trp Glu Asp Glu Asp Ala
        450                 455                 460
Arg Asn Phe Tyr Glu Asn Leu Ile Asp Leu Lys Ala Phe Val Pro Ala
465                 470                 475                 480
Ile Leu Phe Lys Asp Asn Glu Lys Ser Cys Gln Asn Lys Glu Ser Asn
                485                 490                 495
Lys Asp Asp Thr Lys Glu Ala Lys Glu Ser Lys Glu Asn Lys Glu Val
            500                 505                 510
Ser Ser Pro Asp Asp Leu Glu Leu Glu Leu Glu Asn Leu Glu Ile Asn
        515                 520                 525
Asp Asp Thr Leu Glu Leu Glu Gly Gly Asp Glu Ala Glu Asp Leu Thr
            530                 535                 540
Lys Lys Leu Leu Asp Glu Gln Glu Gln Glu Asp Glu Glu Ala Ser Thr
545                 550                 555                 560
Gly Ser His Leu Lys Leu Ile Val Asp Ala Phe Leu Gln Gln Leu Pro
                565                 570                 575
Asn Cys Val Asn Arg Asp Leu Ile Asp Lys Ala Ala Met Asp Phe Cys
            580                 585                 590
Met Asn Met Asn Thr Lys Ala Asn Arg Lys Lys Leu Val Arg Ala Leu
        595                 600                 605
Phe Ile Val Pro Arg Gln Arg Leu Asp Leu Leu Pro Phe Tyr Ala Arg
610                 615                 620
Leu Val Ala Thr Leu His Pro Cys Met Ser Asp Val Ala Glu Asp Leu
625                 630                 635                 640
Cys Ser Met Leu Arg Gly Asp Phe Arg Phe His Val Arg Lys Lys Asp
                645                 650                 655
Gln Ile Asn Ile Glu Thr Lys Asn Lys Thr Val Arg Phe Ile Gly Glu
            660                 665                 670
Leu Thr Lys Phe Lys Met Phe Thr Lys Asn Asp Thr Leu His Cys Leu
        675                 680                 685
Lys Met Leu Leu Ser Asp Phe Ser His His Ile Glu Met Ala Cys
690                 695                 700
Thr Leu Leu Glu Thr Cys Gly Arg Phe Leu Phe Arg Ser Pro Glu Ser
705                 710                 715                 720
His Leu Arg Thr Ser Val Leu Leu Glu Gln Met Met Arg Lys Lys Gln
                725                 730                 735
Ala Met His Leu Asp Ala Arg Tyr Val Thr Met Val Glu Asn Ala Tyr
            740                 745                 750
Tyr Tyr Cys Asn Pro Pro Ala Glu Lys Thr Val Lys Lys Arg
        755                 760                 765
Pro Pro Leu Gln Glu Tyr Val Arg Lys Leu Leu Tyr Lys Asp Leu Ser
```

```
              770               775               780
Lys Val Thr Thr Glu Lys Val Leu Arg Gln Met Arg Lys Leu Pro Trp
785               790               795               800

Gln Asp Gln Glu Val Lys Asp Tyr Val Ile Cys Cys Met Ile Asn Ile
                  805               810               815

Trp Asn Val Lys Tyr Asn Ser Ile His Cys Val Ala Asn Leu Leu Ala
                  820               825               830

Gly Leu Val Leu Tyr Gln Glu Asp Val Gly Ile His Val Val Asp Gly
                  835               840               845

Val Leu Glu Asp Ile Arg Leu Gly Met Glu Val Asn Gln Pro Lys Phe
850               855               860

Asn Gln Arg Arg Ile Ser Ser Ala Lys Phe Leu Gly Glu Leu Tyr Asn
865               870               875               880

Tyr Arg Met Val Glu Ser Ala Val Ile Phe Arg Thr Leu Tyr Ser Phe
                  885               890               895

Thr Ser Phe Gly Val Asn Pro Asp Gly Ser Pro Ser Ser Leu Asp Pro
                  900               905               910

Pro Glu His Leu Phe Arg Ile Arg Leu Val Cys Thr Ile Leu Asp Thr
                  915               920               925

Cys Gly Gln Tyr Phe Asp Arg Gly Ser Ser Lys Arg Lys Leu Asp Cys
                  930               935               940

Phe Leu Val Tyr Phe Gln Arg Tyr Val Trp Trp Lys Lys Ser Leu Glu
945               950               955               960

Val Trp Thr Lys Asp His Pro Phe Pro Ile Asp Ile Asp Tyr Met Ile
                  965               970               975

Ser Asp Thr Leu Glu Leu Leu Arg Pro Lys Ile Lys Leu Cys Asn Ser
                  980               985               990

Leu Glu Glu Ser Ile Arg Gln Val Gln Asp Leu Glu Arg Glu Phe Leu
                  995               1000              1005

Ile Lys Leu Gly Leu Val Asn Asp Lys Asp Ser Lys Asp Ser Met
    1010              1015              1020

Thr Glu Gly Glu Asn Leu Glu Glu Asp Glu Glu Glu Glu Gly
    1025              1030              1035

Gly Ala Glu Thr Glu Glu Gln Ser Gly Asn Glu Ser Glu Val Asn
    1040              1045              1050

Glu Pro Glu Glu Glu Gly Ser Asp Asn Asp Asp Glu Gly
    1055              1060              1065

Glu Glu Glu Glu Glu Glu Asn Thr Asp Tyr Leu Thr Asp Ser Asn
    1070              1075              1080

Lys Glu Asn Glu Thr Asp Glu Glu Asn Thr Glu Val Met Ile Lys
    1085              1090              1095

Gly Gly Gly Leu Lys His Val Pro Cys Val Glu Asp Glu Asp Phe
    1100              1105              1110

Ile Gln Ala Leu Asp Lys Met Met Leu Glu Asn Leu Gln Gln Arg
    1115              1120              1125

Ser Gly Glu Ser Val Lys Val His Gln Leu Asp Val Ala Ile Pro
    1130              1135              1140

Leu His Leu Lys Ser Gln Leu Arg Lys Gly Pro Pro Leu Gly Gly
    1145              1150              1155

Gly Glu Gly Glu Ala Glu Ser Ala Asp Thr Met Pro Phe Val Met
    1160              1165              1170

Leu Thr Arg Lys Gly Asn Lys Gln Gln Phe Lys Ile Leu Asn Val
    1175              1180              1185
```

| Pro | Met | Ser | Ser | Gln | Leu | Ala | Ala | Asn | His | Trp | Asn | Gln | Gln | Gln |
|     | 1190 |     |     |     | 1195 |     |     |     |     | 1200 |     |     |     |     |

| Ala | Glu | Gln | Glu | Glu | Arg | Met | Arg | Met | Lys | Lys | Leu | Thr | Leu | Asp |
| 1205 |     |     |     |     | 1210 |     |     |     |     | 1215 |     |     |     |     |

| Ile | Asn | Glu | Arg | Gln | Glu | Gln | Glu | Asp | Tyr | Gln | Glu | Met | Leu | Gln |
|     | 1220 |     |     |     | 1225 |     |     |     |     | 1230 |     |     |     |     |

| Ser | Leu | Ala | Gln | Arg | Pro | Ala | Pro | Ala | Asn | Thr | Asn | Arg | Glu | Arg |
|     | 1235 |     |     |     | 1240 |     |     |     |     | 1245 |     |     |     |     |

| Arg | Pro | Arg | Tyr | Gln | His | Pro | Lys | Gly | Ala | Pro | Asn | Ala | Asp | Leu |
|     | 1250 |     |     |     | 1255 |     |     |     |     | 1260 |     |     |     |     |

| Ile | Phe | Lys | Thr | Gly | Gly | Arg | Arg | Arg |
|     | 1265 |     |     |     | 1270 |     |     |     |

```
<210> SEQ ID NO 5
<211> LENGTH: 1359
<212> TYPE: DNA
<213> ORGANISM: Homo sapiens

<400> SEQUENCE: 5
atgctgtcgg ccctagaagt gcagttccac cgcgactcgc agcagcagga ggctgagacg      60
ccgccaactt cgtcctccgg ttgcgggggc ggtgcgggca aacctcgcga ggagaagagg     120
acggccctga gcaaggtggt catccgccgc ctgcctccgg gctcaccaa ggagcagctg     180
gaggagcagc tgcgcccgct gccagcacac gactacttcg agttcttcgc cgccgacctg     240
agtctttatc ctcatctcta ctcaagagca tacattaatt ttaggaatcc tgatgacatc     300
cttctttta gagatcgttt tgatggatat atcttccttg acagcaaagg cctagaatat     360
cctgcagtgg tagagtttgc tccattccag aagatagcca aaaagaagct gagaaaaaaa     420
gatgccaaga ctggaagcat cgaagatgat ccagaatata gaagttttt agaaacctac     480
tgtgtggagg aagagaagac cagtgccaac cctgagactc tgctggggga gatggaggcg     540
aagacaagag agctcattgc tagaagaacc acacctcttt tggaatatat taaaaataga     600
aaattagaaa gcagagaat tcgagaagag aagcgagaag aacggaggag agagagagtta    660
gaaaagaaac gtttgcggga agaggaaaaa agaagaagaa gaagaagaga agatgcaaa     720
aaaaaagaga cagataaaca gaagaaaatt gcagagaaag aagtaaggat taagcttctt     780
aagaaaccag aaaagggaga ggaaccaacc acagagaaac caaaagaaag aggagaggag     840
attgatactg gaggtggcaa gcaggaatcc tgtgccccg gtgcagtcgt aaaagccagg     900
cccatggaag gctcgctgga ggagccccag gagacgtcac acagcggcag tgataaagag     960
cacagggatg tggagagatc tcaagaacaa gaatctgaag cacaaagata ccatgtggat    1020
gacggcagga ggcacagagc tcaccacgag cctgaacggc tttccagaag gagtgaggat    1080
gagcagagat gggggaaagg acctggccaa gacagaggga gaaggggag ccaggacagc    1140
ggggctccgg ggaggccat ggagagactg gaagagcgc aaaggtgtga cgacagtcca    1200
gcacccagaa aagagcgact ggcaaacaag gaccggccag ccttgcagct gtatgatcca    1260
ggagctcgct tccgagcgcg agagtgtggc ggaaacagga ggatctgcaa ggcagaaggt    1320
tcggggactg gtcctgagaa gagggaagag gcagagtga                           1359

<210> SEQ ID NO 6
<211> LENGTH: 452
<212> TYPE: PRT
<213> ORGANISM: Homo sapiens
```

<400> SEQUENCE: 6

```
Met Leu Ser Ala Leu Glu Val Gln Phe His Arg Asp Ser Gln Gln Gln
1               5                   10                  15

Glu Ala Glu Thr Pro Pro Thr Ser Ser Ser Gly Cys Gly Gly Gly Ala
            20                  25                  30

Gly Lys Pro Arg Glu Glu Lys Arg Thr Ala Leu Ser Lys Val Val Ile
        35                  40                  45

Arg Arg Leu Pro Pro Gly Leu Thr Lys Glu Gln Leu Glu Glu Gln Leu
    50                  55                  60

Arg Pro Leu Pro Ala His Asp Tyr Phe Glu Phe Phe Ala Ala Asp Leu
65                  70                  75                  80

Ser Leu Tyr Pro His Leu Tyr Ser Arg Ala Tyr Ile Asn Phe Arg Asn
                85                  90                  95

Pro Asp Asp Ile Leu Leu Phe Arg Asp Arg Phe Asp Gly Tyr Ile Phe
            100                 105                 110

Leu Asp Ser Lys Gly Leu Glu Tyr Pro Ala Val Val Glu Phe Ala Pro
        115                 120                 125

Phe Gln Lys Ile Ala Lys Lys Lys Leu Arg Lys Lys Asp Ala Lys Thr
    130                 135                 140

Gly Ser Ile Glu Asp Asp Pro Glu Tyr Lys Lys Phe Leu Glu Thr Tyr
145                 150                 155                 160

Cys Val Glu Glu Glu Lys Thr Ser Ala Asn Pro Glu Thr Leu Leu Gly
                165                 170                 175

Glu Met Glu Ala Lys Thr Arg Glu Leu Ile Ala Arg Arg Thr Thr Pro
            180                 185                 190

Leu Leu Glu Tyr Ile Lys Asn Arg Lys Leu Glu Lys Gln Arg Ile Arg
        195                 200                 205

Glu Glu Lys Arg Glu Glu Arg Arg Arg Glu Leu Gly Lys Lys Arg
    210                 215                 220

Leu Arg Glu Glu Glu Lys Arg Arg Arg Glu Glu Glu Arg Cys Lys
225                 230                 235                 240

Lys Lys Glu Thr Asp Lys Gln Lys Lys Ile Ala Glu Lys Glu Val Arg
                245                 250                 255

Ile Lys Leu Leu Lys Lys Pro Glu Lys Gly Glu Glu Pro Thr Thr Glu
            260                 265                 270

Lys Pro Lys Glu Arg Gly Glu Glu Ile Asp Thr Gly Gly Gly Lys Gln
        275                 280                 285

Glu Ser Cys Ala Pro Gly Ala Val Val Lys Ala Arg Pro Met Glu Gly
    290                 295                 300

Ser Leu Glu Glu Pro Gln Glu Thr Ser His Ser Gly Ser Asp Lys Glu
305                 310                 315                 320

His Arg Asp Val Glu Arg Ser Gln Glu Gln Ser Glu Ala Gln Arg
                325                 330                 335

Tyr His Val Asp Asp Gly Arg Arg His Arg Ala His His Glu Pro Glu
            340                 345                 350

Arg Leu Ser Arg Arg Ser Glu Asp Glu Gln Arg Trp Gly Lys Gly Pro
        355                 360                 365

Gly Gln Asp Arg Gly Lys Lys Gly Ser Gln Asp Ser Gly Ala Pro Gly
    370                 375                 380

Glu Ala Met Glu Arg Leu Gly Arg Ala Gln Arg Cys Asp Asp Ser Pro
385                 390                 395                 400

Ala Pro Arg Lys Glu Arg Leu Ala Asn Lys Asp Arg Pro Ala Leu Gln
                405                 410                 415
```

Leu Tyr Asp Pro Gly Ala Arg Phe Arg Ala Arg Glu Cys Gly Gly Asn
            420                 425                 430

Arg Arg Ile Cys Lys Ala Glu Gly Ser Gly Thr Gly Pro Glu Lys Arg
            435                 440                 445

Glu Glu Ala Glu
    450

<210> SEQ ID NO 7
<211> LENGTH: 10986
<212> TYPE: DNA
<213> ORGANISM: Homo sapiens

<400> SEQUENCE: 7

| | | | | | |
|---|---|---|---|---|---|
| atgagccgca | gagccccggg | gtctcggctg | agcagcggcg | gcggcggcgg | cggcaccaag | 60 |
| tatccgcgga | gctggaatga | ctggcaaccc | agaactgata | gtgcatcagc | cgacccagat | 120 |
| aatttaaaat | attcttcatc | cagagataga | ggtggttctt | cctcttatgg | actgcaacct | 180 |
| tcaaattcag | ctgtggtgtc | tcggcaaagg | cacgatgata | ccagagtcca | cgctgacata | 240 |
| cagaatgacg | aaaagggtgg | ctacagtgtc | aatggaggat | ctggggaaaa | tacttatggt | 300 |
| cggaagtcgt | tggggcaaga | gctgagggtt | aacaatgtga | ccagccctga | gttcaccagt | 360 |
| gttcagcatg | gcagtcgtgc | tttagccacc | aaagacatga | ggaaatcaca | ggagagatcg | 420 |
| atgtcttatt | ctgatgagtc | tcgactgtcg | aatcttcttc | ggaggatcac | ccgggaagac | 480 |
| gacagagacc | gaagattggc | tactgtaaag | cagttgaaag | aatttattca | gcaaccagaa | 540 |
| aataagctgg | tactagttaa | acaattggat | aatatcttgg | ctgctgtaca | tgacgtgctt | 600 |
| aatgaaagta | gcaaattgct | tcaggagttg | agacaggagg | gagcttgctg | tcttggcctt | 660 |
| ctttgtgctt | ctctgagcta | tgaggctgag | aagatcttca | agtggatttt | tagcaaattt | 720 |
| agctcatctg | caaaagatga | agttaaactc | ctctacttat | gtgccaccta | caaagcacta | 780 |
| gagactgtag | agaaaagaa | agcctttttca | tctgtaatgc | agcttgtaat | gaccagcctg | 840 |
| cagtctattc | ttgaaaatgt | ggatacacca | gaattgcttt | gtaaatgtgt | taagtgcatt | 900 |
| cttttggtgg | ctcgatgtta | ccctcatatt | ttcagcacta | attttaggga | tacagttgat | 960 |
| atattagttg | gatggcatat | agatcatact | cagaaaacctt | cgctcacgca | gcaggtatct | 1020 |
| gggtggttgc | agagtttgga | gccatttttgg | gtagctgatc | ttgcattttc | tactactctt | 1080 |
| cttggtcagt | ttctggaaga | catggaagca | tatgctgagg | acctcagcca | tgtggcctct | 1140 |
| ggggaatcag | tggatgaaga | gtccctcct | ccatcagtgt | cattaccaaa | gctggctgca | 1200 |
| cttctccggg | tatttagtac | tgtggtgagg | agcattgggg | aacgcttcag | cccaattcgg | 1260 |
| ggtcctccaa | ttactgaggc | atatgtaaca | gatgttctgt | acagagtaat | gagatgtgtg | 1320 |
| acggctgcaa | accaggtgtt | ttttctgag | gctgtgttga | cagctgctaa | tgagtgtgtt | 1380 |
| ggtgttttgc | tcggcagctt | ggatcctagc | atgactatac | attgtgacat | ggtcattaca | 1440 |
| tatgattag | accaactgga | gaattgccag | acttgtggta | ccgattatat | catctcagtc | 1500 |
| ttgaatttac | tcacgctgat | tgttgaacag | ataaatacga | aactgccatc | atcatttgta | 1560 |
| gaaaaactgt | ttataccatc | atctaaacta | ctattcttgc | gttatcataa | agaaaaagag | 1620 |
| gttgttgctg | tagcccatgc | tgtttatcaa | gcagtgctca | gcttgaagaa | tattcctgtt | 1680 |
| ttggagactg | cctataagtt | aatattggga | gaaatgactt | gtgccctaaa | caacctccta | 1740 |
| cacagtctac | aacttcctga | ggcctgttct | gaaataaaac | atgaggcttt | taagaatcat | 1800 |
| gtgttcaatg | tagacaatgc | aaaatttgta | gttatatttg | acctcagtgc | cctgactaca | 1860 |

```
attggaaatg ccaaaaactc actaataggg atgtgggcgc tatctccaac tgtctttgca   1920
cttctgagta agaatctgat gattgtgcac agtgacctgg ctgttcactt ccctgccatt   1980
cagtatgctg tgctctacac attgtattct cattgtacca ggcatgatca ctttatctct   2040
agtagcctca gttcttcctc tccttctttg tttgatggag ctgtgattag cactgtaact   2100
acggctacaa agaaacattt ctcaattata ttaaatcttc tgggaatatt acttaagaaa   2160
gataacctta accaggacac gaggaaactg ttaatgactt gggctttgga agcagctgtt   2220
ttaatgaaga agtctgaaac atacgcacct ttattctctc ttccgtcttt ccataaattt   2280
tgcaaaggcc ttttagccaa cactctcgtt gaagatgtga atatctgtct gcaggcatgc   2340
agcagtctac atgctctgtc ctcttccttg ccagatgatc ttttacagag atgtgtcgat   2400
gtttgccgtg ttcaactagt gcacagtgga actcgtattc gacaagcatt tggaaaactg   2460
ttgaaatcaa ttcctttaga tgttgtccta agcaataaca atcacacaga aattcaagaa   2520
atttctttag cattaagaag tcacatgagt aaagcaccaa gtaatacatt ccacccccaa   2580
gatttctctg atgttattag ttttattttg tatgggaact ctcatagaac agggaaggac   2640
aattggttgg aaagactgtt ctatagctgc cagagactgg ataagcgtga ccagtcaaca   2700
attccacgca atctcctgaa gacagatgct gtcctttggc agtgggccat atgggaagct   2760
gcacaattca ctgttctttc taagctgaga accccactgg gcagagctca agacaccttc   2820
cagacaattg aaggtatcat tcgaagtctc gcagctcaca cattaaaccc tgatcaggat   2880
gttagtcagt ggacaactgc agacaatgat gaaggccatg gtaacaacca acttagactt   2940
gttcttcttc tgcagtatct ggaaaatctg gagaaattaa tgtataatgc atacgaggga   3000
tgtgctaatg cattaacttc acctcccaag gtcattagaa cttttttcta taccaatcgc   3060
caaacttgtc aggactggct aacgcggatt cgactctcca tcatgagggt aggattgttg   3120
gcaggccagc ctgcagtgac agtgagacat ggctttgact tgcttacaga gatgaaaaca   3180
accagcctat ctcaggggaa tgaattggaa gtaaccatta tgatggtggt agaagcatta   3240
tgtgaacttc attgtcctga agctatacag ggaattgctg tctggtcatc atctattgtt   3300
ggaaaaaatc ttctgtggat taactcagtg gctaacagg ctgaagggag gtttgaaaag   3360
gcctctgtgg agtaccagga acacctgtgt gccatgacag gtgttgattg ctgcatctcc   3420
agctttgaca aatcggtgct cacccttagcc aatgctgggc gtaacagtgc cagcccgaaa   3480
cattctctga atggtgaatc cagaaaaact gtgctgtcca aaccgactga ctcttcccct   3540
gaggttataa attatttagg aaataaagca tgtgagtgct acatctcaat tgccgattgg   3600
gctgctgtgc aggaatggca gaacgctatc catgacttga aaagagtac cagtagcact   3660 tccctcaacc tgaaagctga cttcaactat ataaaatcat taagcagctt tgagtctgga   3720
aaatttgttg aatgtaccga gcagttagaa ttgttaccag gagaaatat caatctactt   3780 gctggaggat caaagaaaaa aatagacatg aaaaaactgc ttcctaacat gttaagtccg   3840
gatccgaggg aacttcagaa atccattgaa gttcaattgt taagaagttc tgtttgtttg   3900
gcaactgctt taacccgat agaacaagat cagaagtggc agtctataac tgaaaatgtg   3960
gtaaagtact tgaagcaaac atcccgcatc gctattggac ctctgagact ttctacttta   4020
acagtttcac agtctttgcc agttctaagt accttgcagc tgtattgctc atctgctttg   4080
gagaacacag tttctaacag actttcaaca gaggactgtc ttattccact cttcagtgaa   4140
gctttacgtt catgtaaaca gcatgacgtg aggccatgga tgcaggcatt aaggtatact   4200
```

```
atgtaccaga atcagttgtt ggagaaaatt aaagaacaaa cagtcccaat tagaagccat    4260
ctcatggaat taggtctaac agcagcaaaa tttgctagaa aacgagggaa tgtgtccctt    4320
gcaacaagac tgctggcaca gtgcagtgaa gttcagctgg gaaagaccac cactgcacag    4380
gatttagtcc aacattttaa aaaactatca acccaaggtc aagtggatga aaaatggggg    4440
cccgaacttg atattgaaaa aaccaaattg ctttatacag caggccagtc aacacatgca    4500
atggaaatgt tgagttcttg tgccatatct ttctgcaagt ctgtgaaagc tgaatatgca    4560
gttgctaaat caattctgac actggctaaa tggatccagg cagaatggaa agagatttca    4620
ggacagctga acaggtttta cagagctcag caccaacaga acttcacagg tctttctact    4680
ttgtctaaaa acatactcac tctaatagaa ctgccatctg ttaatacgat ggaagaagag    4740
tatcctcgga tcgagagtga atctacagtg catattggag ttggagaacc tgacttcatt    4800
ttgggacagt tgtatcacct gtcttcagta caggcacctg aagtagccaa atcttgggca    4860
gcgttggcca gctgggctta taggtggggc agaaaggtgg ttgacaatgc cagtcaggga    4920
gaaggtgttc gtctgctgcc tagagaaaaa tctgaagttc agaatctact tccagacact    4980
ataactgagg aagagaaaga gagaatatat ggtattcttg acaggctgt gtgtcggccg    5040 gcggggattc aggatgaaga tataacactt cagataactg agagtgaaga caacgaagaa    5100
gatgacatgg ttgatgttat ctggcgtcag ttgatatcaa gctgcccatg gctttcagaa    5160
cttgatgaaa gtgcaactga aggagttatt aaagtgtgga ggaaagttgt agatagaata    5220
ttcagcctgt acaaactctc ttgcagtgca tactttactt tccttaaact caacgctggt    5280
caaattcctt tagatgagga tgaccctagg ctgcatttaa gtcacagagt ggaacagagc    5340
actgatgaca tgattgtgat ggccacattg cgcctgctgc ggttgctcgt gaagcatgct    5400
ggtgagcttc ggcagtatct ggagcacggc ttggagacaa cacccactgc accatggaga    5460
ggaattattc cgcaactttt ctcacgctta aaccaccctg aagtgtatgt gcgccaaagt    5520
atttgtaacc ttctctgccg tgtggctcaa gattccccac atctcatatt gtatcctgca    5580
atagtgggta ccatatcgct tagtagtgaa tcccaggctt caggaaataa attttccact    5640
gcaattccaa ctttacttgg caatattcaa ggagaagaat tgctggtttc tgaatgtgag    5700
ggaggaagtc ctcctgcatc tcaggatagc aataaggatg aacctaaaag tggattaaat    5760
gaagaccaag ccatgatgca ggattgttac agcaaaattg tagataagct gtcctctgca    5820
aaccccacca tggtattaca ggttcagatg ctcgtggctg aactgcgcag ggtcactgtg    5880
ctctgggatg agctctggct gggagttttg ctgcaacaac acatgtatgt cctgagacga    5940
attcagcagc ttgaagatga ggtgaagaga gtccagaaca caacacctt acgcaaagaa    6000 gagaaaattg caatcatgag ggagaagcac acagctttga tgaagcccat cgtatttgct    6060
ttggagcatg tgaggagtat cacagcggct cctgcagaaa cacctcatga aaaatggttt    6120
caggataact atggtgatgc cattgaaaat gccctagaaa aactgaagac tccattgaac    6180
cctgcaaagc ctgggagcag ctggattcca tttaaagaga taatgctaag tttgcaacag    6240
agagcacaga aacgtgcaag ttacatcttg cgtcttgaag aaatcagtcc atggttggct    6300
gccatgacta cacactgaaat tgctcttcct ggggaagtct cagccagaga cactgtcaca    6360
atccatagtg tgggcggaac catcacaatc ttaccgacta aaaccaagcc aaagaaactt    6420
ctctttcttg gatcagatgg gaagagctat ccttatcttt tcaaaggact ggaggattta    6480
catctggatg agagaataat gcagttccta tctattgtga ataccatgtt tgctacaatt    6540
aatcgccaag aaacacccccg gttccatgct cgacactatt ctgtaacacc actaggaaca    6600
```

```
agatcaggac taatccagtg ggtagatgga gccacaccct tatttggtct ttacaaacga    6660
tggcaacaac gggaagctgc cttacaagca caaaaggccc aagattccta ccaaactcct    6720
cagaatcctg gaattgtacc ccgtcctagt gaactttatt acagtaaaat tggccctgct    6780
ttgaaaacag ttgggcttag cctggatgtg tcccgtcggg attggcctct tcatgtaatg    6840
aaggcagtat tggaagagtt aatggaggcc acaccccccga atctccttgc caaagagctc   6900
tggtcatctt gcacaacacc tgatgaatgg tggagagtta cgcagtctta tgcaagatct    6960
actgcagtca tgtctatggt tggatacata attggccttg agacagaca tctggataat     7020 gttcttatag atatgacgac tggagaagtt gttcacatag attacaatgt ttgctttgaa    7080
aaaggtaaaa gccttagagt tcctgagaaa gtaccttttc gaatgacaca aaacattgaa    7140
acagcactgg gtgtaactgg agtagaaggt gtatttaggc tttcatgtga gcaggtttta    7200
cacattatgc ggcgtggcag agagaccctg ctgacgctgc tggaggcctt tgtgtacgac    7260
cctctggtgg actggacagc aggaggcgag gctgggtttg ctggtgctgt ctatggtgga    7320
ggtggccagc aggccgagag caagcagagc aagagagaga tggagcgaga gatcacccgc    7380
agcctgtttt cttctagagt agctgagatt aaggtgaact ggtttaagaa tagagatgag    7440
atgctggttg tgcttcccaa gttggacggt agcttagatg aatacctaag cttgcaagag    7500
caactgacag atgtggaaaa actgcagggc aaactactgg aggaaataga gtttctagaa    7560
ggagctgaag gggtggatca tccttctcat actctgcaac acaggtattc tgagcacacc    7620
caactacaga ctcagcaaag agctgttcag gaagcaatcc aggtgaagct gaatgaattt    7680
gaacaatgga taacacatta tcaggctgca ttcaataatt tagaagcaac acagcttgca    7740
agcttgcttc aagagataag cacacaaatg gaccttggtc ctccaagtta cgtgccagca    7800
acagcctttc tgcagaatgc tggtcaggcc cacttgatta gccagtgcga gcagctggag    7860 gggggaggttg gtgctctcct gcagcagagg cgctccgtgc tccgtggctg tctggagcaa   7920
ctgcatcact atgcaaccgt ggccctgcag tatccgaagg ccatatttca gaaacatcga    7980
attgaacagt ggaagacctg gatggaagag ctcatctgta acaccacagt agagcgttgt    8040
caagagctct ataggaaata tgaaatgcaa tatgctcccc agccacccc aacagtgtgt     8100 cagttcatca ctgccactga aatgacccctg cagcgatacg cagcagacat caacagcaga   8160
cttattagac aagtggaacg cttgaaacag gaagctgtca ctgtgccagt ttgtgaagat    8220
cagttgaaag aaattgaacg ttgcattaaa gttttccttc atgagaatgg agaagaagga    8280
tctttgagtc tagcaagtgt tattatttct gccctttgta cccttacaag gcgtaacctg    8340
atgatggaag gtgcagcgtc aagtgctgga gaacagctgg ttgatctgac ttctcgggat    8400
ggagcctggt tcttgagga actctgcagt atgagcggaa acgtcacctg cttggttcag    8460
ttactgaagc agtgccacct ggtgccacag gacttagata tcccgaaccc catggaagcg    8520
tctgagacag ttcacttagc caatggagtg tatacctcac ttcaggaatt gaattcgaat    8580
ttccggcaaa tcatatttcc agaagcactt cgatgtttaa tgaaggggga atacacgtta    8640
gaaagtatgc tgcatgaact ggacggtctt attgagcaga ccaccgatgg cgttcccctg    8700
cagactctag tggaatctct tcaggcctac ttaagaaacg cagctatggg actggaagaa    8760
gaaacacatg ctcattacat cgatgttgcc agactactac atgctcagta cggtgaatta    8820
atccaaccga gaaatggttc agttgatgaa cacccaaaa tgtcagctgg ccagatgctt     8880
ttggtagcat tcgatggcat gtttgctcaa gttgaaactg ctttcagctt attagttgaa    8940
```

```
aagttgaaca agatggaaat tcccatagct tggcgaaaga ttgacatcat aagggaagcc    9000
aggagtactc aagttaattt ttttgatgat gataatcacc ggcaggtgct agaagagatt    9060
ttctttctaa aaagactaca gactattaag gagttcttca ggctctgtgg tacctttct     9120
aaaacattgt caggatcaag ttcacttgaa gatcagaata ctgtgaatgg gcctgtacag    9180
attgtcaatg tgaaaaccct ttttagaaac tcttgtttca gtgaagacca aatggccaaa    9240
cctatcaagg cattcacagc tgactttgtg aggcagctct tgatagggct acccaaccaa    9300
gccctcggac tcacactgtg cagttttatc agtgctctgg gtgtagacat cattgctcaa    9360
gtagaggcaa aggactttgg tgccgaaagc aaagtttctg ttgatgatct ctgtaagaaa    9420
gcggtggaac ataacatcca gatagggaag ttctctcagc tggttatgaa cagggcaact    9480
gtgttagcaa gttcttacga cactgcctgg aagaagcatg acttggtgcg aaggctagaa    9540
accagtattt cttcttgtaa gacaagcctg cagcgggttc agctgcatat tgccatgttt    9600
cagtggcaac atgaagatct acttatcaat agaccacaag ccatgtcagt cacacctccc    9660
ccacggtctg ctatcctaac cagcatgaaa agaagctgc atacctgag ccagattgaa      9720
acttctattg caacagttca ggagaagcta gctgcacttg aatcaagtat tgaacagcga    9780
ctcaagtggg caggtggtgc caaccctgca ttggcccctg tactacaaga ttttgaagca    9840
acgatagctg aaaagaagaa tcttgtcctt aaagagagcc aaagagcaag tcaggtcaca    9900
tttctctgca gcaatatcat tcattttgaa agtttacgaa caagaactgc agaagcctta    9960
aacctggatg cggcgttatt tgaactaatc aagcgatgtc agcagatgtg ttcgtttgca   10020
tcacagttta acgttcagt gtctgagtta gagcttcgtt tattacagag agtggacact     10080
ggtcttgaac atcctattgg cagctctgaa tggcttttgt cagcacacaa acagttgacc   10140
caggatatgt ctactcagag ggcaattcag acagagaaag agcagcagat agaaacggtc   10200
tgtgaaacaa ttcagaatct ggttgataat ataaagactg tgctcactgg tcataaccga   10260
cagcttggag atgtcaaaca tctcttgaaa gctatggcta aggatgaaga agctgctctg   10320
gcagatggtg aagatgttcc ctatgagaac agtgttaggc agttttgggt tgaatataaa   10380
tcatggcaag acaacattca aacagttcta tttacattag tccaggctat gggtcaggtt   10440
cgaagtcaag aacacgttga aatgctccag gaaatcactc ccaccttgaa agaactgaaa   10500
acacaaagtc agagtatcta taataattta gtgagttttg catcaccctt agtcaccgat   10560
gcaacaaatg aatgttcgag tccaacgtca tctgctactt atcagccatc cttcgctgca   10620
gcagtccgga gtaacactgg ccagaagact cagcctgatg tcatgtcaca gaatgctaga   10680
aagctgatcc agaaaaatct tgctacatca gctgatactc caccaagcac cgttccagga   10740
actggcaaga gtgttgcttg tagtcctaaa aaggcagtca gagaccctaa aactgggaaa   10800
gcggtgcaag agagaaactc ctatgcagtg agtgtgtgga agagagtgaa agccaagtta   10860
gagggccgag atgttgatcc gaataggagg atgtcagttg ctgaacaggt tgactatgtc   10920
attaaggaag caactaatct agataacttg gctcagctgt atgaaggttg gacagcctgg   10980
gtgtga                                                              10986
```

<210> SEQ ID NO 8
<211> LENGTH: 3661
<212> TYPE: PRT
<213> ORGANISM: Homo sapiens

<400> SEQUENCE: 8

Met Ser Arg Arg Ala Pro Gly Ser Arg Leu Ser Ser Gly Gly Gly Gly

-continued

```
1               5                   10                  15
Gly Gly Thr Lys Tyr Pro Arg Ser Trp Asn Asp Trp Gln Pro Arg Thr
            20                  25                  30
Asp Ser Ala Ser Ala Asp Pro Asp Asn Leu Lys Tyr Ser Ser Ser Arg
            35                  40                  45
Asp Arg Gly Gly Ser Ser Tyr Gly Leu Gln Pro Ser Asn Ser Ala
            50                  55                  60
Val Val Ser Arg Gln Arg His Asp Asp Thr Arg Val His Ala Asp Ile
 65                 70                  75                  80
Gln Asn Asp Glu Lys Gly Gly Tyr Ser Val Asn Gly Ser Gly Glu
                85                  90                  95
Asn Thr Tyr Gly Arg Lys Ser Leu Gly Gln Glu Leu Arg Val Asn Asn
            100                 105                 110
Val Thr Ser Pro Glu Phe Thr Ser Val Gln His Gly Ser Arg Ala Leu
            115                 120                 125
Ala Thr Lys Asp Met Arg Lys Ser Gln Glu Arg Ser Met Ser Tyr Ser
            130                 135                 140
Asp Glu Ser Arg Leu Ser Asn Leu Leu Arg Arg Ile Thr Arg Glu Asp
145                 150                 155                 160
Asp Arg Asp Arg Arg Leu Ala Thr Val Lys Gln Leu Lys Glu Phe Ile
                165                 170                 175
Gln Gln Pro Glu Asn Lys Leu Val Leu Val Lys Gln Leu Asp Asn Ile
            180                 185                 190
Leu Ala Ala Val His Asp Val Leu Asn Glu Ser Ser Lys Leu Leu Gln
            195                 200                 205
Glu Leu Arg Gln Glu Gly Ala Cys Cys Leu Gly Leu Leu Cys Ala Ser
            210                 215                 220
Leu Ser Tyr Glu Ala Glu Lys Ile Phe Lys Trp Ile Phe Ser Lys Phe
225                 230                 235                 240
Ser Ser Ser Ala Lys Asp Glu Val Lys Leu Leu Tyr Leu Cys Ala Thr
            245                 250                 255
Tyr Lys Ala Leu Glu Thr Val Gly Glu Lys Lys Ala Phe Ser Ser Val
            260                 265                 270
Met Gln Leu Val Met Thr Ser Leu Gln Ser Ile Leu Glu Asn Val Asp
            275                 280                 285
Thr Pro Glu Leu Leu Cys Lys Cys Val Lys Cys Ile Leu Leu Val Ala
            290                 295                 300
Arg Cys Tyr Pro His Ile Phe Ser Thr Asn Phe Arg Asp Thr Val Asp
305                 310                 315                 320
Ile Leu Val Gly Trp His Ile Asp His Thr Gln Lys Pro Ser Leu Thr
                325                 330                 335
Gln Gln Val Ser Gly Trp Leu Gln Leu Glu Pro Phe Trp Val Ala
            340                 345                 350
Asp Leu Ala Phe Ser Thr Thr Leu Leu Gly Gln Phe Leu Glu Asp Met
            355                 360                 365
Glu Ala Tyr Ala Glu Asp Leu Ser His Val Ala Ser Gly Glu Ser Val
            370                 375                 380
Asp Glu Asp Val Pro Pro Ser Val Ser Leu Pro Lys Leu Ala Ala
385                 390                 395                 400
Leu Leu Arg Val Phe Ser Thr Val Val Arg Ser Ile Gly Glu Arg Phe
                405                 410                 415
Ser Pro Ile Arg Gly Pro Pro Ile Thr Glu Ala Tyr Val Thr Asp Val
            420                 425                 430
```

```
Leu Tyr Arg Val Met Arg Cys Val Thr Ala Ala Asn Gln Val Phe Phe
        435                 440                 445

Ser Glu Ala Val Leu Thr Ala Ala Asn Glu Cys Val Gly Val Leu Leu
450                 455                 460

Gly Ser Leu Asp Pro Ser Met Thr Ile His Cys Asp Met Val Ile Thr
465                 470                 475                 480

Tyr Gly Leu Asp Gln Leu Glu Asn Cys Gln Thr Cys Gly Thr Asp Tyr
                485                 490                 495

Ile Ile Ser Val Leu Asn Leu Leu Thr Leu Ile Val Glu Gln Ile Asn
                500                 505                 510

Thr Lys Leu Pro Ser Ser Phe Val Glu Lys Leu Phe Ile Pro Ser Ser
        515                 520                 525

Lys Leu Leu Phe Leu Arg Tyr His Lys Glu Lys Glu Val Val Ala Val
530                 535                 540

Ala His Ala Val Tyr Gln Ala Val Leu Ser Leu Lys Asn Ile Pro Val
545                 550                 555                 560

Leu Glu Thr Ala Tyr Lys Leu Ile Leu Gly Glu Met Thr Cys Ala Leu
                565                 570                 575

Asn Asn Leu Leu His Ser Leu Gln Leu Pro Glu Ala Cys Ser Glu Ile
                580                 585                 590

Lys His Glu Ala Phe Lys Asn His Val Phe Asn Val Asp Asn Ala Lys
        595                 600                 605

Phe Val Val Ile Phe Asp Leu Ser Ala Leu Thr Thr Ile Gly Asn Ala
610                 615                 620

Lys Asn Ser Leu Ile Gly Met Trp Ala Leu Ser Pro Thr Val Phe Ala
625                 630                 635                 640

Leu Leu Ser Lys Asn Leu Met Ile Val His Ser Asp Leu Ala Val His
                645                 650                 655

Phe Pro Ala Ile Gln Tyr Ala Val Leu Tyr Thr Leu Tyr Ser His Cys
                660                 665                 670

Thr Arg His Asp His Phe Ile Ser Ser Ser Leu Ser Ser Ser Ser Pro
        675                 680                 685

Ser Leu Phe Asp Gly Ala Val Ile Ser Thr Val Thr Thr Ala Thr Lys
        690                 695                 700

Lys His Phe Ser Ile Ile Leu Asn Leu Leu Gly Ile Leu Leu Lys Lys
705                 710                 715                 720

Asp Asn Leu Asn Gln Asp Thr Arg Lys Leu Leu Met Thr Trp Ala Leu
                725                 730                 735

Glu Ala Ala Val Leu Met Lys Lys Ser Glu Thr Tyr Ala Pro Leu Phe
                740                 745                 750

Ser Leu Pro Ser Phe His Lys Phe Cys Lys Gly Leu Leu Ala Asn Thr
        755                 760                 765

Leu Val Glu Asp Val Asn Ile Cys Leu Gln Ala Cys Ser Ser Leu His
770                 775                 780

Ala Leu Ser Ser Ser Leu Pro Asp Asp Leu Leu Gln Arg Cys Val Asp
785                 790                 795                 800

Val Cys Arg Val Gln Leu Val His Ser Gly Thr Arg Ile Arg Gln Ala
                805                 810                 815

Phe Gly Lys Leu Leu Lys Ser Ile Pro Leu Asp Val Val Leu Ser Asn
                820                 825                 830

Asn Asn His Thr Glu Ile Gln Glu Ile Ser Leu Ala Leu Arg Ser His
        835                 840                 845
```

```
Met Ser Lys Ala Pro Ser Asn Thr Phe His Pro Gln Asp Phe Ser Asp
850                 855                 860

Val Ile Ser Phe Ile Leu Tyr Gly Asn Ser His Arg Thr Gly Lys Asp
865                 870                 875                 880

Asn Trp Leu Glu Arg Leu Phe Tyr Ser Cys Gln Arg Leu Asp Lys Arg
                885                 890                 895

Asp Gln Ser Thr Ile Pro Arg Asn Leu Leu Lys Thr Asp Ala Val Leu
            900                 905                 910

Trp Gln Trp Ala Ile Trp Glu Ala Gln Phe Thr Val Leu Ser Lys
            915                 920                 925

Leu Arg Thr Pro Leu Gly Arg Ala Gln Asp Thr Phe Gln Thr Ile Glu
930                 935                 940

Gly Ile Ile Arg Ser Leu Ala Ala His Thr Leu Asn Pro Asp Gln Asp
945                 950                 955                 960

Val Ser Gln Trp Thr Thr Ala Asp Asn Asp Glu Gly His Gly Asn Asn
                965                 970                 975

Gln Leu Arg Leu Val Leu Leu Gln Tyr Leu Glu Asn Leu Glu Lys
                980                 985                 990

Leu Met Tyr Asn Ala Tyr Glu Gly Cys Ala Asn Ala Leu Thr Ser Pro
            995                 1000                1005

Pro Lys Val Ile Arg Thr Phe Phe Tyr Thr Asn Arg Gln Thr Cys
    1010                1015                1020

Gln Asp Trp Leu Thr Arg Ile Arg Leu Ser Ile Met Arg Val Gly
    1025                1030                1035

Leu Leu Ala Gly Gln Pro Ala Val Thr Val Arg His Gly Phe Asp
    1040                1045                1050

Leu Leu Thr Glu Met Lys Thr Thr Ser Leu Ser Gln Gly Asn Glu
    1055                1060                1065

Leu Glu Val Thr Ile Met Met Val Val Glu Ala Leu Cys Glu Leu
    1070                1075                1080

His Cys Pro Glu Ala Ile Gln Gly Ile Ala Val Trp Ser Ser Ser
    1085                1090                1095

Ile Val Gly Lys Asn Leu Leu Trp Ile Asn Ser Val Ala Gln Gln
    1100                1105                1110

Ala Glu Gly Arg Phe Glu Lys Ala Ser Val Glu Tyr Gln Glu His
    1115                1120                1125

Leu Cys Ala Met Thr Gly Val Asp Cys Cys Ile Ser Ser Phe Asp
    1130                1135                1140

Lys Ser Val Leu Thr Leu Ala Asn Ala Gly Arg Asn Ser Ala Ser
    1145                1150                1155

Pro Lys His Ser Leu Asn Gly Glu Ser Arg Lys Thr Val Leu Ser
    1160                1165                1170

Lys Pro Thr Asp Ser Ser Pro Glu Val Ile Asn Tyr Leu Gly Asn
    1175                1180                1185

Lys Ala Cys Glu Cys Tyr Ile Ser Ile Ala Asp Trp Ala Ala Val
    1190                1195                1200

Gln Glu Trp Gln Asn Ala Ile His Asp Leu Lys Lys Ser Thr Ser
    1205                1210                1215

Ser Thr Ser Leu Asn Leu Lys Ala Asp Phe Asn Tyr Ile Lys Ser
    1220                1225                1230

Leu Ser Ser Phe Glu Ser Gly Lys Phe Val Glu Cys Thr Glu Gln
    1235                1240                1245

Leu Glu Leu Leu Pro Gly Glu Asn Ile Asn Leu Leu Ala Gly Gly
```

```
                 1250                1255                1260

Ser Lys Glu Lys Ile Asp Met Lys Lys Leu Leu Pro Asn Met Leu
    1265                1270                1275

Ser Pro Asp Pro Arg Glu Leu Gln Lys Ser Ile Glu Val Gln Leu
    1280                1285                1290

Leu Arg Ser Ser Val Cys Leu Ala Thr Ala Leu Asn Pro Ile Glu
    1295                1300                1305

Gln Asp Gln Lys Trp Gln Ser Ile Thr Glu Asn Val Val Lys Tyr
    1310                1315                1320

Leu Lys Gln Thr Ser Arg Ile Ala Ile Gly Pro Leu Arg Leu Ser
    1325                1330                1335

Thr Leu Thr Val Ser Gln Ser Leu Pro Val Leu Ser Thr Leu Gln
    1340                1345                1350

Leu Tyr Cys Ser Ser Ala Leu Glu Asn Thr Val Ser Asn Arg Leu
    1355                1360                1365

Ser Thr Glu Asp Cys Leu Ile Pro Leu Phe Ser Glu Ala Leu Arg
    1370                1375                1380

Ser Cys Lys Gln His Asp Val Arg Pro Trp Met Gln Ala Leu Arg
    1385                1390                1395

Tyr Thr Met Tyr Gln Asn Gln Leu Leu Glu Lys Ile Lys Glu Gln
    1400                1405                1410

Thr Val Pro Ile Arg Ser His Leu Met Glu Leu Gly Leu Thr Ala
    1415                1420                1425

Ala Lys Phe Ala Arg Lys Arg Gly Asn Val Ser Leu Ala Thr Arg
    1430                1435                1440

Leu Leu Ala Gln Cys Ser Glu Val Gln Leu Gly Lys Thr Thr Thr
    1445                1450                1455

Ala Gln Asp Leu Val Gln His Phe Lys Lys Leu Ser Thr Gln Gly
    1460                1465                1470

Gln Val Asp Glu Lys Trp Gly Pro Glu Leu Asp Ile Glu Lys Thr
    1475                1480                1485

Lys Leu Leu Tyr Thr Ala Gly Gln Ser Thr His Ala Met Glu Met
    1490                1495                1500

Leu Ser Ser Cys Ala Ile Ser Phe Cys Lys Ser Val Lys Ala Glu
    1505                1510                1515

Tyr Ala Val Ala Lys Ser Ile Leu Thr Leu Ala Lys Trp Ile Gln
    1520                1525                1530

Ala Glu Trp Lys Glu Ile Ser Gly Gln Leu Lys Gln Val Tyr Arg
    1535                1540                1545

Ala Gln His Gln Gln Asn Phe Thr Gly Leu Ser Thr Leu Ser Lys
    1550                1555                1560

Asn Ile Leu Thr Leu Ile Glu Leu Pro Ser Val Asn Thr Met Glu
    1565                1570                1575

Glu Glu Tyr Pro Arg Ile Glu Ser Glu Ser Thr Val His Ile Gly
    1580                1585                1590

Val Gly Glu Pro Asp Phe Ile Leu Gly Gln Leu Tyr His Leu Ser
    1595                1600                1605

Ser Val Gln Ala Pro Glu Val Ala Lys Ser Trp Ala Ala Leu Ala
    1610                1615                1620

Ser Trp Ala Tyr Arg Trp Gly Arg Lys Val Val Asp Asn Ala Ser
    1625                1630                1635

Gln Gly Glu Gly Val Arg Leu Leu Pro Arg Glu Lys Ser Glu Val
    1640                1645                1650
```

-continued

```
Gln Asn Leu Leu Pro Asp Thr Ile Thr Glu Glu Lys Glu Arg
    1655                1660                1665
Ile Tyr Gly Ile Leu Gly Gln Ala Val Cys Arg Pro Ala Gly Ile
    1670                1675                1680
Gln Asp Glu Asp Ile Thr Leu Gln Ile Thr Glu Ser Glu Asp Asn
    1685                1690                1695
Glu Glu Asp Asp Met Val Asp Val Ile Trp Arg Gln Leu Ile Ser
    1700                1705                1710
Ser Cys Pro Trp Leu Ser Glu Leu Asp Glu Ser Ala Thr Glu Gly
    1715                1720                1725
Val Ile Lys Val Trp Arg Lys Val Val Asp Arg Ile Phe Ser Leu
    1730                1735                1740
Tyr Lys Leu Ser Cys Ser Ala Tyr Phe Thr Phe Leu Lys Leu Asn
    1745                1750                1755
Ala Gly Gln Ile Pro Leu Asp Glu Asp Pro Arg Leu His Leu
    1760                1765                1770
Ser His Arg Val Glu Gln Ser Thr Asp Asp Met Ile Val Met Ala
    1775                1780                1785
Thr Leu Arg Leu Leu Arg Leu Leu Val Lys His Ala Gly Glu Leu
    1790                1795                1800
Arg Gln Tyr Leu Glu His Gly Leu Glu Thr Thr Pro Thr Ala Pro
    1805                1810                1815
Trp Arg Gly Ile Ile Pro Gln Leu Phe Ser Arg Leu Asn His Pro
    1820                1825                1830
Glu Val Tyr Val Arg Gln Ser Ile Cys Asn Leu Leu Cys Arg Val
    1835                1840                1845
Ala Gln Asp Ser Pro His Leu Ile Leu Tyr Pro Ala Ile Val Gly
    1850                1855                1860
Thr Ile Ser Leu Ser Ser Glu Ser Gln Ala Ser Gly Asn Lys Phe
    1865                1870                1875
Ser Thr Ala Ile Pro Thr Leu Leu Gly Asn Ile Gln Gly Glu Glu
    1880                1885                1890
Leu Leu Val Ser Glu Cys Gly Gly Ser Pro Pro Ala Ser Gln
    1895                1900                1905
Asp Ser Asn Lys Asp Glu Pro Lys Ser Gly Leu Asn Glu Asp Gln
    1910                1915                1920
Ala Met Met Gln Asp Cys Tyr Ser Lys Ile Val Asp Lys Leu Ser
    1925                1930                1935
Ser Ala Asn Pro Thr Met Val Leu Gln Val Gln Met Leu Val Ala
    1940                1945                1950
Glu Leu Arg Arg Val Thr Val Leu Trp Asp Glu Leu Trp Leu Gly
    1955                1960                1965
Val Leu Leu Gln Gln His Met Tyr Val Leu Arg Arg Ile Gln Gln
    1970                1975                1980
Leu Glu Asp Glu Val Lys Arg Val Gln Asn Asn Asn Thr Leu Arg
    1985                1990                1995
Lys Glu Glu Lys Ile Ala Ile Met Arg Glu Lys His Thr Ala Leu
    2000                2005                2010
Met Lys Pro Ile Val Phe Ala Leu Glu His Val Arg Ser Ile Thr
    2015                2020                2025
Ala Ala Pro Ala Glu Thr Pro His Glu Lys Trp Phe Gln Asp Asn
    2030                2035                2040
```

```
Tyr Gly Asp Ala Ile Glu Asn Ala Leu Glu Lys Leu Lys Thr Pro
    2045                2050                2055
Leu Asn Pro Ala Lys Pro Gly Ser Ser Trp Ile Pro Phe Lys Glu
    2060                2065                2070
Ile Met Leu Ser Leu Gln Gln Arg Ala Gln Lys Arg Ala Ser Tyr
    2075                2080                2085
Ile Leu Arg Leu Glu Glu Ile Ser Pro Trp Leu Ala Ala Met Thr
    2090                2095                2100
Asn Thr Glu Ile Ala Leu Pro Gly Glu Val Ser Ala Arg Asp Thr
    2105                2110                2115
Val Thr Ile His Ser Val Gly Gly Thr Ile Thr Ile Leu Pro Thr
    2120                2125                2130
Lys Thr Lys Pro Lys Lys Leu Leu Phe Leu Gly Ser Asp Gly Lys
    2135                2140                2145
Ser Tyr Pro Tyr Leu Phe Lys Gly Leu Glu Asp Leu His Leu Asp
    2150                2155                2160
Glu Arg Ile Met Gln Phe Leu Ser Ile Val Asn Thr Met Phe Ala
    2165                2170                2175
Thr Ile Asn Arg Gln Glu Thr Pro Arg Phe His Ala Arg His Tyr
    2180                2185                2190
Ser Val Thr Pro Leu Gly Thr Arg Ser Gly Leu Ile Gln Trp Val
    2195                2200                2205
Asp Gly Ala Thr Pro Leu Phe Gly Leu Tyr Lys Arg Trp Gln Gln
    2210                2215                2220
Arg Glu Ala Ala Leu Gln Ala Gln Lys Ala Gln Asp Ser Tyr Gln
    2225                2230                2235
Thr Pro Gln Asn Pro Gly Ile Val Pro Arg Pro Ser Glu Leu Tyr
    2240                2245                2250
Tyr Ser Lys Ile Gly Pro Ala Leu Lys Thr Val Gly Leu Ser Leu
    2255                2260                2265
Asp Val Ser Arg Arg Asp Trp Pro Leu His Val Met Lys Ala Val
    2270                2275                2280
Leu Glu Glu Leu Met Glu Ala Thr Pro Pro Asn Leu Leu Ala Lys
    2285                2290                2295
Glu Leu Trp Ser Ser Cys Thr Thr Pro Asp Glu Trp Trp Arg Val
    2300                2305                2310
Thr Gln Ser Tyr Ala Arg Ser Thr Ala Val Met Ser Met Val Gly
    2315                2320                2325
Tyr Ile Ile Gly Leu Gly Asp Arg His Leu Asp Asn Val Leu Ile
    2330                2335                2340
Asp Met Thr Thr Gly Glu Val Val His Ile Asp Tyr Asn Val Cys
    2345                2350                2355
Phe Glu Lys Gly Lys Ser Leu Arg Val Pro Glu Lys Val Pro Phe
    2360                2365                2370
Arg Met Thr Gln Asn Ile Glu Thr Ala Leu Gly Val Thr Gly Val
    2375                2380                2385
Glu Gly Val Phe Arg Leu Ser Cys Glu Gln Val Leu His Ile Met
    2390                2395                2400
Arg Arg Gly Arg Glu Thr Leu Leu Thr Leu Leu Glu Ala Phe Val
    2405                2410                2415
Tyr Asp Pro Leu Val Asp Trp Thr Ala Gly Gly Glu Ala Gly Phe
    2420                2425                2430
Ala Gly Ala Val Tyr Gly Gly Gly Gly Gln Gln Ala Glu Ser Lys
```

```
                2435                2440                2445
Gln Ser Lys Arg Glu Met Glu Arg Glu Ile Thr Arg Ser Leu Phe
    2450                2455                2460
Ser Ser Arg Val Ala Glu Ile Lys Val Asn Trp Phe Lys Asn Arg
    2465                2470                2475
Asp Glu Met Leu Val Val Leu Pro Lys Leu Asp Gly Ser Leu Asp
    2480                2485                2490
Glu Tyr Leu Ser Leu Gln Glu Gln Leu Thr Asp Val Glu Lys Leu
    2495                2500                2505
Gln Gly Lys Leu Leu Glu Glu Ile Glu Phe Leu Glu Gly Ala Glu
    2510                2515                2520
Gly Val Asp His Pro Ser His Thr Leu Gln His Arg Tyr Ser Glu
    2525                2530                2535
His Thr Gln Leu Gln Thr Gln Gln Arg Ala Val Gln Glu Ala Ile
    2540                2545                2550
Gln Val Lys Leu Asn Glu Phe Glu Gln Trp Ile Thr His Tyr Gln
    2555                2560                2565
Ala Ala Phe Asn Asn Leu Glu Ala Thr Gln Leu Ala Ser Leu Leu
    2570                2575                2580
Gln Glu Ile Ser Thr Gln Met Asp Leu Gly Pro Pro Ser Tyr Val
    2585                2590                2595
Pro Ala Thr Ala Phe Leu Gln Asn Ala Gly Gln Ala His Leu Ile
    2600                2605                2610
Ser Gln Cys Glu Gln Leu Glu Gly Glu Val Gly Ala Leu Leu Gln
    2615                2620                2625
Gln Arg Arg Ser Val Leu Arg Gly Cys Leu Glu Gln Leu His His
    2630                2635                2640
Tyr Ala Thr Val Ala Leu Gln Tyr Pro Lys Ala Ile Phe Gln Lys
    2645                2650                2655
His Arg Ile Glu Gln Trp Lys Thr Trp Met Glu Glu Leu Ile Cys
    2660                2665                2670
Asn Thr Thr Val Glu Arg Cys Gln Glu Leu Tyr Arg Lys Tyr Glu
    2675                2680                2685
Met Gln Tyr Ala Pro Gln Pro Pro Thr Val Cys Gln Phe Ile
    2690                2695                2700
Thr Ala Thr Glu Met Thr Leu Gln Arg Tyr Ala Ala Asp Ile Asn
    2705                2710                2715
Ser Arg Leu Ile Arg Gln Val Glu Arg Leu Lys Gln Glu Ala Val
    2720                2725                2730
Thr Val Pro Val Cys Glu Asp Gln Leu Lys Glu Ile Glu Arg Cys
    2735                2740                2745
Ile Lys Val Phe Leu His Glu Asn Gly Glu Glu Gly Ser Leu Ser
    2750                2755                2760
Leu Ala Ser Val Ile Ile Ser Ala Leu Cys Thr Leu Thr Arg Arg
    2765                2770                2775
Asn Leu Met Met Glu Gly Ala Ala Ser Ser Ala Gly Glu Gln Leu
    2780                2785                2790
Val Asp Leu Thr Ser Arg Asp Gly Ala Trp Phe Leu Glu Glu Leu
    2795                2800                2805
Cys Ser Met Ser Gly Asn Val Thr Cys Leu Val Gln Leu Leu Lys
    2810                2815                2820
Gln Cys His Leu Val Pro Gln Asp Leu Asp Ile Pro Asn Pro Met
    2825                2830                2835
```

```
Glu Ala Ser Glu Thr Val His Leu Ala Asn Gly Val Tyr Thr Ser
    2840            2845                2850
Leu Gln Glu Leu Asn Ser Asn Phe Arg Gln Ile Ile Phe Pro Glu
    2855            2860                2865
Ala Leu Arg Cys Leu Met Lys Gly Glu Tyr Thr Leu Glu Ser Met
    2870            2875                2880
Leu His Glu Leu Asp Gly Leu Ile Glu Gln Thr Thr Asp Gly Val
    2885            2890                2895
Pro Leu Gln Thr Leu Val Glu Ser Leu Gln Ala Tyr Leu Arg Asn
    2900            2905                2910
Ala Ala Met Gly Leu Glu Glu Glu Thr His Ala His Tyr Ile Asp
    2915            2920                2925
Val Ala Arg Leu Leu His Ala Gln Tyr Gly Glu Leu Ile Gln Pro
    2930            2935                2940
Arg Asn Gly Ser Val Asp Glu Thr Pro Lys Met Ser Ala Gly Gln
    2945            2950                2955
Met Leu Leu Val Ala Phe Asp Gly Met Phe Ala Gln Val Glu Thr
    2960            2965                2970
Ala Phe Ser Leu Leu Val Glu Lys Leu Asn Lys Met Glu Ile Pro
    2975            2980                2985
Ile Ala Trp Arg Lys Ile Asp Ile Ile Arg Glu Ala Arg Ser Thr
    2990            2995                3000
Gln Val Asn Phe Phe Asp Asp Asn His Arg Gln Val Leu Glu
    3005            3010                3015
Glu Ile Phe Phe Leu Lys Arg Leu Gln Thr Ile Lys Glu Phe Phe
    3020            3025                3030
Arg Leu Cys Gly Thr Phe Ser Lys Thr Leu Ser Gly Ser Ser Ser
    3035            3040                3045
Leu Glu Asp Gln Asn Thr Val Asn Gly Pro Val Gln Ile Val Asn
    3050            3055                3060
Val Lys Thr Leu Phe Arg Asn Ser Cys Phe Ser Glu Asp Gln Met
    3065            3070                3075
Ala Lys Pro Ile Lys Ala Phe Thr Ala Asp Phe Val Arg Gln Leu
    3080            3085                3090
Leu Ile Gly Leu Pro Asn Gln Ala Leu Gly Leu Thr Leu Cys Ser
    3095            3100                3105
Phe Ile Ser Ala Leu Gly Val Asp Ile Ile Ala Gln Val Glu Ala
    3110            3115                3120
Lys Asp Phe Gly Ala Glu Ser Lys Val Ser Val Asp Asp Leu Cys
    3125            3130                3135
Lys Lys Ala Val Glu His Asn Ile Gln Ile Gly Lys Phe Ser Gln
    3140            3145                3150
Leu Val Met Asn Arg Ala Thr Val Leu Ala Ser Ser Tyr Asp Thr
    3155            3160                3165
Ala Trp Lys Lys His Asp Leu Val Arg Arg Leu Glu Thr Ser Ile
    3170            3175                3180
Ser Ser Cys Lys Thr Ser Leu Gln Arg Val Gln Leu His Ile Ala
    3185            3190                3195
Met Phe Gln Trp Gln His Glu Asp Leu Leu Ile Asn Arg Pro Gln
    3200            3205                3210
Ala Met Ser Val Thr Pro Pro Arg Ser Ala Ile Leu Thr Ser
    3215            3220                3225
```

```
Met Lys Lys Lys Leu His Thr Leu Ser Gln Ile Glu Thr Ser Ile
3230             3235             3240

Ala Thr Val Gln Glu Lys Leu Ala Ala Leu Glu Ser Ser Ile Glu
3245             3250             3255

Gln Arg Leu Lys Trp Ala Gly Gly Ala Asn Pro Ala Leu Ala Pro
3260             3265             3270

Val Leu Gln Asp Phe Glu Ala Thr Ile Ala Glu Arg Arg Asn Leu
3275             3280             3285

Val Leu Lys Glu Ser Gln Arg Ala Ser Gln Val Thr Phe Leu Cys
3290             3295             3300

Ser Asn Ile Ile His Phe Glu Ser Leu Arg Thr Arg Thr Ala Glu
3305             3310             3315

Ala Leu Asn Leu Asp Ala Ala Leu Phe Glu Leu Ile Lys Arg Cys
3320             3325             3330

Gln Gln Met Cys Ser Phe Ala Ser Gln Phe Asn Ser Ser Val Ser
3335             3340             3345

Glu Leu Glu Leu Arg Leu Leu Gln Arg Val Asp Thr Gly Leu Glu
3350             3355             3360

His Pro Ile Gly Ser Ser Glu Trp Leu Leu Ser Ala His Lys Gln
3365             3370             3375

Leu Thr Gln Asp Met Ser Thr Gln Arg Ala Ile Gln Thr Glu Lys
3380             3385             3390

Glu Gln Gln Ile Glu Thr Val Cys Glu Thr Ile Gln Asn Leu Val
3395             3400             3405

Asp Asn Ile Lys Thr Val Leu Thr Gly His Asn Arg Gln Leu Gly
3410             3415             3420

Asp Val Lys His Leu Leu Lys Ala Met Ala Lys Asp Glu Glu Ala
3425             3430             3435

Ala Leu Ala Asp Gly Glu Asp Val Pro Tyr Glu Asn Ser Val Arg
3440             3445             3450

Gln Phe Leu Gly Glu Tyr Lys Ser Trp Gln Asp Asn Ile Gln Thr
3455             3460             3465

Val Leu Phe Thr Leu Val Gln Ala Met Gly Gln Val Arg Ser Gln
3470             3475             3480

Glu His Val Glu Met Leu Gln Glu Ile Thr Pro Thr Leu Lys Glu
3485             3490             3495

Leu Lys Thr Gln Ser Gln Ser Ile Tyr Asn Asn Leu Val Ser Phe
3500             3505             3510

Ala Ser Pro Leu Val Thr Asp Ala Thr Asn Glu Cys Ser Ser Pro
3515             3520             3525

Thr Ser Ser Ala Thr Tyr Gln Pro Ser Phe Ala Ala Ala Val Arg
3530             3535             3540

Ser Asn Thr Gly Gln Lys Thr Gln Pro Asp Val Met Ser Gln Asn
3545             3550             3555

Ala Arg Lys Leu Ile Gln Lys Asn Leu Ala Thr Ser Ala Asp Thr
3560             3565             3570

Pro Pro Ser Thr Val Pro Gly Thr Gly Lys Ser Val Ala Cys Ser
3575             3580             3585

Pro Lys Lys Ala Val Arg Asp Pro Lys Thr Gly Lys Ala Val Gln
3590             3595             3600

Glu Arg Asn Ser Tyr Ala Val Ser Val Trp Lys Arg Val Lys Ala
3605             3610             3615

Lys Leu Glu Gly Arg Asp Val Asp Pro Asn Arg Arg Met Ser Val
```

| | | | |
|---|---|---|---|
| | | 3620 | 3625 | 3630 |

Ala Glu  Gln Val Asp Tyr Val  Ile Lys Glu Ala Thr  Asn Leu Asp
         3635              3640              3645

Asn Leu  Ala Gln Leu Tyr Glu  Gly Trp Thr Ala Trp  Val
3650              3655              3660

<210> SEQ ID NO 9
<211> LENGTH: 3051
<212> TYPE: DNA
<213> ORGANISM: Homo sapiens

<400> SEQUENCE: 9

| | |
|---|---|
| atgagccaag gcccccccac aggggagagc agcgagcccg aagcaaaagt cctccacact | 60 |
| aagcggcttt accgggctgt ggtggaggct gtgcatcgac ttgacctcat cctttgcaac | 120 |
| aaaactgctt atcaagaagt attcaaacca gaaaacatta gcctgaggaa caagctgcgt | 180 |
| gagctctgcg tcaagcttat gttcctgcac ccagtggact atgggagaaa ggctgaggag | 240 |
| ctgctgtgga gaaaggtata ctatgaagtt atccagctta tcaagactaa caaaaagcac | 300 |
| atccacagcc ggagcacttt ggaatgtgcc tacaggacgc acctggttgc tggtattggc | 360 |
| ttctaccagc atctccttct ctatatccag tcccactacc agctggaact gcagtgctgc | 420 |
| atcgactgga cccatgtcac tgaccccctc ataggatgca agaagccagt gtctgcctca | 480 |
| gggaaggaga tggattgggc acagatggca tgtcaccgat gtctggtgta tctgggggat | 540 |
| ttgtcccgat atcagaatga attagctggc gtagataccg agctgctagc cgagagattt | 600 |
| tactaccaag ccctgtcagt agctcctcag attggaatgc ccttcaatca gctgggcacc | 660 |
| ctggcaggca gcaagtacta taatgtggaa gccatgtatt gctacctgcg ctgcatccag | 720 |
| tcagaagtgt cctttgaggg agcctatggg aaacctcaagc ggctgtatga caaggcagcc | 780 |
| aaaatgtacc accaactgaa gaagtgtgag actcggaaac tgtctcctgg caaaaagcga | 840 |
| tgtaaagaca ttaaaaggtt gctagtaac tttatgtatc tgcaaaagcct cctacagccc | 900 |
| aaaagcagct ccgtggactc agagctgacc tcactttgcc agtcagtcct ggaggacttc | 960 |
| aacctctgcc tcttctacct gcctcctcca cccaacctca gcctggccag tgaggatgag | 1020 |
| gaggagtatg agagtggata tgcttttcct ccggaccttc tcatcttca aatggtcatc | 1080 |
| atctgcctta tgtgtgtgca cagcttggag agagcaggat ccaagcagta cagtgcagcc | 1140 |
| attgccttca ccctggccct cttttcccac ctcgtcaatc atgtcaacat acggctgcag | 1200 |
| gctgagctgg aagagggcga gaatcccgtc cggcattcc agagtgatgg cacagatgaa | 1260 |
| ccagagtcca aggaacctgt ggagaaagag gaggagccag atcctgagcc tcctcctgta | 1320 |
| acaccccaag tgggtgaggg cagaaagagc cgtaagttct ctcgcctctc ctgtctccgc | 1380 |
| cgtcgccgcc acccacccaa agttggtgat gacagtgacc tgagtgaagg ctttgaatcg | 1440 |
| gactcaagcc atgactcagc ccgggccagt gagggctcag acagtggctc tgacaagagt | 1500 |
| cttgaaggtg ggggaacggc ctttgatgct gaaacagact cggaaatgaa tagccaggag | 1560 |
| tcccgatcag acttggaaga tatggaggaa gaggagggga cacggtcacc aaccctggag | 1620 |
| cccctcgggg gcagatcaga ggctcccgat ccctcaatg gcccactggg ccccagtgag | 1680 |
| gctagcattg ccagcaatct acaagccatg tccacccaga tgttccagac taagcgctgc | 1740 |
| ttccgactgg ccccaccctt tagcaacctg ctcctccagc ccaccaccaa ccctcatacc | 1800 |
| tcggccagcc acaggccttg cgtcaatggg gatgtagaca agccttcaga gccagcctct | 1860 |
| gaggagggct ctgagtcgga ggggagtgag tccagtggac gctcctgtcg gaatgagcgc | 1920 |

```
agcatccagg agaagcttca ggtcctgatg gccgaaggtc tgcttcctgc tgtgaaagtc    1980
ttcctggact ggcttcggac caaccccgac ctcatcatcg tgtgtgcgca gagctctcaa    2040
agtctgtgga accgcctgtc tgtgttgctg aatctgttgc ctgctgctgg tgaactccag    2100
gagtctggcc tggccttgtg tcctgaggtc caagatcttc ttgaaggttg tgaactgcct    2160
gacctcccct ctagccttct gctcccagag acatggctc ttcgtaacct gccccgctc      2220 cgagctgccc acagacgctt taactttgac acggatcggc ccctgctcag caccttagag    2280
gagtcagtgg tgcgcatctg ctgcatccgc agctttggtc atttcatcgc ccgcctgcaa    2340
ggcagcatcc tgcagttcaa cccagaggtt ggcatcttcg tcagcattgc ccagtctgag    2400
caggagagcc tgctgcagca ggcccaggca cagttccgaa tggcacagga ggaagctcgt    2460
cggaacaggc tcatgagaga catggctcag ctacgacttc agctcgaagt gtctcagctg    2520
gagggcagcc tgcagcagcc caaggcccag tcagccatgt ctccctacct cgtccctgac    2580
acccaggccc tctgccacca tctccctgtc atccgccaac tggccaccag tggccgcttc    2640
attgtcatca tcccaaggac agtgatcgat ggcctggatt tgctgaagaa ggaacaccca    2700
ggggcccggg atgggattcg gtacctggag gcagagttta aaaaggaaa caggtacatt     2760 cgctgccaga agaggtggg aaagagcttt gagcggcata agctgaagag gcaggatgca    2820
gatgcctgga ctctctataa gatcctagac agctgcaaac agctgactct ggcccagggg   2880
gcaggtgagg aggatccgag tggcatggtg accatcatca caggccttcc actggacaac   2940
cccagcgtgc tttcaggccc catgcaggca gccctgcagg ccgctgccca cgccagtgtg   3000
gacatcaaga atgttctgga cttctacaag cagtggaagg aaattggttg a            3051
```

<210> SEQ ID NO 10
<211> LENGTH: 1016
<212> TYPE: PRT
<213> ORGANISM: Homo sapiens

<400> SEQUENCE: 10

```
Met Ser Gln Gly Pro Pro Thr Gly Glu Ser Glu Pro Glu Ala Lys
1               5                   10                  15

Val Leu His Thr Lys Arg Leu Tyr Arg Ala Val Glu Ala Val His
                20                  25                  30

Arg Leu Asp Leu Ile Leu Cys Asn Lys Thr Ala Tyr Gln Glu Val Phe
                35                  40                  45

Lys Pro Glu Asn Ile Ser Leu Arg Asn Lys Leu Arg Glu Leu Cys Val
            50                  55                  60

Lys Leu Met Phe Leu His Pro Val Asp Tyr Gly Arg Lys Ala Glu Glu
65                  70                  75                  80

Leu Leu Trp Arg Lys Val Tyr Tyr Glu Val Ile Gln Leu Ile Lys Thr
                85                  90                  95

Asn Lys Lys His Ile His Ser Arg Ser Thr Leu Glu Cys Ala Tyr Arg
                100                 105                 110

Thr His Leu Val Ala Gly Ile Gly Phe Tyr Gln His Leu Leu Leu Tyr
            115                 120                 125

Ile Gln Ser His Tyr Gln Leu Glu Leu Gln Cys Ile Asp Trp Thr
            130                 135                 140

His Val Thr Asp Pro Leu Ile Gly Cys Lys Lys Pro Val Ser Ala Ser
145                 150                 155                 160

Gly Lys Glu Met Asp Trp Ala Gln Met Ala Cys His Arg Cys Leu Val
                165                 170                 175
```

-continued

```
Tyr Leu Gly Asp Leu Ser Arg Tyr Gln Asn Glu Leu Ala Gly Val Asp
            180                 185                 190

Thr Glu Leu Leu Ala Glu Arg Phe Tyr Tyr Gln Ala Leu Ser Val Ala
        195                 200                 205

Pro Gln Ile Gly Met Pro Phe Asn Gln Leu Gly Thr Leu Ala Gly Ser
    210                 215                 220

Lys Tyr Tyr Asn Val Glu Ala Met Tyr Cys Tyr Leu Arg Cys Ile Gln
225                 230                 235                 240

Ser Glu Val Ser Phe Glu Gly Ala Tyr Gly Asn Leu Lys Arg Leu Tyr
                245                 250                 255

Asp Lys Ala Ala Lys Met Tyr His Gln Leu Lys Lys Cys Glu Thr Arg
            260                 265                 270

Lys Leu Ser Pro Gly Lys Lys Arg Cys Lys Asp Ile Lys Arg Leu Leu
        275                 280                 285

Val Asn Phe Met Tyr Leu Gln Ser Leu Leu Gln Pro Lys Ser Ser Ser
    290                 295                 300

Val Asp Ser Glu Leu Thr Ser Leu Cys Gln Ser Val Leu Glu Asp Phe
305                 310                 315                 320

Asn Leu Cys Leu Phe Tyr Leu Pro Ser Ser Pro Asn Leu Ser Leu Ala
                325                 330                 335

Ser Glu Asp Glu Glu Glu Tyr Glu Ser Gly Tyr Ala Phe Leu Pro Asp
            340                 345                 350

Leu Leu Ile Phe Gln Met Val Ile Ile Cys Leu Met Cys Val His Ser
        355                 360                 365

Leu Glu Arg Ala Gly Ser Lys Gln Tyr Ser Ala Ala Ile Ala Phe Thr
    370                 375                 380

Leu Ala Leu Phe Ser His Leu Val Asn His Val Asn Ile Arg Leu Gln
385                 390                 395                 400

Ala Glu Leu Glu Glu Gly Glu Asn Pro Val Pro Ala Phe Gln Ser Asp
                405                 410                 415

Gly Thr Asp Glu Pro Glu Ser Lys Glu Pro Val Glu Lys Glu Glu Glu
            420                 425                 430

Pro Asp Pro Glu Pro Pro Val Thr Pro Gln Val Gly Glu Gly Arg
        435                 440                 445

Lys Ser Arg Lys Phe Ser Arg Leu Ser Cys Leu Arg Arg Arg His
    450                 455                 460

Pro Pro Lys Val Gly Asp Asp Ser Asp Leu Ser Glu Gly Phe Glu Ser
465                 470                 475                 480

Asp Ser Ser His Asp Ser Ala Arg Ala Ser Glu Gly Ser Asp Ser Gly
                485                 490                 495

Ser Asp Lys Ser Leu Glu Gly Gly Thr Ala Phe Asp Ala Glu Thr
            500                 505                 510

Asp Ser Glu Met Asn Ser Gln Glu Ser Arg Ser Asp Leu Glu Asp Met
        515                 520                 525

Glu Glu Glu Glu Gly Thr Arg Ser Pro Thr Leu Glu Pro Pro Arg Gly
    530                 535                 540

Arg Ser Glu Ala Pro Asp Ser Leu Asn Gly Pro Leu Gly Pro Ser Glu
545                 550                 555                 560

Ala Ser Ile Ala Ser Asn Leu Gln Ala Met Ser Thr Gln Met Phe Gln
                565                 570                 575

Thr Lys Arg Cys Phe Arg Leu Ala Pro Thr Phe Ser Asn Leu Leu Leu
            580                 585                 590
```

```
Gln Pro Thr Thr Asn Pro His Thr Ser Ala Ser His Arg Pro Cys Val
            595                 600                 605

Asn Gly Asp Val Asp Lys Pro Ser Glu Pro Ala Ser Glu Glu Gly Ser
610                 615                 620

Glu Ser Glu Gly Ser Glu Ser Ser Gly Arg Ser Cys Arg Asn Glu Arg
625                 630                 635                 640

Ser Ile Gln Glu Lys Leu Gln Val Leu Met Ala Glu Gly Leu Leu Pro
                645                 650                 655

Ala Val Lys Val Phe Leu Asp Trp Leu Arg Thr Asn Pro Asp Leu Ile
            660                 665                 670

Ile Val Cys Ala Gln Ser Ser Gln Ser Leu Trp Asn Arg Leu Ser Val
        675                 680                 685

Leu Leu Asn Leu Leu Pro Ala Ala Gly Glu Leu Gln Glu Ser Gly Leu
690                 695                 700

Ala Leu Cys Pro Glu Val Gln Asp Leu Leu Glu Gly Cys Glu Leu Pro
705                 710                 715                 720

Asp Leu Pro Ser Ser Leu Leu Pro Glu Asp Met Ala Leu Arg Asn
                725                 730                 735

Leu Pro Pro Leu Arg Ala Ala His Arg Arg Phe Asn Phe Asp Thr Asp
            740                 745                 750

Arg Pro Leu Leu Ser Thr Leu Glu Glu Ser Val Val Arg Ile Cys Cys
        755                 760                 765

Ile Arg Ser Phe Gly His Phe Ile Ala Arg Leu Gln Gly Ser Ile Leu
    770                 775                 780

Gln Phe Asn Pro Glu Val Gly Ile Phe Val Ser Ile Ala Gln Ser Glu
785                 790                 795                 800

Gln Glu Ser Leu Leu Gln Gln Ala Gln Ala Gln Phe Arg Met Ala Gln
                805                 810                 815

Glu Glu Ala Arg Arg Asn Arg Leu Met Arg Asp Met Ala Gln Leu Arg
            820                 825                 830

Leu Gln Leu Glu Val Ser Gln Leu Glu Gly Ser Leu Gln Gln Pro Lys
        835                 840                 845

Ala Gln Ser Ala Met Ser Pro Tyr Leu Val Pro Asp Thr Gln Ala Leu
850                 855                 860

Cys His His Leu Pro Val Ile Arg Gln Leu Ala Thr Ser Gly Arg Phe
865                 870                 875                 880

Ile Val Ile Ile Pro Arg Thr Val Ile Asp Gly Leu Asp Leu Leu Lys
                885                 890                 895

Lys Glu His Pro Gly Ala Arg Asp Gly Ile Arg Tyr Leu Glu Ala Glu
            900                 905                 910

Phe Lys Lys Gly Asn Arg Tyr Ile Arg Cys Gln Lys Glu Val Gly Lys
        915                 920                 925

Ser Phe Glu Arg His Lys Leu Lys Arg Gln Asp Ala Asp Ala Trp Thr
930                 935                 940

Leu Tyr Lys Ile Leu Asp Ser Cys Lys Gln Leu Thr Leu Ala Gln Gly
945                 950                 955                 960

Ala Gly Glu Glu Asp Pro Ser Gly Met Val Thr Ile Ile Thr Gly Leu
                965                 970                 975

Pro Leu Asp Asn Pro Ser Val Leu Ser Gly Pro Met Gln Ala Ala Leu
            980                 985                 990

Gln Ala Ala Ala His Ala Ser Val Asp Ile Lys Asn Val Leu Asp Phe
        995                 1000                1005

Tyr Lys Gln Trp Lys Glu Ile Gly
```

<210> SEQ ID NO 11
<211> LENGTH: 1536
<212> TYPE: DNA
<213> ORGANISM: Homo sapiens

<400> SEQUENCE: 11

| | | | | | |
|---|---|---|---|---|---|
| atggagacat | tccctgcagt | ggctgagaag | gtcctcaagg | agttccaggt | gttactgcag | 60 |
| cacagcccct | ctcccattgg | aagtacccgc | atgctgcagc | ttatgaccat | caatatgttt | 120 |
| gcagtacaca | actcccagct | gaaagactgc | ttctcggagg | agtgccgctc | tgtgatccag | 180 |
| gaacaagccg | cagctctggg | cttggccatg | ttttctctac | tggtccgccg | ctgcacctgc | 240 |
| ttacttaagg | agtccgccaa | agctcagctg | tcctctcctg | aggaccagga | tgaccaagac | 300 |
| gacatcaagg | tgtcttcctt | tgtcccggac | ctgaaggagc | tgctccccag | tgtcaaagtc | 360 |
| tggtcagatt | ggatgctcgg | ctaccccgac | acctggaatc | tcctcccac | atccctggat | 420 |
| ctgccctcgc | atgttgctgt | ggatgtatgg | tcgacgctgg | ctgatttctg | taacatactg | 480 |
| actgcagtga | atcagtctga | ggtgccactg | tacaaggacc | cggatgatga | cctcaccctt | 540 |
| cttatcctgg | aagaggatcg | gcttctctcg | ggctttgtcc | ccttgctggc | tgcccctcag | 600 |
| gacccctgct | acgtggagaa | aacctcggat | aaggttattg | cagctgactg | caaaagggtc | 660 |
| acagtgctga | agtattttct | ggaagccctt | tgtggacaag | aagagcctct | gctggcattc | 720 |
| aagggtggaa | agtatgtgtc | agtggcaccc | gtcccagaca | ccatgggaaa | ggaaatggga | 780 |
| agccaagagg | gaacacgact | ggaagatgag | gaggaggatg | tggtgattga | agactttgag | 840 |
| gaagattcag | aggctgaagg | cagcggaggc | gaggatgaca | tcagggagct | tcgggccaag | 900 |
| aagctggctc | tggccaggaa | gatagctgag | cagcagcgtc | gccaggaaaa | gatccaggct | 960 |
| gtcctggagg | accacagtca | gatgaggcag | atggagctcg | aaatcagacc | tttgttcctc | 1020 |
| gtaccagaca | ccaacggctt | cattgaccac | ctggccagtc | tggcgcggct | gctgagagc | 1080 |
| aggaagtaca | tcctggtggt | gccctcatc | gtgatcaatg | agctggacgg | cctggccaag | 1140 |
| gggcaggaga | cagaccaccg | ggctgggggc | tacgcccgtg | tggtacaaga | gaaggcccgc | 1200 |
| aagtccatcg | agttcctcga | gcagcgattc | gagagtcggg | actcttgcct | gcgagccctg | 1260 |
| accagccgtg | gcaatgaact | cgaatccatc | gccttccgca | gtgaggacat | cactggccag | 1320 |
| ctgggtaaca | acgatgatct | catcctgtcc | tgctgcctcc | actactgcaa | agacaaggct | 1380 |
| aaggacttca | tgcccgccag | caaagaggag | ccaatccggc | tactgcggga | ggtggtgctg | 1440 |
| ttgacggatg | accggaacct | gcgtgtgaag | gcgctcacaa | ggaatgttcc | tgtacgggac | 1500 |
| atcccagcct | tcctcacgtg | ggcccaggtg | ggctga | | | 1536 |

<210> SEQ ID NO 12
<211> LENGTH: 511
<212> TYPE: PRT
<213> ORGANISM: Homo sapiens

<400> SEQUENCE: 12

Met Glu Thr Phe Pro Ala Val Ala Glu Lys Val Leu Lys Glu Phe Gln
1               5                   10                  15

Val Leu Leu Gln His Ser Pro Ser Pro Ile Gly Ser Thr Arg Met Leu
                20                  25                  30

Gln Leu Met Thr Ile Asn Met Phe Ala Val His Asn Ser Gln Leu Lys
            35                  40                  45

-continued

```
Asp Cys Phe Ser Glu Glu Cys Arg Ser Val Ile Gln Glu Gln Ala Ala
 50                  55                  60

Ala Leu Gly Leu Ala Met Phe Ser Leu Leu Val Arg Arg Cys Thr Cys
 65                  70                  75                  80

Leu Leu Lys Glu Ser Ala Lys Ala Gln Leu Ser Ser Pro Glu Asp Gln
                 85                  90                  95

Asp Asp Gln Asp Asp Ile Lys Val Ser Ser Phe Val Pro Asp Leu Lys
            100                 105                 110

Glu Leu Leu Pro Ser Val Lys Val Trp Ser Asp Trp Met Leu Gly Tyr
            115                 120                 125

Pro Asp Thr Trp Asn Pro Pro Thr Ser Leu Asp Leu Pro Ser His
130                 135                 140

Val Ala Val Asp Val Trp Ser Thr Leu Ala Asp Phe Cys Asn Ile Leu
145                 150                 155                 160

Thr Ala Val Asn Gln Ser Glu Val Pro Leu Tyr Lys Asp Pro Asp Asp
                165                 170                 175

Asp Leu Thr Leu Leu Ile Leu Glu Glu Asp Arg Leu Leu Ser Gly Phe
            180                 185                 190

Val Pro Leu Leu Ala Ala Pro Gln Asp Pro Cys Tyr Val Glu Lys Thr
            195                 200                 205

Ser Asp Lys Val Ile Ala Ala Asp Cys Lys Arg Val Thr Val Leu Lys
210                 215                 220

Tyr Phe Leu Glu Ala Leu Cys Gly Gln Glu Glu Pro Leu Leu Ala Phe
225                 230                 235                 240

Lys Gly Gly Lys Tyr Val Ser Val Ala Pro Val Pro Asp Thr Met Gly
                245                 250                 255

Lys Glu Met Gly Ser Gln Glu Gly Thr Arg Leu Glu Asp Glu Glu Glu
            260                 265                 270

Asp Val Val Ile Glu Asp Phe Glu Glu Asp Ser Glu Ala Glu Gly Ser
            275                 280                 285

Gly Gly Glu Asp Asp Ile Arg Glu Leu Arg Ala Lys Lys Leu Ala Leu
            290                 295                 300

Ala Arg Lys Ile Ala Glu Gln Gln Arg Arg Gln Glu Lys Ile Gln Ala
305                 310                 315                 320

Val Leu Glu Asp His Ser Gln Met Arg Gln Met Glu Leu Glu Ile Arg
                325                 330                 335

Pro Leu Phe Leu Val Pro Asp Thr Asn Gly Phe Ile Asp His Leu Ala
            340                 345                 350

Ser Leu Ala Arg Leu Leu Glu Ser Arg Lys Tyr Ile Leu Val Val Pro
            355                 360                 365

Leu Ile Val Ile Asn Glu Leu Asp Gly Leu Ala Lys Gly Gln Glu Thr
370                 375                 380

Asp His Arg Ala Gly Gly Tyr Ala Arg Val Val Gln Glu Lys Ala Arg
385                 390                 395                 400

Lys Ser Ile Glu Phe Leu Glu Gln Arg Phe Glu Ser Arg Asp Ser Cys
                405                 410                 415

Leu Arg Ala Leu Thr Ser Arg Gly Asn Glu Leu Glu Ser Ile Ala Phe
            420                 425                 430

Arg Ser Glu Asp Ile Thr Gly Gln Leu Gly Asn Asn Asp Asp Leu Ile
            435                 440                 445

Leu Ser Cys Cys Leu His Tyr Cys Lys Asp Lys Ala Lys Asp Phe Met
450                 455                 460

Pro Ala Ser Lys Glu Glu Pro Ile Arg Leu Leu Arg Glu Val Val Leu
```

| | 465 | | | 470 | | | 475 | | | 480 | |
|---|---|---|---|---|---|---|---|---|---|---|---|

Leu Thr Asp Asp Arg Asn Leu Arg Val Lys Ala Leu Thr Arg Asn Val
                  485                 490                495

Pro Val Arg Asp Ile Pro Ala Phe Leu Thr Trp Ala Gln Val Gly
         500                 505              510

<210> SEQ ID NO 13
<211> LENGTH: 3537
<212> TYPE: DNA
<213> ORGANISM: Homo sapiens

<400> SEQUENCE: 13

```
atgagcctgc agagcgcgca gtacctccgg caggcagaag tcctgaaggc tgacatgaca     60
gattctaagc tgggtccagc tgaagtctgg acatccaggc aggctctgca ggacctgtac    120
cagaaaatgc tagttaccga tttggaatac gctttagaca agaaagtaga acaggatctc    180
tggaatcacg cctttaagaa tcagatcaca cactacaag gccaggcaaa gaatcgagca    240
aatccgaatc ggagtgaagt tcaggcaaac ctttctctgt tcctagaggc agctagtggc    300
ttctatactc agttattaca agaactgtgt acagtattta atgtagattt accatgccgt    360
gtgaagtctt cccaattggg aattatcagc aataaacaga cgcataccag cgccatagtg    420
aagccacagt ctagctcctg ttcctatatc tgccagcact gcctcgtcca ccttggagac    480
attgctcgat acagaaacca gaccagccag gcagagtcct actataggca tgcagctcag    540
cttgtcccct ccaatggtca gccttataat cagttggcta tcttagcttc ttccaaagga    600
gaccatctga ccacaatttt ctactactgc agaagcattg ctgtgaagtt ccctttccca    660
gctgcctcca ctaatctgca aaaagcactt tctaaagcac tggaaagccg agatgaggtg    720
aaaaccaagt ggggtgtttc tgacttcatc aaggccttta ttaaattcca cggtcatgtg    780
tacctgagta agagcttgga aaagttgagc cctcttcgag agaaattgga agaacagttt    840
aagaggctgc tattccaaaa agctttcaac tctcagcagt tagttcatgt cactgtcatt    900
aacctgtttc aacttcatca ccttcgtgac tttagcaatg aaaccgagca gcacacttat    960
agccaagatg agcagctatg ttggacacag ttgctggccc tctttatgtc ttttctcggc   1020
atcctgtgca agtgtcctct acagaatgag tctcaggagg agtcctacaa tgcctatcct   1080
cttccagcag tcaaggtctc catggactgg ctaagactca gacccagggt ctttcaggag   1140
gcagtggtgg atgaaagaca gtacatttgg ccctggttga tttctcttct gaatagtttc   1200
catccccatg aagaggacct ctcaagtatt agtgcgacac acttccaga ggagtttgaa   1260
ttacaaggat ttttggcatt gagaccttct ttcaggaact tggattttttc caaaggtcac   1320
cagggtatta caggggacaa agaaggccag caacgacgaa tacgacagca acgcttgatc   1380
tctataggca aatggattgc tgataatcag ccaaggctga ttcagtgtga aaatgaggta   1440
gggaaattgt tgtttatcac agaaatccca gaattaatac tggaagaccc cagtgaagcc   1500
aaagagaacc tcattctgca agaaacatct gtgatagagt cgctggctgc agatgggagc   1560
ccagggctaa aatcagtgct atctacaagc cgaaatttaa gcaacaactg tgacacagga   1620
gagaagccag tggttacctt caagaaaaac attaagacac gagaagtgaa cagagaccaa   1680
ggaagaagtt ttcctcccaa agaggtaaaa tcccagacag aactaagaaa gactccagtg   1740
tctgaagcca gaaaacaccc tgtaactcaa accccaactc aagcaagtaa ctcccagttc   1800
atccccattc atcaccctgg agccttccct cctcttccca gcaggccagg gtttccgccc   1860
ccaacatatg ttatcccccc gcctgtggca ttttctatgg gctcaggtta caccttccca   1920
```

```
gctggtgttt ctgtcccagg aacctttctt cagcctacag ctcactctcc agcaggaaac    1980
caggtgcaag ctgggaaaca gtcccacatt ccttacagcc agcaacggcc ctctggacca    2040
gggccaatga accagggacc tcaacaatca cagccaccct cccagcaacc ccttacatct    2100
ttaccagctc agccaacagc acagtctaca agccagctgc aggttcaagc tctaactcag    2160
caacaacaat ccctacaaa agctgtgccg gctttgggga aaagcccgcc tcaccactct    2220
ggattccagc agtatcaaca ggcagatgcc tccaaacagc tgtggaatcc ccctcaggtt    2280
caaggcccat tagggaaaat tatgcctgtg aaacagccct actaccttca gacccaagac    2340
cccataaaac tgtttgagcc gtcattgcaa cctcctgtaa tgcagcagca gcctctagaa    2400
aaaaaaatga agccttttcc catggagcca tataaccata atccctcaga agtcaaggtc    2460
ccagaattct actgggattc ttcctacagc atggctgata cagatctgt aatggcacag    2520 caagcaaaca tagaccgcag gggcaaacgg tcaccaggaa tcttccgtcc agagcaggat    2580
cctgtaccca gaatgccgtt tgaggacccc aagagctccc ctctgcttcc tccggacctg    2640
ttaaagagtc tggctgcctt ggaggaagag aagagctga ttttttctaa cactcctgat    2700
ctttacccgg ctctgctggg gcctctcgcc tctcttcctg gacgaagcct tttaaatcc    2760 ttattggaga agccctcaga gctcatgtca cattcatcct ctttcctgtc cctcaccgga    2820
ttctctctca atcaggaaag ataccccaaat aatagtatgt tcaatgaggt atatgggaaa    2880
aacctgacat ccagctccaa agcagaactc agtccctcaa tggcccccca ggaaacatct    2940
ctgtattccc tttttgaagg gactccgtgg tctccatcac ttcctgccag ttcagatcat    3000
tcaacaccag ccagccagtc tcctcattcc tctaacccaa gcagcctacc cagctctcct    3060
ccaacacaca accataattc tgttccattc tccaattttg acccattgg gactccagat    3120 aacagggata gaaggactgc agatcggtgg aaaactgata agccagccat gggtgggttt    3180
ggcattgatt atctctcagc aacgtcatcc tctgagagca gttggcatca ggccagcact    3240
ccgagtggca cctggacagg ccatggccct tccatggagg attcctctgc tgtcctcatg    3300
gaaagcctaa agaagcaaca gcatggggtc cagcagttgg ggcccaaaag acagtctgaa    3360
gaggaaggaa gcagcagtat ctgcgtagcc cacagagggc ccaggcccct gcccagctgc    3420
agtctcccag cctccacttt cagagtgaaa ttcaaggcag cacggacatg tgcccatcag    3480
gcacagaaga aaacacgacg tcgtccattt tggaagagac gaaagaaagg aaaataa      3537
```

<210> SEQ ID NO 14
<211> LENGTH: 1178
<212> TYPE: PRT
<213> ORGANISM: Homo sapiens

<400> SEQUENCE: 14

```
Met Ser Leu Gln Ser Ala Gln Tyr Leu Arg Gln Ala Glu Val Leu Lys
1               5                   10                  15

Ala Asp Met Thr Asp Ser Lys Leu Gly Pro Ala Glu Val Trp Thr Ser
            20                  25                  30

Arg Gln Ala Leu Gln Asp Leu Tyr Gln Lys Met Leu Val Thr Asp Leu
        35                  40                  45

Glu Tyr Ala Leu Asp Lys Lys Val Glu Gln Asp Leu Trp Asn His Ala
    50                  55                  60

Phe Lys Asn Gln Ile Thr Thr Leu Gln Gly Gln Ala Lys Asn Arg Ala
65                  70                  75                  80

Asn Pro Asn Arg Ser Glu Val Gln Ala Asn Leu Ser Leu Phe Leu Glu
```

```
                          85                  90                  95
Ala Ala Ser Gly Phe Tyr Thr Gln Leu Leu Gln Glu Leu Cys Thr Val
                100                 105                 110

Phe Asn Val Asp Leu Pro Cys Arg Val Lys Ser Ser Gln Leu Gly Ile
            115                 120                 125

Ile Ser Asn Lys Gln Thr His Thr Ser Ala Ile Val Lys Pro Gln Ser
        130                 135                 140

Ser Ser Cys Ser Tyr Ile Cys Gln His Cys Leu Val His Leu Gly Asp
145                 150                 155                 160

Ile Ala Arg Tyr Arg Asn Gln Thr Ser Gln Ala Glu Ser Tyr Tyr Arg
                165                 170                 175

His Ala Ala Gln Leu Val Pro Ser Asn Gly Gln Pro Tyr Asn Gln Leu
            180                 185                 190

Ala Ile Leu Ala Ser Ser Lys Gly Asp His Leu Thr Thr Ile Phe Tyr
        195                 200                 205

Tyr Cys Arg Ser Ile Ala Val Lys Phe Pro Phe Pro Ala Ala Ser Thr
    210                 215                 220

Asn Leu Gln Lys Ala Leu Ser Lys Ala Leu Glu Ser Arg Asp Glu Val
225                 230                 235                 240

Lys Thr Lys Trp Gly Val Ser Asp Phe Ile Lys Ala Phe Ile Lys Phe
                245                 250                 255

His Gly His Val Tyr Leu Ser Lys Ser Leu Glu Lys Leu Ser Pro Leu
            260                 265                 270

Arg Glu Lys Leu Glu Glu Gln Phe Lys Arg Leu Leu Phe Gln Lys Ala
        275                 280                 285

Phe Asn Ser Gln Gln Leu Val His Val Thr Val Ile Asn Leu Phe Gln
290                 295                 300

Leu His His Leu Arg Asp Phe Ser Asn Glu Thr Glu Gln His Thr Tyr
305                 310                 315                 320

Ser Gln Asp Glu Gln Leu Cys Trp Thr Gln Leu Leu Ala Leu Phe Met
                325                 330                 335

Ser Phe Leu Gly Ile Leu Cys Lys Cys Pro Leu Gln Asn Glu Ser Gln
            340                 345                 350

Glu Glu Ser Tyr Asn Ala Tyr Pro Leu Pro Ala Val Lys Val Ser Met
        355                 360                 365

Asp Trp Leu Arg Leu Arg Pro Arg Val Phe Gln Glu Ala Val Val Asp
    370                 375                 380

Glu Arg Gln Tyr Ile Trp Pro Trp Leu Ile Ser Leu Leu Asn Ser Phe
385                 390                 395                 400

His Pro His Glu Glu Asp Leu Ser Ser Ile Ser Ala Thr Pro Leu Pro
                405                 410                 415

Glu Glu Phe Glu Leu Gln Gly Phe Leu Ala Leu Arg Pro Ser Phe Arg
            420                 425                 430

Asn Leu Asp Phe Ser Lys Gly His Gln Gly Ile Thr Gly Asp Lys Glu
        435                 440                 445

Gly Gln Gln Arg Arg Ile Arg Gln Arg Leu Ile Ser Ile Gly Lys
    450                 455                 460

Trp Ile Ala Asp Asn Gln Pro Arg Leu Ile Gln Cys Glu Asn Glu Val
465                 470                 475                 480

Gly Lys Leu Leu Phe Ile Thr Glu Ile Pro Glu Leu Ile Leu Glu Asp
                485                 490                 495

Pro Ser Glu Ala Lys Glu Asn Leu Ile Leu Gln Glu Thr Ser Val Ile
            500                 505                 510
```

```
Glu Ser Leu Ala Ala Asp Gly Ser Pro Gly Leu Lys Ser Val Leu Ser
            515                 520                 525

Thr Ser Arg Asn Leu Ser Asn Asn Cys Asp Thr Gly Glu Lys Pro Val
        530                 535                 540

Val Thr Phe Lys Glu Asn Ile Lys Thr Arg Glu Val Asn Arg Asp Gln
545                 550                 555                 560

Gly Arg Ser Phe Pro Pro Lys Glu Val Lys Ser Gln Thr Glu Leu Arg
                565                 570                 575

Lys Thr Pro Val Ser Glu Ala Arg Lys Thr Pro Val Thr Gln Thr Pro
            580                 585                 590

Thr Gln Ala Ser Asn Ser Gln Phe Ile Pro Ile His His Pro Gly Ala
        595                 600                 605

Phe Pro Pro Leu Pro Ser Arg Pro Gly Phe Pro Pro Thr Tyr Val
            610                 615                 620

Ile Pro Pro Pro Val Ala Phe Ser Met Gly Ser Gly Tyr Thr Phe Pro
625                 630                 635                 640

Ala Gly Val Ser Val Pro Gly Thr Phe Leu Gln Pro Thr Ala His Ser
                645                 650                 655

Pro Ala Gly Asn Gln Val Gln Ala Gly Lys Gln Ser His Ile Pro Tyr
            660                 665                 670

Ser Gln Gln Arg Pro Ser Gly Pro Gly Pro Met Asn Gln Gly Pro Gln
        675                 680                 685

Gln Ser Gln Pro Pro Ser Gln Gln Pro Leu Thr Ser Leu Pro Ala Gln
690                 695                 700

Pro Thr Ala Gln Ser Thr Ser Gln Leu Gln Val Gln Ala Leu Thr Gln
705                 710                 715                 720

Gln Gln Gln Ser Pro Thr Lys Ala Val Pro Ala Leu Gly Lys Ser Pro
                725                 730                 735

Pro His His Ser Gly Phe Gln Gln Tyr Gln Gln Ala Asp Ala Ser Lys
            740                 745                 750

Gln Leu Trp Asn Pro Pro Gln Val Gln Gly Pro Leu Gly Lys Ile Met
        755                 760                 765

Pro Val Lys Gln Pro Tyr Tyr Leu Gln Thr Gln Asp Pro Ile Lys Leu
770                 775                 780

Phe Glu Pro Ser Leu Gln Pro Val Met Gln Gln Pro Leu Glu
785                 790                 795                 800

Lys Lys Met Lys Pro Phe Pro Met Glu Pro Tyr Asn His Asn Pro Ser
                805                 810                 815

Glu Val Lys Val Pro Glu Phe Tyr Trp Asp Ser Ser Tyr Ser Met Ala
            820                 825                 830

Asp Asn Arg Ser Val Met Ala Gln Gln Ala Asn Ile Asp Arg Arg Gly
        835                 840                 845

Lys Arg Ser Pro Gly Ile Phe Arg Pro Glu Gln Asp Pro Val Pro Arg
850                 855                 860

Met Pro Phe Glu Asp Pro Lys Ser Ser Pro Leu Leu Pro Asp Leu
865                 870                 875                 880

Leu Lys Ser Leu Ala Ala Leu Glu Glu Glu Glu Leu Ile Phe Ser
                885                 890                 895

Asn Thr Pro Asp Leu Tyr Pro Ala Leu Leu Gly Pro Leu Ala Ser Leu
            900                 905                 910

Pro Gly Arg Ser Leu Phe Lys Ser Leu Leu Glu Lys Pro Ser Glu Leu
        915                 920                 925
```

-continued

```
Met Ser His Ser Ser Ser Phe Leu Ser Leu Thr Gly Phe Ser Leu Asn
    930                 935                 940

Gln Glu Arg Tyr Pro Asn Asn Ser Met Phe Asn Glu Val Tyr Gly Lys
945                 950                 955                 960

Asn Leu Thr Ser Ser Ser Lys Ala Glu Leu Ser Pro Ser Met Ala Pro
            965                 970                 975

Gln Glu Thr Ser Leu Tyr Ser Leu Phe Glu Gly Thr Pro Trp Ser Pro
            980                 985                 990

Ser Leu Pro Ala Ser Ser Asp His Ser Thr Pro Ala Ser Gln Ser Pro
        995                 1000                1005

His Ser Ser Asn Pro Ser Ser Leu Pro Ser Ser Pro Pro Thr His
    1010                1015                1020

Asn His Asn Ser Val Pro Phe Ser Asn Phe Gly Pro Ile Gly Thr
    1025                1030                1035

Pro Asp Asn Arg Asp Arg Arg Thr Ala Asp Arg Trp Lys Thr Asp
    1040                1045                1050

Lys Pro Ala Met Gly Gly Phe Gly Ile Asp Tyr Leu Ser Ala Thr
    1055                1060                1065

Ser Ser Ser Glu Ser Ser Trp His Gln Ala Ser Thr Pro Ser Gly
    1070                1075                1080

Thr Trp Thr Gly His Gly Pro Ser Met Glu Asp Ser Ser Ala Val
    1085                1090                1095

Leu Met Glu Ser Leu Lys Lys Gln Gln His Gly Val Gln Gln Leu
    1100                1105                1110

Gly Pro Lys Arg Gln Ser Glu Glu Glu Gly Ser Ser Ser Ile Cys
    1115                1120                1125

Val Ala His Arg Gly Pro Arg Pro Leu Pro Ser Cys Ser Leu Pro
    1130                1135                1140

Ala Ser Thr Phe Arg Val Lys Phe Lys Ala Ala Arg Thr Cys Ala
    1145                1150                1155

His Gln Ala Gln Lys Lys Thr Arg Arg Arg Pro Phe Trp Lys Arg
    1160                1165                1170

Arg Lys Lys Gly Lys
    1175
```